(12) United States Patent
Béliveau et al.

(10) Patent No.: US 9,713,646 B2
(45) Date of Patent: *Jul. 25, 2017

(54) POTENTIATION OF ANTICANCER AGENTS

(71) Applicant: Angiochem Inc., Montreal (CA)

(72) Inventors: Richard Béliveau, Montreal (CA);
Michel Demeule, Beaconsfield (CA);
Christian Che, Longueuil (CA);
Anthony Regina, Montreal (CA)

(73) Assignee: Angiochem Inc., Montreal (CA)

( * ) Notice: Subject to any disclaimer, the term of this patent is extended or adjusted under 35 U.S.C. 154(b) by 0 days.

This patent is subject to a terminal disclaimer.

(21) Appl. No.: 14/635,856

(22) Filed: Mar. 2, 2015

(65) Prior Publication Data

US 2015/0314010 A1 Nov. 5, 2015

Related U.S. Application Data

(60) Division of application No. 11/807,917, filed on May 30, 2007, now Pat. No. 8,969,310, which is a continuation-in-part of application No. PCT/CA2006/001165, filed on Jul. 14, 2006.

(60) Provisional application No. 60/758,532, filed on Jan. 13, 2006, provisional application No. 60/699,375, filed on Jul. 15, 2005.

(51) Int. Cl.
| | | |
|---|---|---|
| *A61K 38/10* | (2006.01) | |
| *A61K 47/48* | (2006.01) | |
| *A61K 31/337* | (2006.01) | |
| *A61K 31/196* | (2006.01) | |
| *A61K 31/475* | (2006.01) | |
| *A61K 31/704* | (2006.01) | |
| *A61K 38/57* | (2006.01) | |
| *A61K 9/00* | (2006.01) | |
| *A61K 47/14* | (2017.01) | |

(52) U.S. Cl.
CPC ...... *A61K 47/48246* (2013.01); *A61K 31/196* (2013.01); *A61K 31/337* (2013.01); *A61K 31/475* (2013.01); *A61K 31/704* (2013.01); *A61K 38/57* (2013.01); *A61K 9/0019* (2013.01); *A61K 47/14* (2013.01)

(58) Field of Classification Search
None
See application file for complete search history.

(56) References Cited

U.S. PATENT DOCUMENTS

| | | |
|---|---|---|
| 4,671,958 A | 6/1987 | Rodwell et al. |
| 4,801,575 A | 1/1989 | Pardridge |
| 4,902,505 A | 2/1990 | Pardridge et al. |
| 4,942,184 A | 7/1990 | Haugwitz et al. |
| 5,028,697 A | 7/1991 | Johnson et al. |
| 5,041,424 A | 8/1991 | Saulnier et al. |
| 5,118,668 A | 6/1992 | Auerswald et al. |
| 5,169,933 A | 12/1992 | Anderson et al. |
| 5,223,409 A | 6/1993 | Ladner et al. |
| 5,258,499 A | 11/1993 | Konigsberg et al. |
| 5,362,831 A | 11/1994 | Mongelli et al. |
| 5,442,043 A | 8/1995 | Fukuta et al. |
| 5,578,451 A | 11/1996 | Nishimoto |
| 5,627,270 A | 5/1997 | Kahne et al. |
| RE35,524 E | 6/1997 | Saulnier et al. |
| 5,683,694 A | 11/1997 | Bagshawe et al. |
| 5,780,265 A | 7/1998 | Dennis et al. |
| 5,807,980 A | 9/1998 | Lasters et al. |
| 5,869,045 A | 2/1999 | Hellstrom et al. |
| 5,922,754 A | 7/1999 | Burchett et al. |
| 5,948,750 A | 9/1999 | Garsky et al. |
| 5,948,888 A | 9/1999 | de la Monte et al. |
| 5,955,444 A | 9/1999 | Ingram et al. |
| 5,962,266 A | 10/1999 | White et al. |
| 5,981,564 A | 11/1999 | Page et al. |
| 6,093,692 A | 7/2000 | Shen et al. |
| 6,126,965 A | 10/2000 | Kasid et al. |
| 6,191,290 B1 | 2/2001 | Safavy |
| 6,245,359 B1 | 6/2001 | Milstein et al. |
| 6,306,993 B1 | 10/2001 | Rothbard et al. |
| 6,316,024 B1 | 11/2001 | Allen et al. |
| 6,348,207 B1 | 2/2002 | Milstein et al. |
| 6,376,648 B2 | 4/2002 | White et al. |
| 6,391,305 B1 | 5/2002 | Feng et al. |
| 6,391,913 B1 | 5/2002 | Page et al. |
| 6,475,481 B2 | 11/2002 | Talmadge |

(Continued)

FOREIGN PATENT DOCUMENTS

| | | |
|---|---|---|
| CA | 2283474 A1 | 9/1998 |
| CA | 2525236 A1 | 1/2005 |

(Continued)

OTHER PUBLICATIONS

UICC (retrieved from http://www.uicc.org/programmes/childhood-cancer on Jun. 30, 2015, 1 page).*

Knapton S. (retrieved from http://www.telegraph.co.uk/science/2016/03/15/lets-stop-trying-to-cure-cancer-says-cancer-professor/ on Jul. 27, 2016, 14 pages).*

(Continued)

*Primary Examiner* — Karlheinz R Skowronek
*Assistant Examiner* — Ronald Niebauer
(74) *Attorney, Agent, or Firm* — Clark & Elbing LLP; Kristina Bieker-Brady

(57) ABSTRACT

The present invention relates to carriers, conjugate and pharmaceutical compositions and their use to increase the potency of drugs and to modify the pharmacokinetics of compounds. More particularly, the present invention relates to conjugates comprising the carrier described herein and their use in the treatment and diagnostic of cancer.

19 Claims, 31 Drawing Sheets

(56) References Cited

U.S. PATENT DOCUMENTS

| | | |
|---|---|---|
| 6,475,781 B1 | 11/2002 | Mercola et al. |
| 6,495,513 B1 | 12/2002 | Rueger et al. |
| 6,613,890 B2 | 9/2003 | White et al. |
| 6,660,525 B2 | 12/2003 | Martin et al. |
| 6,713,454 B1 | 3/2004 | Ekwuribe et al. |
| 6,906,033 B2 | 6/2005 | White et al. |
| 6,930,090 B2 | 8/2005 | Ekwuribe et al. |
| 7,019,123 B2 | 3/2006 | Tamburini et al. |
| 7,049,058 B2 | 5/2006 | Singh |
| 7,115,707 B2 | 10/2006 | Ben-Sasson et al. |
| 7,153,946 B2 | 12/2006 | McChesney et al. |
| 7,192,921 B2 | 3/2007 | Laakkonen et al. |
| 7,208,174 B2 | 4/2007 | Huwyler et al. |
| 7,214,657 B2 | 5/2007 | Kream |
| 7,557,182 B2 | 7/2009 | Beliveau et al. |
| 7,569,544 B2 | 8/2009 | Zankel et al. |
| 7,700,554 B2 | 4/2010 | Beliveau et al. |
| 7,902,156 B2 | 3/2011 | Béliveau et al. |
| 8,530,429 B2 | 9/2013 | Robbins et al. |
| 8,828,925 B2* | 9/2014 | Demeule ............... A61K 31/04 514/1.3 |
| 9,173,891 B2* | 11/2015 | Castaigne ............ A61K 31/337 |
| 2002/0013260 A1* | 1/2002 | Jia ....................... A61K 31/135 514/171 |
| 2002/0156124 A1 | 10/2002 | Gao et al. |
| 2003/0129186 A1 | 7/2003 | Beliveau et al. |
| 2003/0220391 A1 | 11/2003 | Bogardus et al. |
| 2004/0077540 A1 | 4/2004 | Quay |
| 2004/0087499 A1 | 5/2004 | Laakkonen et al. |
| 2004/0101904 A1 | 5/2004 | Pardridge et al. |
| 2004/0102369 A1 | 5/2004 | Wu et al. |
| 2004/0146549 A1 | 7/2004 | Ben-Sasson et al. |
| 2004/0220132 A1 | 11/2004 | Kaemmerer |
| 2004/0241174 A1 | 12/2004 | Amphlett et al. |
| 2005/0026823 A1 | 2/2005 | Zankel et al. |
| 2005/0042227 A1 | 2/2005 | Zankel et al. |
| 2005/0058702 A1 | 3/2005 | Ben-Sasson et al. |
| 2005/0100986 A1 | 5/2005 | Verma et al. |
| 2005/0178395 A1 | 8/2005 | Hunter et al. |
| 2005/0183731 A1 | 8/2005 | Hunter et al. |
| 2006/0019347 A1 | 1/2006 | Cho et al. |
| 2006/0029609 A1 | 2/2006 | Zankel et al. |
| 2006/0182684 A1 | 8/2006 | Beliveau |
| 2006/0189515 A1 | 8/2006 | Beliveau et al. |
| 2006/0251713 A1 | 11/2006 | Ben-Sasson et al. |
| 2007/0149444 A1 | 6/2007 | Laakkonen et al. |
| 2007/0167365 A1 | 7/2007 | Beliveau et al. |
| 2007/0172462 A1 | 7/2007 | Bohn et al. |
| 2007/0197460 A1 | 8/2007 | Fougerolles et al. |
| 2008/0199436 A1 | 8/2008 | Sawada |
| 2008/0213185 A1 | 9/2008 | Hong et al. |
| 2008/0299039 A1 | 12/2008 | Beliveau et al. |
| 2009/0016959 A1 | 1/2009 | Beliveau et al. |
| 2009/0082277 A1 | 3/2009 | Beliveau et al. |
| 2009/0215883 A1 | 8/2009 | Bouzada et al. |
| 2009/0221477 A1 | 9/2009 | Artymiuk et al. |
| 2009/0246211 A1 | 10/2009 | Henri et al. |
| 2010/0209429 A1 | 8/2010 | Erlich et al. |
| 2010/0256055 A1 | 10/2010 | Castaigne et al. |
| 2010/0284921 A1 | 11/2010 | Gordon et al. |
| 2010/0297120 A1 | 11/2010 | Beliveau et al. |
| 2011/0039785 A1 | 2/2011 | Beliveau et al. |
| 2011/0171128 A1 | 7/2011 | Beliveau et al. |
| 2011/0218152 A1 | 9/2011 | Beliveau et al. |
| 2011/0305750 A1 | 12/2011 | Beliveau et al. |
| 2012/0015876 A1 | 1/2012 | Castaigne et al. |
| 2012/0245169 A1 | 9/2012 | Ren et al. |
| 2014/0355163 A1 | 12/2014 | Chung |
| 2015/0037311 A1 | 2/2015 | Boivin et al. |

FOREIGN PATENT DOCUMENTS

| | | |
|---|---|---|
| CA | 2637893 A1 | 7/2007 |
| CA | 2638034 A1 | 7/2007 |
| DE | 19953696 A1 | 5/2001 |
| EP | 0393431 A1 | 10/1990 |
| EP | 1982699 A1 | 10/2008 |
| JP | H10-236984 A | 9/1998 |
| WO | WO-87/05702 A1 | 9/1987 |
| WO | WO-96/31531 A2 | 10/1996 |
| WO | WO-96/35788 A1 | 11/1996 |
| WO | WO-96/39160 A1 | 12/1996 |
| WO | WO-96/39183 A1 | 12/1996 |
| WO | WO-96/40210 A1 | 12/1996 |
| WO | WO-97/33996 A2 | 9/1997 |
| WO | WO-97/40160 A1 | 10/1997 |
| WO | WO-97/40854 A2 | 11/1997 |
| WO | WO-00/01417 A1 | 1/2000 |
| WO | WO-01/30319 A1 | 5/2001 |
| WO | WO-02/33090 A2 | 4/2002 |
| WO | WO-02/43765 A2 | 6/2002 |
| WO | WO-02/085923 A2 | 10/2002 |
| WO | WO-03/009815 A2 | 2/2003 |
| WO | WO-2004/060403 A2 | 7/2004 |
| WO | WO-2004/093897 A1 | 11/2004 |
| WO | WO-2004/108071 A2 | 12/2004 |
| WO | WO-2005/002515 A2 | 1/2005 |
| WO | WO-2005/014625 A1 | 2/2005 |
| WO | WO-2005/021579 A2 | 3/2005 |
| WO | WO-2005/042029 A2 | 5/2005 |
| WO | WO-2006/086870 A1 | 8/2006 |
| WO | WO-2006/089290 A1 | 8/2006 |
| WO | WO-2006/138343 A2 | 12/2006 |
| WO | WO-2007/009229 A1 | 1/2007 |
| WO | WO-2007/020085 A2 | 2/2007 |
| WO | WO-2007/030619 A2 | 3/2007 |
| WO | WO-2007/035716 A2 | 3/2007 |
| WO | WO-2007/044323 A2 | 4/2007 |
| WO | WO-2007/082978 A1 | 7/2007 |
| WO | WO-2007/082979 A1 | 7/2007 |
| WO | WO-2008/012629 A2 | 1/2008 |
| WO | WO-2008/036682 A2 | 3/2008 |
| WO | WO-2008/046228 A1 | 4/2008 |
| WO | WO-2008/144919 A1 | 12/2008 |
| WO | WO-2009/039188 A1 | 3/2009 |
| WO | WO-2009/070597 A2 | 6/2009 |
| WO | WO-2009/079790 A1 | 7/2009 |
| WO | WO-2009/105671 A2 | 8/2009 |
| WO | WO-2009/127072 A1 | 10/2009 |
| WO | WO-2010/043047 A1 | 4/2010 |
| WO | WO-2010/043049 A1 | 4/2010 |
| WO | WO-2010/063122 A1 | 6/2010 |
| WO | WO-2010/063123 A1 | 6/2010 |
| WO | WO-2010/063124 A1 | 6/2010 |
| WO | WO-2010/069074 A1 | 6/2010 |
| WO | WO-2010/121379 A1 | 10/2010 |
| WO | WO-2010/142035 A1 | 12/2010 |
| WO | WO-2011/000095 A1 | 1/2011 |
| WO | WO-2011/008823 A2 | 1/2011 |
| WO | WO-2011/041897 A1 | 4/2011 |
| WO | WO-2011/153642 A1 | 12/2011 |
| WO | WO-2012/000118 A1 | 1/2012 |
| WO | WO-2012/037687 A1 | 3/2012 |
| WO | WO-2012/068531 A2 | 5/2012 |
| WO | WO-2013/056096 A1 | 4/2013 |
| WO | WO-2013/078562 A2 | 6/2013 |
| WO | WO-2013/078564 A2 | 6/2013 |
| WO | WO-2013/185235 A1 | 12/2013 |
| WO | WO-2014/026283 A1 | 2/2014 |
| WO | WO-2014/026286 A1 | 2/2014 |
| WO | WO-2014/071531 A1 | 5/2014 |
| WO | WO-2014/076655 A1 | 5/2014 |
| WO | WO-2014/082184 A1 | 6/2014 |
| WO | WO-2014/194428 A1 | 12/2014 |
| WO | WO-2014/194429 A1 | 12/2014 |

OTHER PUBLICATIONS

Word Press (retrieved from https://chewychunks.wordpress.com/2015/01/30/why-two-thirds-of-cancer-cases-are-not-preventable/ on Jun. 30, 2015, 4 pages).*

(56) References Cited

OTHER PUBLICATIONS

Home Vet (retrieved from http://www.homevet.com/pet-care-library/item/382-what-are-the-signs-of-cancer-in-pets on Jun. 30, 2015, 3 pages).*
Kaldas Center (retrieved from http://kaldascenter.com/media/Kaldas-Center-Breast-Cancer.pdf on Jun. 30, 2015, 1 page).*
Xin et al., "The brain targeting mechanism of Angiopep-conjugated poly(ethylene glycol)-co-poly(epsilon-caprolactone) nanoparticles," Biomaterials. 33(5):1673-81 (2012).
Shao et al., "Angiopep-2 modified PE-PEG based polymeric micelles for amphotericin B delivery targeted to the brain," J Control Release. 147(1):118-26 (2010).
Wood et al., "A family of hierarchically self-assembling linear-dendritic hybrid polymers for highly efficient targeted gene delivery" Angew Chem Int Ed Engl. 44(41):6704-8 (2005).
Nagy et al., "Cytotoxic analogs of luteinizing hormone-releasing hormone containing doxorubicin or 2-pyrrolinodoxorubicin, a derivative 500-1000 times more potent," Proc Natl Acad Sci U S A. 93(14):7269-73 (1996).
Arseneault et al., "Synthesis of a controlled three-faced Pamam particle," Polym Chem 2:2293-8 (2011).
Huang et al., "Dual targeting effect of Angiopep-2-modified, DNA-loaded nanoparticles for glioma," Biomaterials. 32:6832-8 (2011).
Liu et al., "Versatile synthesis of asymmetrical dendron-like/dendron-like poly(epsilon-caprolactone)-b-poly(gamma-benzyl-L-glutamate) block copolymers," Dendritic Polymers. 49(16):3491-8 (2011).
Yan et al., "Imaging brain tumor by dendrimer-based optical/paramagnetic nanoprobe across the blood-brain barrier," Chem Commun. 47:8130-2 (2011).
U.S. Appl. No. 61/138,375, filed Dec. 2008, Beliveau et al.
U.S. Appl. No. 61/546,851, filed Oct. 13, 2011, Demuele et al.
Akhtar et al., "Nonviral delivery of synthetic siRNAs in vivo," J Clin Invest. 117(12):3623-32 (2007).
Anonymous, "Blood-Brain Barrier Tackled," <http://www.ecancermedicalscience.com/news-insider-news.asp?itemId-326>, published Oct. 22, 2008 (2 pages).
Arpicco et al., "New coupling reagents for the preparation of disulfide cross-linked conjugates with increased stability," Bioconjug Chem. 8(3):327-37 (1997).
Ballabh et al., "The blood-brain barrier: an overview structure, regulation, and clinical implications," Neurobiol Dis. 16:1-13 (2004).
Banks, "Leptin transport across the blood-brain barrier: implications for the cause and treatment of obesity," Curr Pharm Des. 7(2):125-33 (2001).
Banks, "The blood-brain barrier as a cause of obesity," Curr Pharm Des. 14(16):1606-14 (2008).
Bertrand et al., "Transport characteristics of a novel peptide platform for CNS therapeutics," J Cell Mol Med. 14(12):2827-39 (2010).
Bicamumpaka et al., "In vitro cytotoxicity of paclitaxel-transferrin conjugate on H69 cells," Oncol Rep. 5(6):1381-3 (1998).
Bickel et al., "Delivery of peptides and proteins through the blood-brain barrier," Adv Drug Deliv Rev. 46:247-279 (2001).
Boado, "Blood-brain barrier transport of non-viral gene and RNAi therapeutics," Pharm Res. 24(9):1772-87 (2007).
Bork et al., "Go hunting in sequence databases but watch out for the traps," Trends Genet. 12:425-427 (1996).
Bork, "Powers and pitfalls in sequence analysis: the 70% hurdle," Genome Res. 10:398-400 (2000).
Boules et al., "Bioactive analogs of neurotensin: focus on CNS effects," Peptides. 27(10):2523-33 (2006).
Brenner, "Errors in genome annotation," Trends Genet. 15(4):132-3 (1999).
Castex et al., "2-Pyrrolinodoxorubicin and its peptide-vectorized form bypass multidrug resistance," Anticancer Drugs. 15(6):609-617 (2004).
Chari, R., "Targeted Cancer Therapy: Conferring Specifcity to Cytotoxic Drugs," Acc. Chem. Res. 41:98-107 (2008).
Chen et al., "Synthesis of doxorubicin conjugates through hydrazone bonds to melanotransferrin P97," Synth Commun. 33(14):2377-2390 (2003).
Cho et al., "An unnatural biopolymer," Science. 261(5126):1303-1305 (1993).
Ché et al., "New Angiopep-modified doxorubicin (ANG1007) and etoposide (ANG 1009) chemotherapeutics with increased brain penetration" J Med Chem. 53(7):2814-24 (2010).
Coon et al., "Solutol HS 15, nontoxic polyoxyethylene esters of 12-hydroxystearic acid, reverses multidrug resistance," Cancer Res. 51:897-902 (1991).
Cui et al., "PAMAM-drug complex for delivering anticancer drug across blood-brain barrier in-vitro and in-vivo," Afr J Pharm Pharmacol. 3(5):227-233 (2009).
D'Onofrio et al., "Glycomimetics as decorating motifs for oligonucleotides: solid-phase synthesis, stability, and hybridization properties of carbopeptoid-oligonucleotide conjugates," Bioconjug Chem. 16:1299-1309 (2005).
Dagenais et al., "Development of an in situ mouse brain perfusion model and its application to mdr1a P-glycoprotein-deficient mice," J Cereb Blood Flow Metab. 20:381-386 (2000).
Deane et al., "LRP/Amyloid β-Peptide interaction mediates differential brain efflux of Aβ isoforms," Neuron. 43:333-344 (2004).
Decision of Rejection with English Translation for Japanese Patent Application No. 2008-520685, mailed on Feb. 14, 2013 (8 pages).
Declaration of Michel Demeule in European Patent Application No. 11010125 dated Sep. 24, 2012 (4 pages).
Dehouck et al., "A new function for the LDL receptor: transcytosis of LDL across the blood-brain barrier," J Cell Biol. 138(4):877-889 (1997).
Dehouck et al., "An easier, reproducible, and mass-production method to study the blood-brain barrier in vitro," J Neurochem. 54(5):1798-1801 (1990).
Dehouck et al., "Drug transfer across the blood-brain barrier: correlation between in vitro and in vivo models," J Neurochem. 58(5):1790-1797 (1992).
Demeule et al., "ANG2002: A new Angiochem-modified neurotensin with increased brain penetration and analgesic properties," Program No. 374.11/QQ6 2010 Neuroscience Meeting Planner, San Diego, CA: Society for Neuroscience (2010) (5 pages).
Demeule et al., "Conjugation of a brain-penetrant peptide with neurotensin provides antinociceptive properties," J Clin Invest. 124(3):1199-1213 (2014) (15 pages).
Demeule et al., "Drug transport to the brain: key roles for the efflux pump P-glycoprotein in the blood-brain barrier," Vascul Pharmacol. 38(6):339-48 (2002).
Demeule et al., "High transcytosis of melanotransferrin (P97) across the blood-brain barrier," J Neurochem. 83:924-933 (2002).
Demeule et al., "Identification and design of peptides as a new drug delivery system for the brain," J Pharmacol Exp Ther. 324(3):1064-1072 (2008).
Demeule et al., "Involvement of the low-density lipoprotein receptor-related protein in the transcytosis of the brain delivery vector angiopep-2," J Neurochem. 106(4):1534-44 (2008).
Demeule et al., "Isolation of endothelial cells from brain, lung, and kidney: expression of the multidrug resistance P-Glycoprotein isoforms," Biochem Biophys Res Commun. 281:827-834 (2001).
Deng et al., "Selected cysteine residues in transmembrane domains of mu-opioid receptor are critical for effects of sulfhydryl reagents," J Pharm Exp Ther. 293(1):113-20 (2000).
Doerks et al., "Protein annotation: detective work for function prediction," Trends Genet. 14:248-250 (1998).
Dooley et al., "An all D-amino acid opioid peptide with central analgesic activity from a combinatorial library," Science. 266(5193):2019-22 (1994).
Eigenbrot et al., "X-ray structure of glial cell-derived neurotrophic factor at 1.9 a resolution and implications for receptor binding," Nat Struct Biol. 4(6):435-8 (1997).
Search Report for Chinese Application No. 200680033365.8, dated Sep. 28, 2012 (English translation included) (4 pages).
Extended European Search Report for European Patent Application No. 10006638.0, dated Sep. 13, 2010 (9 pages).

(56) References Cited

OTHER PUBLICATIONS

Extended European Search Report for European Patent Application No. 11010071.6, dated Sep. 14, 2012 (8 pages).
Extended European Search Report for European Patent Application No. 11010125.0, dated Feb. 15, 2012 (11 pages).
Extended Supplementary European Search Report for European Patent Application No. 06761127.7, dated Jul. 27, 2009 (12 pages).
Fillebeen et al., "Receptor-mediated transcytosis of lactoferrin through the blood-brain barrier," J Biol Chem. 274(11):7011-7017 (1999).
Fioretti et al., "Aprotinin-like isoinhibitors in bovine organs," Biol Chem Hoppe Seyler. 369 Suppl:37-42 (1988).
Fromm, "P-glycoprotein: a defense mechanism limiting oral bioavailability and CNS accumulation of drugs," Int J Clin Pharmacol Ther. 38:69-74 (2000).
Gabathuler, "Approaches to transport therapeutic drugs across the blood-brain barrier to treat brain diseases," Neurobiol Dis. 37(1):48-57 (2010).
Gabius et al., "Targeting of neoglycoprotein-drug conjugates to cultured human embryonal carcinoma cells," J Cancer Res Clin Oncol. 113(2):126-130 (1987).
Garsky et al., "The synthesis of a prodrug of doxorubicin designed to provide reduced systemic toxicity and greater target efficacy," J Med Chem. 44(24):4216-4224 (2001).
Gelmon, "The taxoids: paclitaxel and docetaxel," Lancet. 344:1267-1272 (1994).
Gewirtz, "A critical evaluation of the mechanisms of action proposed for the antitumor effects of the anthracycline antibiotics adriamycin and daunorubicin," Biochem Pharmacol. 57:727-741 (1999).
Gottschalk et al., "Protein self-association in solution: the bovine pancreatic trypsin inhibitor decamer," Biophys J. 84(6):3941-58 (2003).
Grabb et al., "Neoplastic and pharmacological influence on the permeability of an in vitro blood-brain barrier," J Neurosurg. 82(6):1053-1058 (1995).
Guillot et al., "Angiotensin peptide regulation of bovine brain microvessel endothelial cell monolayer permeability," J Cardiovasc Pharmacol. 18(2):212-218 (1991).
Gumbleton et al., "Progress and limitations in the use of in vitro cell cultures to serve as a permeability screen for the blood-brain barrier," J Pharm Sci. 90(11):1681-1698 (2001).
Harkavyi et al., "Glucagon-like peptide 1 receptor stimulation reverses key deficits in distinct rodent models of Parkinson's disease," J Neuroinflammation. 5:1-9 (2008).
Hawkins et al., "The blood-brain barrier/neurovascular unit in health and disease," Pharmacol Rev. 57(2):173-185 (2005).
Huang et al., "Targeting delivery of paclitaxel into tumor cells via somatostatin receptor endocytosis," Chem Biol. 7(7):453-61 (2000).
Hussain et al., "The mammalian low-density lipoprotein receptor family," Annu Rev Nutr. 19:141-172 (1999).
International Search Report and Written Opinion for International Application No. PCT/CA2005/001158, mailed Nov. 15, 2005 (9 pages).
International Search Report and Written Opinion for International Application No. PCT/CA2006/001165, dated Nov. 9, 2006 (17 pages).
Ito et al., "Functional characterization of the brain-to-blood efflux clearance of human amyloid-β peptide (1-40) across the rat blood-brain barrier," Neurosci Res. 56:246-252 (2006).
Jiang et al., "Tumor cell targeting of transferrin-PEG-TNF-alpha conjugate via a receptor-mediated delivery system: design, synthesis, and biological evaluation," Bioconjug Chem. 18(1):41-9 (2007).
Jodoin et al., "P-glycoprotein in blood-brain barrier endothelial cells: interaction and oligomerization with caveolins," J Neurochem. 87(4):1010-23 (2003).
Kalra, "Central leptin insufficiency syndrome: an interactive etiology for obesity, metabolic and neural diseases and for designing new therapeutic interventions," Peptides. 29(1):127-38 (2008).
Karyekar et al., "Zonula occludens toxin increases the permeability of molecular weight markers and chemotherapeutic agents across the bovine brain microvessel endothelial cells," J Pharm Sci. 92(2):414-23 (2003).
Ke et al., "Gene delivery targeted to the brain using an angiopep-conjugated polyethyleneglycol-modified polyamidoamine dendrimer," Biomaterials. 30(36):6976-85 (2009).
Kesari et al., "Phase II study of temozolomide, thalidomide, and celecoxib for newly diagnosed glioblastoma in adults," Neuro Oncol. 10(3):300-308 (2008).
Kiernan et al., "Fluorescent-labelled aprotinin: A new reagent for the histochemical detection of acid mucosubstances," Histochemie. 34(1): 77-84 (1973).
Kilic et al., "Intravenous TAT-GDNF is protective after focal cerebral ischemia in mice," Stroke. 34(5):1304-10 (2003).
Kirpotin et al., "Sterically stabilized anti-HER2 immunoliposomes: design and targeting to human breast cancer cells in vitro," Biochemistry. 36(1):66-75 (1997).
Kirsch et al., "Anti-angiogenic treatment strategies for malignant brain tumors," J Neurooncol. 50(1-2):149-63 (2000).
Kobayashi et al., "The protease inhibitor bikunin, a novel anti-metastatic agent," Biol Chem. 384:749-754 (2003).
Koo et al., "Differential expression of amyloid precursor protein mRNAs in cases of alzheimer's disease and in aged nonhuman primates," Neuron. 2:97-104 (1990).
Kounnas et al, "LDL receptor-related protein, a multifunctional ApoE receptor, binds secreted beta-amyloid precursor protein and mediates Its degradation," Cell. 82(2):331-340 (1995).
Koziara et al., "In situ blood-brain barrier transport of nanoparticles," Pharm Res. 20:1772-1778 (2003).
Kreuter et al., "Apolipoprotein-mediated transport of nanoparticle-bound drugs across the blood-brain barrier," J Drug Target. 10:317-325 (2002).
Kreuter et al., "Direct evidence that polysorbate-80-coated poly(Butylcyanoacrylate) nanoparticles deliver drugs to the CNS via specific mechanisms requiring prior binding of drug to the nanoparticles," Pharm Res. 20:409-416 (2003).
Kreuter, Nanoparticulate carriers for drug delivery to the brain. *Nanoparticles as Drug Carriers*. Torchilin VP, 527-547 (2006).
Kumar et al., "Transvascular delivery of small interfering RNA to the central nervous system," Nature. 448(7149):39-43 (2007).
Kurzrock et al., "ANG1005, an Angiopep-2/paclitaxel conjugate: The first clinical trial in patients with advanced cancer and brain metastases: Preliminary safety and tolerability data," 20th EORTC-NCI-AACR Symposium on "Molecular Targets and Cancer Therapeutics", Euro J of Cancer. 6(12):133, Abstract 424 (2008).
Kurzrock et al., "ANG1005: Results of a Phase I study in patients with advanced solid tumors and metastatic brain cancer," Poster 8168, ACCR/NCI/EORTC Annual Meeting (2009) (2 pages).
Laccabue et al., "A novel taxane active against an orthotopically growing human glioma xenograft," Cancer. 92:3085-3092 (2001).
Lachowicz et al., "Analgesic properties of a novel brain-penetrant Angiopep-2-neurotensin derivative (ANG2002) for treating chronic pain," Program No. 173.28/AA9 2012 Neuroscience Meeting Planner, New Orleans, LA: Society for Neuroscience (2012) (5 pages).
Lai et al., "The critical component to establish in vitro BBB model: pericyte," Brain Res Rev. 50(2):258-265 (2005).
Langer, "New methods of drug delivery," Science. 249(4976):1527-33 (1990).
Larionova et al., "Carbohydrate-containing derivatives of the trypsin-kallikrein inhibitor aprotinin from bovine organs II. inhibitor coupled to the (Carboxymethyl)dextran derivatives of D-galactose," Biol Chem Hoppe-Seyler. 366:743-748 (1985).
Larsson, "Megalin, an endocytic receptor with signalling potential," Acta Universitatis Upsaliensis Uppsala (58 pages) (2006).
Lewis et al., "Maleimidocysteineamido-DOTA derivatives: new reagents for radiometal chelate conjugation to antibody sulfhydryl groups undergo pH-dependent cleavage reactions," Bioconjug Chem. 9(1):72-86 (1998).
Li et al., "Expression of alpha2-macroglobulin receptor/low density lipoprotein receptor-related protein on surfaces of tumour cells: a study using flow cytometry," Cancer Lett. 111(1-2):199-205 (1997).

(56) References Cited

OTHER PUBLICATIONS

Ma et al., "Cationic charge-dependent hepatic delivery of amidated serum albumin," J Control Release. 102(3):583-594 (2005).
Marinò et al., "Megalin-mediated transcytosis of thyroglobulin by thyroid cells is a calmodulin-dependent process," Thyroid. 10(6):461-469 (2000).
Marinò et al., "Transcytosis of retinol-binding protein across renal proximal tubule cells after megalin (gp 330)-mediated endocytosis," J Am Soc Nephrol. 12:637-648 (2001).
Markman et al., "Phase II trial of weekly single-agent paclitaxel in platinum/paclitaxel-refractory ovarian cancer," J Clin Oncol. 20(9):2365-9 (2002).
Martel et al., "Transport of apolipoproteins E and J at the blood-brain barrier relevance to Alzheimer's disease," S.T.P. Pharma Sciences. 7(1):28-36 (1997).
Mazel et al., "Doxorubicin-peptide conjugates overcome multidrug resistance," Anticancer Drugs. 12(2):107-116 (2001).
McCarty, "Cell biology of the neurovascular unit: implications for drug delivery across the blood-brain barrier," Assay Drug Dev Technol. 3(1):89-95 (2005).
Michaud et al., "Risks and benefits of taxanes in breast and ovarian cancer," Drug Saf. 23(5):401-28 (2000).
Moestrup et al., "Evidence that epithelial glycoprotein 330/Megalin mediates uptake of polybasic drugs," J Clin Invest. 96(3):1404-1413 (1995).
Moore et al., "The role of flexible tethers in multiple ligand-receptor bond formation between curved surfaces," Biophys J. 91(5):1675-1687 (2006).
Muratovska et al., "Conjugate for efficient delivery of short interfering RNA (siRNA) into mammalian cells," FEBS Lett. 558:63-68 (2004).
Nagy et al., "Design, synthesis, and in vitro evaluation of cytotoxic analogs of bombesin-like peptides containing doxorubicin or its intensely potent derivative, 2-pyrrolinodoxorubicin," Proc Natl Acad Sci USA. 94(2):652-6 (1997).
Ngo et al., "Computational complexity: protein structure prediction, and the levinthal paradox," The Protein Folding Problem and Tertiary Structure Prediction Merz, Jr. and Le Grand, Eds. 491-495 (1994).
Niola et al., "A plasmid-encoded VEGF siRNA reduces glioblastoma angiogenesis and its combination with interleukin-4 blocks tumor growth in a xenograft mouse model," Cancer Biol Ther. 5(2):174-179 (2006).
Notice of Reasons for Rejection for Japanese Patent Application No. 2012-230853, dated Feb. 5, 2014 (9 pages).
Oldendorf, "Stereospecificity of blood-brain barrier permeability to amino acids," Am J Physiol. 224(4):967-9 (1973).
Orlando et al., "Identification of the second cluster of ligand-binding repeats in megalin as a site for receptor-ligand interactions," Proc Natl Acad Sci USA. 94(6):2368-2373 (1997).
Pan et al., "Efficient transfer of receptor-associated protein (RAP) across the blood-brain barrier," J Cell Sci. 117(21):5071-5078 (2004).
Pardridge et al. "Combined use of carboxyl-directed protein pegylation and vector-mediated blood-brain barrier drug delivery system optimizes brain uptake of brain-derived neurotrophic factor following intravenous administration," Pharm Res. 15(4):576-582 (1998).
Pardridge et al., "Selective transport of an anti-transferrin receptor antibody through the blood-brain barrier in vivo," J Pharmacol Exp Ther. 259(1):66-70 (1991).
Pardridge, "Blood-brain barrier biology and methodology," J Neurovirol. 5(6):556-569 (1999).
Pardridge, "CNS drug design based on principles of blood-brain barrier transport," J Neurochem. 70(5):1781-1792 (1998).
Pardridge, "Drug targeting to the brain," Pharm Res. 24(9):1733-1744 (2007).
Pardridge, "Vector-mediated drug delivery to the brain," Adv Drug Deliv Rev. 36(2-3):299-321 (1999).

Pathan et al. "CNS drug delivery systems: novel approaches," Recent Pat Drug Deliv Formul. 3(1):71-89 (2009).
Peri et al., "D-Glucose as a regioselectively addressable scaffold for combinatorial chemistry on solid phase," J Carbohydr Chem. 22(1):57-71 (2003).
Powell et al., "Peptide stability in drug development. II. Effect of single amino acid substitution and glycosylation on peptide reactivity in human serum," Pharm Res. 10(9):1268-73 (1993).
Prince et al., "Lipoprotein receptor binding, cellular uptake, and lysosomal delivery of fusions between the receptor-associated protein (RAP) and alpha-L-Iduronidase or Acid alpha-Glucosidase," J Biol Chem. 279(33):35037-35046 (2004).
Qu et al., "Carbohydrate-based micelle clusters which enhance hydrophobic drug bioavailability by up to 1 order of magnitude," Biomacromolecules. 7:3452-3459 (2006).
Ramakrishnan, "The role of P-glycoprotein in the blood-brain barrier," Einstein Q J Biol Med. 19:160-165 (2003).
Rawat et al., "Lipid carriers: a versatile delivery vehicle for proteins and peptides," Yakugaku Zasshi. 128(2):269-280 (2008).
Rousselle et al., "New Advances in the Transport of Doxorubicin through the Blood-Brain Barrier by a Peptide Vector-Mediated Strategy," Mol. Pharmacol. 57:679-686 (2000).
Rudikoff et al., "Single amino acid substitution altering antigen-binding specificity," Proc Natl Acad Sci USA. 79(6):1979-83 (1982).
Régina et al., "Differences in multidrug resistance phenotype and matrix metalloproteinases activity between endothelial cells from normal brain and glioma," J Neurochem. 84:316-324 (2003).
Sadeghi-aliabadi et al., "Solvent optimization on Taxol extraction from Taxus baccata L., using HPLC and LC-MS," DARU. 17(3):192-8 (2009).
Saito et al., "Drug delivery strategy utilizing conjugation via reversible disulfide linkages: role and site of cellular reducing activities," Adv Drug Deilv Rev. 55(2):199-215 (2003).
Samson et al., "Gene therapy for diabetes: metabolic effects of helper-dependent adenoviral exendin 4 expression in a diet-induced obesity mouse model," Mol Ther. 16(11):1805-12 (2008).
Scherrmann, "Drug delivery to brain via the blood-brain barrier," Vascul Pharmacol. 38(6):349-354 (2002).
Schiff et al., "Taxol stabilizes microtubules in mouse fibroblast cells," Proc Natl Acad Sci USA. 77(3):1561-5 (1980).
Schinkel, "P-Glycoprotein, a gatekeeper in the blood-brain barrier," Adv Drug Deliv Rev. 36(2-3):179-194 (1999).
Seidel et al., "Effects of trasylol on the blood-brain barrier in rats," Naunyn-Schmiedebergs Arch Pharmacol. 284(4):R73 (Abstract Only) (1974).
Seiden et al., "A phase II study of the MDR inhibitor biricodar (INCEL, VX-710) and paclitaxel in women with advanced ovarian cancer refractory to paclitaxel therapy," Gynecol Oncol. 86(3):302-10 (2002).
Shibata et al., "Clearance of Alzheimer's amyloid-ss(1-40) peptide from brain by LDL receptor-related protein-1 at the blood-brain barrier," J Clin Invest. 106(12):1489-1499 (2000).
Shiiki et al., "Brain insulin impairs amyloid-beta(1-40) clearance from the brain," J Neurosci. 24(43):9632-9637 (2004).
Shimura et al., "Transport mechanism of a new behaviorally highly potent adrenocorticotropic hormone (ACTH) analog, ebiratide, through the blood-brain barrier," J Pharmacol Exp Ther. 258(2):459-465 (1991).
Skolnick et al., "From genes to protein structure and function: novel applications of computational approaches in the genomic era," Trends Biotechnol. 18:34-39 (2000).
Smith et al., "The challenges of genome sequence annotation or 'The devil is in the details'," Nat Biotechnol. 15:1222-1223 (1997).
Smith, "Brain perfusion systems for studies of drug uptake and metabolism in the central nervous system," Pharm Biotechnol. 8:285-307 (1996).
Steiniger et al., "Chemotherapy of glioblastoma in rats using doxorubicin-loaded nanoparticles," Int J Cancer. 109:759-767 (2004).
Takei et al., "A small interfering RNA targeting vascular endothelial growth factor as cancer therapeutics," Cancer Res. 64(10):3365-70 (2004).

(56) References Cited

OTHER PUBLICATIONS

Tamai et al., "Structure-internalization relationship for adsorptive-mediated endocytosis of basic peptides at the blood-brain barrier," J Pharmacol Exp Ther. 280(1):410-415 (1997).
Temsamani et al., "Vector-mediated drug delivery to the brain," Expert Opin Biol Ther. 1(5):773-782 (2001).
Terasaki et al., "New approaches to in vitro models of blood-brain barrier drug transport," Drug Discov Today. 8(20):944-954 (2003).
Trail et al., "Cure of xenografted human carcinomas by BR96-doxorubicin immunoconjugates," Science. 261(5118):212-215 (1993).
Triguero et al., "Capillary depletion method for quantification of blood-brain barrier transport of circulating peptides and plasma proteins," J Neurochem. 54(6):1882-1888 (1990).
Turner et al., "RNA targeting with peptide conjugates of oligonucleotides, siRNA and PNA," Blood Cells Mol Dis. 38:1-7 (2007).
Uekita et al. "Membrane-type 1 matrix metalloproteinase cytoplasmic tail-binding protein-1 is a new member of the Cupin superfamily. A possible multifunctional protein acting as an invasion suppressor down-regulated in tumors," J Biol Chem. 279(13):12734-12743 (2004).
Uekita et al., "Cytoplasmic tail-dependent internalization of membrane-type 1 matrix metalloproteinase is important for its invasion-promoting activity," J Cell Biol. 155(7):1345-1356 (2001).
Wang et al., "DNA/dendrimer complexes mediate gene transfer into murine cardiac transplants ex Vivo," Mol Ther. 2(8):602-608 (2000).
Wells, "Additivity of mutational effects in proteins," Biochemistry. 29(37):8509-8517 (1990).
Witt et al., "Peptide drug modifications to enhance bioavailability and blood-brain barrier permeability," Peptides. 22(12):2329-2343 (2001).
Xu et al., "In vitro and in vivo evaluation of actively targetable nanoparticles for paclitaxel delivery," Int J Pharm. 288:361-368 (2005).
Yepes et al., "Tissue-type plasminogen activator induces opening of the blood-brain barrier via the LDL receptor-related protein," J Clin Invest. 112(10):1533-1540 (2003).
Zhang et al. "In vitro gene delivery using polyamidoamine dendrimers with a trimesyl core," Biomacromolecules. 6(1):341-350 (2005).
Zhang et al., "Silencing the epidermal growth factor receptor gene with RNAi may be developed as a potential therapy for non small cell lung cancer," Genet Vaccines Ther. 3(5):1-12 (2005).
Zhang et al., "siRNA-containing liposomes modified with polyarginine effectively silence the targeted gene," J Control Release. 112:229-239 (2006).
Zhang et al., "Tat-modified leptin is more accessible to hypothalamus through brain-blood barrier with a significant inhibition of body-weight gain in high-fat-diet fed mice," Exp Clin Endocrinol Diabetes. 118(1):31-7 (2010).
Zlokovic et al., "Glycoprotein 330/Megalin: probable role in receptor-mediated transport of apolipoprotein J alone and in a complex with Alzheimer disease amyloid Beta at the blood-brain and blood cerebrospinal fluid barriers," Proc Natl Acad Sci U S A. 93:4229-4234 (1996).
Ziske et al., "Acute transient encephalopathy after paclitaxel infusion: report of three cases," Ann Oncol. 13(4):629-31 (2002).
Patel et al., "Getting into the brain: approaches to enhance brain drug delivery," CNS Drugs. 23(1):35-58 (2009).
Wei et al., "Retro-inverso isomer of Angiopep-2: a stable d-peptide ligand inspires brain-targeted drug delivery," Mol Pharm. 11(10):3261-3268 (2014) (8 pages).
Comereski et al., "BR96-doxorubicin conjugate (BMS-182248) versus doxorubicin: a comparative toxicity assessment in rats," Toxicol Pathol. 22(5):473-88 (1994).
Egger-Heigold, Barbara, Thesis: "The effect of excipients on pharmacokinetic parameters of parenteral drugs," Doctorate, University of Basel, 2005.
Gaillard et al., "Targeted delivery across the blood-brain barrier," Expert Opin Drug Deliv. 2(2):299-309 (2005).
Régina et al., "Antitumour activity of ANG1005, a conjugate between paclitaxel and the new brain delivery vector Angiopep-2," Br J Pharmacol. 155(2):185-97 (2008).
Mazza et al., "Cancer and the blood-brain barrier: 'Trojan horses' for courses?" Br J Pharmacol. 155(2):149-51 (2008).
Castaigne et al., "425 Poster ANG1005: Preliminary clinical safety and tolerability in patients with recurrent malignant glioma," Eur J Cancer. 6(12):133-134 (2008).
Kurzrock et al., "424 Poster ANG1005, an Angiopep-2/paclitaxel conjugate: the first clinical trial in patients with advanced cancer and brain metastases: Preliminary safety and tolerability data," Eur J Cancer. 6(12):133 (2008).
Gabathuler et al., "117 Poster ANG1005, Paclitaxel conjugated to the angiopep brain transport vector for the treatment of brain cancer: preclinical studies," Eur J Cancer. 6(12):38-9 (2008).
Gabathuler et al., "147 Poster a new Taxol delivery system for the treatment of brain primary or metastatic tumors," Eur J Cancer. 4(12):47-8 (2006).

\* cited by examiner

Fig. 1

Angiopep-1 vs Angiopep-2

Angiopep-1:     TFFYGGCRGKRNNFKTEEY

Angiopep-2:     TFFYGGSRGKRNNFKTEEY

[TxlAn2 (3:1)]

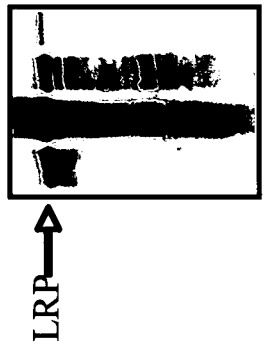
Fig. 16A Primary brain tumors
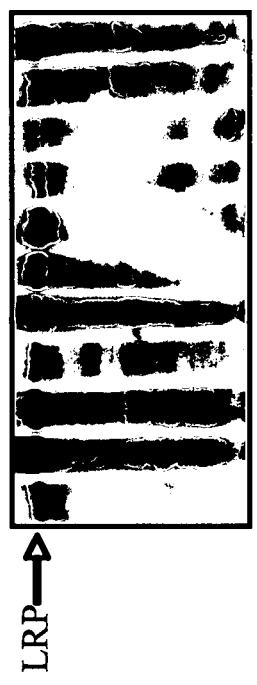
Fig. 16B Brain metastasis from

SEQUENCE LISTING

```
<160> NUMBER OF SEQ ID NOS: 112

<210> SEQ ID NO 1
<211> LENGTH: 19
<212> TYPE: PRT
<213> ORGANISM: Artificial Sequence
<220> FEATURE:
<223> OTHER INFORMATION: synthetic

<400> SEQUENCE: 1

Thr Phe Val Tyr Gly Gly Cys Arg Ala Lys Arg Asn Asn Phe Lys Ser
1               5                   10                  15

Ala Glu Asp

<210> SEQ ID NO 2
<211> LENGTH: 19
<212> TYPE: PRT
<213> ORGANISM: Artificial Sequence
<220> FEATURE:
<223> OTHER INFORMATION: synthetic

<400> SEQUENCE: 2

Thr Phe Gln Tyr Gly Gly Cys Met Gly Asn Gly Asn Asn Phe Val Thr
1               5                   10                  15

Glu Lys Glu

<210> SEQ ID NO 3
<211> LENGTH: 19
<212> TYPE: PRT
<213> ORGANISM: Artificial Sequence
<220> FEATURE:
<223> OTHER INFORMATION: synthetic

<400> SEQUENCE: 3

Pro Phe Phe Tyr Gly Gly Cys Gly Gly Asn Arg Asn Asn Phe Asp Thr
1               5                   10                  15

Glu Glu Tyr

<210> SEQ ID NO 4
<211> LENGTH: 19
<212> TYPE: PRT
<213> ORGANISM: Artificial Sequence
<220> FEATURE:
<223> OTHER INFORMATION: synthetic

<400> SEQUENCE: 4

Ser Phe Tyr Tyr Gly Gly Cys Leu Gly Asn Lys Asn Asn Tyr Leu Arg
1               5                   10                  15
```

Glu Glu Glu

<210> SEQ ID NO 5
<211> LENGTH: 19
<212> TYPE: PRT
<213> ORGANISM: Artificial Sequence
<220> FEATURE:
<223> OTHER INFORMATION: synthetic

<400> SEQUENCE: 5

Thr Phe Phe Tyr Gly Gly Cys Arg Ala Lys Arg Asn Asn Phe Lys Arg
1               5                   10                  15

Ala Lys Tyr

<210> SEQ ID NO 6
<211> LENGTH: 19
<212> TYPE: PRT
<213> ORGANISM: Artificial Sequence
<220> FEATURE:
<223> OTHER INFORMATION: synthetic

<400> SEQUENCE: 6

Thr Phe Phe Tyr Gly Gly Cys Arg Gly Lys Arg Asn Asn Phe Lys Arg
1               5                   10                  15

Ala Lys Tyr

<210> SEQ ID NO 7
<211> LENGTH: 19
<212> TYPE: PRT
<213> ORGANISM: Artificial Sequence
<220> FEATURE:
<223> OTHER INFORMATION: synthetic

<400> SEQUENCE: 7

Thr Phe Phe Tyr Gly Gly Cys Arg Ala Lys Lys Asn Asn Tyr Lys Arg
1               5                   10                  15

Ala Lys Tyr

<210> SEQ ID NO 8
<211> LENGTH: 19
<212> TYPE: PRT
<213> ORGANISM: Artificial Sequence
<220> FEATURE:
<223> OTHER INFORMATION: synthetic

<400> SEQUENCE: 8

Thr Phe Phe Tyr Gly Gly Cys Arg Gly Lys Lys Asn Asn Phe Lys Arg
1               5                   10                  15

Ala Lys Tyr

<210> SEQ ID NO 9
<211> LENGTH: 19
<212> TYPE: PRT
<213> ORGANISM: Artificial Sequence
<220> FEATURE:
<223> OTHER INFORMATION: synthetic

<400> SEQUENCE: 9

Thr Phe Gln Tyr Gly Gly Cys Arg Ala Lys Arg Asn Asn Phe Lys Arg
1               5                   10                  15

Ala Lys Tyr

-continued

```
<210> SEQ ID NO 10
<211> LENGTH: 19
<212> TYPE: PRT
<213> ORGANISM: Artificial Sequence
<220> FEATURE:
<223> OTHER INFORMATION: synthetic

<400> SEQUENCE: 10

Thr Phe Gln Tyr Gly Gly Cys Arg Gly Lys Lys Asn Asn Phe Lys Arg
1               5                   10                  15

Ala Lys Tyr

<210> SEQ ID NO 11
<211> LENGTH: 19
<212> TYPE: PRT
<213> ORGANISM: Artificial Sequence
<220> FEATURE:
<223> OTHER INFORMATION: synthetic

<400> SEQUENCE: 11

Thr Phe Phe Tyr Gly Gly Cys Leu Gly Lys Arg Asn Asn Phe Lys Arg
1               5                   10                  15

Ala Lys Tyr

<210> SEQ ID NO 12
<211> LENGTH: 19
<212> TYPE: PRT
<213> ORGANISM: Artificial Sequence
<220> FEATURE:
<223> OTHER INFORMATION: synthetic

<400> SEQUENCE: 12

Thr Phe Phe Tyr Gly Gly Ser Leu Gly Lys Arg Asn Asn Phe Lys Arg
1               5                   10                  15

Ala Lys Tyr

<210> SEQ ID NO 13
<211> LENGTH: 19
<212> TYPE: PRT
<213> ORGANISM: Artificial Sequence
<220> FEATURE:
<223> OTHER INFORMATION: synthetic

<400> SEQUENCE: 13

Pro Phe Phe Tyr Gly Gly Cys Gly Gly Lys Lys Asn Asn Phe Lys Arg
1               5                   10                  15

Ala Lys Tyr

<210> SEQ ID NO 14
<211> LENGTH: 19
<212> TYPE: PRT
<213> ORGANISM: Artificial Sequence
<220> FEATURE:
<223> OTHER INFORMATION: synthetic

<400> SEQUENCE: 14

Thr Phe Phe Tyr Gly Gly Cys Arg Gly Lys Gly Asn Asn Tyr Lys Arg
1               5                   10                  15

Ala Lys Tyr

<210> SEQ ID NO 15
<211> LENGTH: 19
<212> TYPE: PRT
<213> ORGANISM: Artificial Sequence
```

<220> FEATURE:
<223> OTHER INFORMATION: synthetic

<400> SEQUENCE: 15

Pro Phe Phe Tyr Gly Gly Cys Arg Gly Lys Arg Asn Asn Phe Leu Arg
1               5                   10                  15

Ala Lys Tyr

<210> SEQ ID NO 16
<211> LENGTH: 19
<212> TYPE: PRT
<213> ORGANISM: Artificial Sequence
<220> FEATURE:
<223> OTHER INFORMATION: synthetic

<400> SEQUENCE: 16

Thr Phe Phe Tyr Gly Gly Cys Arg Gly Lys Arg Asn Asn Phe Lys Arg
1               5                   10                  15

Glu Lys Tyr

<210> SEQ ID NO 17
<211> LENGTH: 19
<212> TYPE: PRT
<213> ORGANISM: Artificial Sequence
<220> FEATURE:
<223> OTHER INFORMATION: synthetic

<400> SEQUENCE: 17

Pro Phe Phe Tyr Gly Gly Cys Arg Ala Lys Lys Asn Asn Phe Lys Arg
1               5                   10                  15

Ala Lys Glu

<210> SEQ ID NO 18
<211> LENGTH: 19
<212> TYPE: PRT
<213> ORGANISM: Artificial Sequence
<220> FEATURE:
<223> OTHER INFORMATION: synthetic

<400> SEQUENCE: 18

Thr Phe Phe Tyr Gly Gly Cys Arg Gly Lys Arg Asn Asn Phe Lys Arg
1               5                   10                  15

Ala Lys Asp

<210> SEQ ID NO 19
<211> LENGTH: 19
<212> TYPE: PRT
<213> ORGANISM: Artificial Sequence
<220> FEATURE:
<223> OTHER INFORMATION: synthetic

<400> SEQUENCE: 19

Thr Phe Phe Tyr Gly Gly Cys Arg Ala Lys Arg Asn Asn Phe Asp Arg
1               5                   10                  15

Ala Lys Tyr

<210> SEQ ID NO 20
<211> LENGTH: 19
<212> TYPE: PRT
<213> ORGANISM: Artificial Sequence
<220> FEATURE:
<223> OTHER INFORMATION: synthetic

<400> SEQUENCE: 20

Thr Phe Phe Tyr Gly Gly Cys Arg Gly Lys Lys Asn Asn Phe Lys Arg
1               5                   10                  15

Ala Glu Tyr

<210> SEQ ID NO 21
<211> LENGTH: 19
<212> TYPE: PRT
<213> ORGANISM: Artificial Sequence
<220> FEATURE:
<223> OTHER INFORMATION: synthetic

<400> SEQUENCE: 21

Pro Phe Phe Tyr Gly Gly Cys Gly Ala Asn Arg Asn Asn Phe Lys Arg
1               5                   10                  15

Ala Lys Tyr

<210> SEQ ID NO 22
<211> LENGTH: 19
<212> TYPE: PRT
<213> ORGANISM: Artificial Sequence
<220> FEATURE:
<223> OTHER INFORMATION: synthetic

<400> SEQUENCE: 22

Thr Phe Phe Tyr Gly Gly Cys Gly Gly Lys Lys Asn Asn Phe Lys Thr
1               5                   10                  15

Ala Lys Tyr

<210> SEQ ID NO 23
<211> LENGTH: 19
<212> TYPE: PRT
<213> ORGANISM: Artificial Sequence
<220> FEATURE:
<223> OTHER INFORMATION: synthetic

<400> SEQUENCE: 23

Thr Phe Phe Tyr Gly Gly Cys Arg Gly Asn Arg Asn Asn Phe Leu Arg
1               5                   10                  15

Ala Lys Tyr

<210> SEQ ID NO 24
<211> LENGTH: 19
<212> TYPE: PRT
<213> ORGANISM: Artificial Sequence
<220> FEATURE:
<223> OTHER INFORMATION: synthetic

<400> SEQUENCE: 24

Thr Phe Phe Tyr Gly Gly Cys Arg Gly Asn Arg Asn Asn Phe Lys Thr
1               5                   10                  15

Ala Lys Tyr

<210> SEQ ID NO 25
<211> LENGTH: 19
<212> TYPE: PRT
<213> ORGANISM: Artificial Sequence
<220> FEATURE:
<223> OTHER INFORMATION: synthetic

<400> SEQUENCE: 25

Thr Phe Phe Tyr Gly Gly Ser Arg Gly Asn Arg Asn Asn Phe Lys Thr
1               5                   10                  15

Ala Lys Tyr

<210> SEQ ID NO 26
<211> LENGTH: 19
<212> TYPE: PRT
<213> ORGANISM: Artificial Sequence
<220> FEATURE:
<223> OTHER INFORMATION: synthetic

<400> SEQUENCE: 26

Thr Phe Phe Tyr Gly Gly Cys Leu Gly Asn Gly Asn Asn Phe Lys Arg
1               5                   10                  15

Ala Lys Tyr

<210> SEQ ID NO 27
<211> LENGTH: 19
<212> TYPE: PRT
<213> ORGANISM: Artificial Sequence
<220> FEATURE:
<223> OTHER INFORMATION: synthetic

<400> SEQUENCE: 27

Thr Phe Phe Tyr Gly Gly Cys Leu Gly Asn Arg Asn Asn Phe Leu Arg
1               5                   10                  15

Ala Lys Tyr

<210> SEQ ID NO 28
<211> LENGTH: 19
<212> TYPE: PRT
<213> ORGANISM: Artificial Sequence
<220> FEATURE:
<223> OTHER INFORMATION: synthetic

<400> SEQUENCE: 28

Thr Phe Phe Tyr Gly Gly Cys Leu Gly Asn Arg Asn Asn Phe Lys Thr
1               5                   10                  15

Ala Lys Tyr

<210> SEQ ID NO 29
<211> LENGTH: 19
<212> TYPE: PRT
<213> ORGANISM: Artificial Sequence
<220> FEATURE:
<223> OTHER INFORMATION: synthetic

<400> SEQUENCE: 29

Thr Phe Phe Tyr Gly Gly Cys Arg Gly Asn Gly Asn Asn Phe Lys Ser
1               5                   10                  15

Ala Lys Tyr

<210> SEQ ID NO 30
<211> LENGTH: 19
<212> TYPE: PRT
<213> ORGANISM: Artificial Sequence
<220> FEATURE:
<223> OTHER INFORMATION: synthetic

<400> SEQUENCE: 30

Thr Phe Phe Tyr Gly Gly Cys Arg Gly Lys Lys Asn Asn Phe Asp Arg
1               5                   10                  15

Glu Lys Tyr

<210> SEQ ID NO 31

```
<211> LENGTH: 19
<212> TYPE: PRT
<213> ORGANISM: Artificial Sequence
<220> FEATURE:
<223> OTHER INFORMATION: synthetic

<400> SEQUENCE: 31

Thr Phe Phe Tyr Gly Gly Cys Arg Gly Lys Arg Asn Asn Phe Leu Arg
1               5                   10                  15

Glu Lys Glu

<210> SEQ ID NO 32
<211> LENGTH: 19
<212> TYPE: PRT
<213> ORGANISM: Artificial Sequence
<220> FEATURE:
<223> OTHER INFORMATION: synthetic

<400> SEQUENCE: 32

Thr Phe Phe Tyr Gly Gly Cys Arg Gly Lys Gly Asn Asn Phe Asp Arg
1               5                   10                  15

Ala Lys Tyr

<210> SEQ ID NO 33
<211> LENGTH: 19
<212> TYPE: PRT
<213> ORGANISM: Artificial Sequence
<220> FEATURE:
<223> OTHER INFORMATION: synthetic

<400> SEQUENCE: 33

Thr Phe Phe Tyr Gly Gly Ser Arg Gly Lys Gly Asn Asn Phe Asp Arg
1               5                   10                  15

Ala Lys Tyr

<210> SEQ ID NO 34
<211> LENGTH: 19
<212> TYPE: PRT
<213> ORGANISM: Artificial Sequence
<220> FEATURE:
<223> OTHER INFORMATION: synthetic

<400> SEQUENCE: 34

Thr Phe Phe Tyr Gly Gly Cys Arg Gly Asn Gly Asn Asn Phe Val Thr
1               5                   10                  15

Ala Lys Tyr

<210> SEQ ID NO 35
<211> LENGTH: 19
<212> TYPE: PRT
<213> ORGANISM: Artificial Sequence
<220> FEATURE:
<223> OTHER INFORMATION: synthetic

<400> SEQUENCE: 35

Pro Phe Phe Tyr Gly Gly Cys Gly Gly Lys Gly Asn Asn Tyr Val Thr
1               5                   10                  15

Ala Lys Tyr

<210> SEQ ID NO 36
<211> LENGTH: 19
<212> TYPE: PRT
<213> ORGANISM: Artificial Sequence
<220> FEATURE:
```

<223> OTHER INFORMATION: synthetic

<400> SEQUENCE: 36

Thr Phe Phe Tyr Gly Gly Cys Leu Gly Lys Gly Asn Asn Phe Leu Thr
1               5                   10                  15

Ala Lys Tyr

<210> SEQ ID NO 37
<211> LENGTH: 19
<212> TYPE: PRT
<213> ORGANISM: Artificial Sequence
<220> FEATURE:
<223> OTHER INFORMATION: synthetic

<400> SEQUENCE: 37

Ser Phe Phe Tyr Gly Gly Cys Leu Gly Asn Lys Asn Asn Phe Leu Thr
1               5                   10                  15

Ala Lys Tyr

<210> SEQ ID NO 38
<211> LENGTH: 19
<212> TYPE: PRT
<213> ORGANISM: Artificial Sequence
<220> FEATURE:
<223> OTHER INFORMATION: synthetic

<400> SEQUENCE: 38

Thr Phe Phe Tyr Gly Gly Cys Gly Gly Asn Lys Asn Asn Phe Val Arg
1               5                   10                  15

Glu Lys Tyr

<210> SEQ ID NO 39
<211> LENGTH: 19
<212> TYPE: PRT
<213> ORGANISM: Artificial Sequence
<220> FEATURE:
<223> OTHER INFORMATION: synthetic

<400> SEQUENCE: 39

Thr Phe Phe Tyr Gly Gly Cys Met Gly Asn Lys Asn Asn Phe Val Arg
1               5                   10                  15

Glu Lys Tyr

<210> SEQ ID NO 40
<211> LENGTH: 19
<212> TYPE: PRT
<213> ORGANISM: Artificial Sequence
<220> FEATURE:
<223> OTHER INFORMATION: synthetic

<400> SEQUENCE: 40

Thr Phe Phe Tyr Gly Gly Ser Met Gly Asn Lys Asn Asn Phe Val Arg
1               5                   10                  15

Glu Lys Tyr

<210> SEQ ID NO 41
<211> LENGTH: 19
<212> TYPE: PRT
<213> ORGANISM: Artificial Sequence
<220> FEATURE:
<223> OTHER INFORMATION: synthetic

<400> SEQUENCE: 41

```
Pro Phe Phe Tyr Gly Gly Cys Leu Gly Asn Arg Asn Asn Tyr Val Arg
1               5                   10                  15

Glu Lys Tyr
```

<210> SEQ ID NO 42
<211> LENGTH: 19
<212> TYPE: PRT
<213> ORGANISM: Artificial Sequence
<220> FEATURE:
<223> OTHER INFORMATION: synthetic

<400> SEQUENCE: 42

```
Thr Phe Phe Tyr Gly Gly Cys Leu Gly Asn Arg Asn Asn Phe Val Arg
1               5                   10                  15

Glu Lys Tyr
```

<210> SEQ ID NO 43
<211> LENGTH: 19
<212> TYPE: PRT
<213> ORGANISM: Artificial Sequence
<220> FEATURE:
<223> OTHER INFORMATION: synthetic

<400> SEQUENCE: 43

```
Thr Phe Phe Tyr Gly Gly Cys Leu Gly Asn Lys Asn Asn Tyr Val Arg
1               5                   10                  15

Glu Lys Tyr
```

<210> SEQ ID NO 44
<211> LENGTH: 19
<212> TYPE: PRT
<213> ORGANISM: Artificial Sequence
<220> FEATURE:
<223> OTHER INFORMATION: synthetic

<400> SEQUENCE: 44

```
Thr Phe Phe Tyr Gly Gly Cys Gly Gly Asn Gly Asn Asn Phe Leu Thr
1               5                   10                  15

Ala Lys Tyr
```

<210> SEQ ID NO 45
<211> LENGTH: 19
<212> TYPE: PRT
<213> ORGANISM: Artificial Sequence
<220> FEATURE:
<223> OTHER INFORMATION: synthetic

<400> SEQUENCE: 45

```
Thr Phe Phe Tyr Gly Gly Cys Arg Gly Asn Arg Asn Asn Phe Leu Thr
1               5                   10                  15

Ala Glu Tyr
```

<210> SEQ ID NO 46
<211> LENGTH: 19
<212> TYPE: PRT
<213> ORGANISM: Artificial Sequence
<220> FEATURE:
<223> OTHER INFORMATION: synthetic

<400> SEQUENCE: 46

```
Thr Phe Phe Tyr Gly Gly Cys Arg Gly Asn Gly Asn Asn Phe Lys Ser
1               5                   10                  15

Ala Glu Tyr
```

<210> SEQ ID NO 47
<211> LENGTH: 19
<212> TYPE: PRT
<213> ORGANISM: Artificial Sequence
<220> FEATURE:
<223> OTHER INFORMATION: synthetic

<400> SEQUENCE: 47

Pro Phe Phe Tyr Gly Gly Cys Leu Gly Asn Lys Asn Asn Phe Lys Thr
1               5                   10                  15

Ala Glu Tyr

<210> SEQ ID NO 48
<211> LENGTH: 19
<212> TYPE: PRT
<213> ORGANISM: Artificial Sequence
<220> FEATURE:
<223> OTHER INFORMATION: synthetic

<400> SEQUENCE: 48

Thr Phe Phe Tyr Gly Gly Cys Arg Gly Asn Arg Asn Asn Phe Lys Thr
1               5                   10                  15

Glu Glu Tyr

<210> SEQ ID NO 49
<211> LENGTH: 19
<212> TYPE: PRT
<213> ORGANISM: Artificial Sequence
<220> FEATURE:
<223> OTHER INFORMATION: synthetic

<400> SEQUENCE: 49

Thr Phe Phe Tyr Gly Gly Cys Arg Gly Lys Arg Asn Asn Phe Lys Thr
1               5                   10                  15

Glu Glu Asp

<210> SEQ ID NO 50
<211> LENGTH: 19
<212> TYPE: PRT
<213> ORGANISM: Artificial Sequence
<220> FEATURE:
<223> OTHER INFORMATION: synthetic

<400> SEQUENCE: 50

Pro Phe Phe Tyr Gly Gly Cys Gly Gly Asn Gly Asn Asn Phe Val Arg
1               5                   10                  15

Glu Lys Tyr

<210> SEQ ID NO 51
<211> LENGTH: 19
<212> TYPE: PRT
<213> ORGANISM: Artificial Sequence
<220> FEATURE:
<223> OTHER INFORMATION: synthetic

<400> SEQUENCE: 51

Ser Phe Phe Tyr Gly Gly Cys Met Gly Asn Gly Asn Asn Phe Val Arg
1               5                   10                  15

Glu Lys Tyr

<210> SEQ ID NO 52
<211> LENGTH: 19

```
<212> TYPE: PRT
<213> ORGANISM: Artificial Sequence
<220> FEATURE:
<223> OTHER INFORMATION: synthetic

<400> SEQUENCE: 52

Pro Phe Phe Tyr Gly Gly Cys Gly Gly Asn Gly Asn Asn Phe Leu Arg
1               5                   10                  15

Glu Lys Tyr

<210> SEQ ID NO 53
<211> LENGTH: 19
<212> TYPE: PRT
<213> ORGANISM: Artificial Sequence
<220> FEATURE:
<223> OTHER INFORMATION: synthetic

<400> SEQUENCE: 53

Thr Phe Phe Tyr Gly Gly Cys Leu Gly Asn Gly Asn Asn Phe Val Arg
1               5                   10                  15

Glu Lys Tyr

<210> SEQ ID NO 54
<211> LENGTH: 19
<212> TYPE: PRT
<213> ORGANISM: Artificial Sequence
<220> FEATURE:
<223> OTHER INFORMATION: synthetic

<400> SEQUENCE: 54

Ser Phe Phe Tyr Gly Gly Cys Leu Gly Asn Gly Asn Asn Tyr Leu Arg
1               5                   10                  15

Glu Lys Tyr

<210> SEQ ID NO 55
<211> LENGTH: 19
<212> TYPE: PRT
<213> ORGANISM: Artificial Sequence
<220> FEATURE:
<223> OTHER INFORMATION: synthetic

<400> SEQUENCE: 55

Thr Phe Phe Tyr Gly Gly Ser Leu Gly Asn Gly Asn Asn Phe Val Arg
1               5                   10                  15

Glu Lys Tyr

<210> SEQ ID NO 56
<211> LENGTH: 19
<212> TYPE: PRT
<213> ORGANISM: Artificial Sequence
<220> FEATURE:
<223> OTHER INFORMATION: synthetic

<400> SEQUENCE: 56

Thr Phe Phe Tyr Gly Gly Cys Arg Gly Asn Gly Asn Asn Phe Val Thr
1               5                   10                  15

Ala Glu Tyr

<210> SEQ ID NO 57
<211> LENGTH: 19
<212> TYPE: PRT
<213> ORGANISM: Artificial Sequence
<220> FEATURE:
<223> OTHER INFORMATION: synthetic
```

<400> SEQUENCE: 57

Thr Phe Phe Tyr Gly Gly Cys Leu Gly Lys Gly Asn Asn Phe Val Ser
1               5                   10                  15

Ala Glu Tyr

<210> SEQ ID NO 58
<211> LENGTH: 19
<212> TYPE: PRT
<213> ORGANISM: Artificial Sequence
<220> FEATURE:
<223> OTHER INFORMATION: synthetic

<400> SEQUENCE: 58

Thr Phe Phe Tyr Gly Gly Cys Leu Gly Asn Arg Asn Asn Phe Asp Arg
1               5                   10                  15

Ala Glu Tyr

<210> SEQ ID NO 59
<211> LENGTH: 19
<212> TYPE: PRT
<213> ORGANISM: Artificial Sequence
<220> FEATURE:
<223> OTHER INFORMATION: synthetic

<400> SEQUENCE: 59

Thr Phe Phe Tyr Gly Gly Cys Leu Gly Asn Arg Asn Asn Phe Leu Arg
1               5                   10                  15

Glu Glu Tyr

<210> SEQ ID NO 60
<211> LENGTH: 19
<212> TYPE: PRT
<213> ORGANISM: Artificial Sequence
<220> FEATURE:
<223> OTHER INFORMATION: synthetic

<400> SEQUENCE: 60

Thr Phe Phe Tyr Gly Gly Cys Leu Gly Asn Lys Asn Asn Tyr Leu Arg
1               5                   10                  15

Glu Glu Tyr

<210> SEQ ID NO 61
<211> LENGTH: 19
<212> TYPE: PRT
<213> ORGANISM: Artificial Sequence
<220> FEATURE:
<223> OTHER INFORMATION: synthetic

<400> SEQUENCE: 61

Pro Phe Phe Tyr Gly Gly Cys Gly Gly Asn Arg Asn Asn Tyr Leu Arg
1               5                   10                  15

Glu Glu Tyr

<210> SEQ ID NO 62
<211> LENGTH: 19
<212> TYPE: PRT
<213> ORGANISM: Artificial Sequence
<220> FEATURE:
<223> OTHER INFORMATION: synthetic

<400> SEQUENCE: 62

Pro Phe Phe Tyr Gly Gly Ser Gly Gly Asn Arg Asn Asn Tyr Leu Arg

```
1               5                   10                  15

Glu Glu Tyr

<210> SEQ ID NO 63
<211> LENGTH: 19
<212> TYPE: PRT
<213> ORGANISM: Artificial Sequence
<220> FEATURE:
<223> OTHER INFORMATION: synthetic

<400> SEQUENCE: 63

Met Arg Pro Asp Phe Cys Leu Glu Pro Pro Tyr Thr Gly Pro Cys Val
1               5                   10                  15

Ala Arg Ile

<210> SEQ ID NO 64
<211> LENGTH: 21
<212> TYPE: PRT
<213> ORGANISM: Artificial Sequence
<220> FEATURE:
<223> OTHER INFORMATION: synthetic

<400> SEQUENCE: 64

Ala Arg Ile Ile Arg Tyr Phe Tyr Asn Ala Lys Ala Gly Leu Cys Gln
1               5                   10                  15

Thr Phe Val Tyr Gly
            20

<210> SEQ ID NO 65
<211> LENGTH: 22
<212> TYPE: PRT
<213> ORGANISM: Artificial Sequence
<220> FEATURE:
<223> OTHER INFORMATION: synthetic

<400> SEQUENCE: 65

Tyr Gly Gly Cys Arg Ala Lys Arg Asn Asn Tyr Lys Ser Ala Glu Asp
1               5                   10                  15

Cys Met Arg Thr Cys Gly
            20

<210> SEQ ID NO 66
<211> LENGTH: 22
<212> TYPE: PRT
<213> ORGANISM: Artificial Sequence
<220> FEATURE:
<223> OTHER INFORMATION: synthetic

<400> SEQUENCE: 66

Pro Asp Phe Cys Leu Glu Pro Pro Tyr Thr Gly Pro Cys Val Ala Arg
1               5                   10                  15

Ile Ile Arg Tyr Phe Tyr
            20

<210> SEQ ID NO 67
<211> LENGTH: 19
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (19)..(19)
<223> OTHER INFORMATION: Amidation
```

<400> SEQUENCE: 67

Thr Phe Phe Tyr Gly Gly Cys Arg Gly Lys Arg Asn Asn Phe Lys Thr
1               5                   10                  15

Glu Glu Tyr

<210> SEQ ID NO 68
<211> LENGTH: 19
<212> TYPE: PRT
<213> ORGANISM: Artificial Sequence
<220> FEATURE:
<223> OTHER INFORMATION: synthetic

<400> SEQUENCE: 68

Lys Phe Phe Tyr Gly Gly Cys Arg Gly Lys Arg Asn Asn Phe Lys Thr
1               5                   10                  15

Glu Glu Tyr

<210> SEQ ID NO 69
<211> LENGTH: 19
<212> TYPE: PRT
<213> ORGANISM: Artificial Sequence
<220> FEATURE:
<223> OTHER INFORMATION: synthetic

<400> SEQUENCE: 69

Thr Phe Tyr Tyr Gly Gly Cys Arg Gly Lys Arg Asn Asn Tyr Lys Thr
1               5                   10                  15

Glu Glu Tyr

<210> SEQ ID NO 70
<211> LENGTH: 19
<212> TYPE: PRT
<213> ORGANISM: Artificial Sequence
<220> FEATURE:
<223> OTHER INFORMATION: synthetic

<400> SEQUENCE: 70

Thr Phe Phe Tyr Gly Gly Ser Arg Gly Lys Arg Asn Asn Phe Lys Thr
1               5                   10                  15

Glu Glu Tyr

<210> SEQ ID NO 71
<211> LENGTH: 20
<212> TYPE: PRT
<213> ORGANISM: Artificial Sequence
<220> FEATURE:
<223> OTHER INFORMATION: synthetic

<400> SEQUENCE: 71

Cys Thr Phe Phe Tyr Gly Cys Cys Arg Gly Lys Arg Asn Asn Phe Lys
1               5                   10                  15

Thr Glu Glu Tyr
            20

<210> SEQ ID NO 72
<211> LENGTH: 20
<212> TYPE: PRT
<213> ORGANISM: Artificial Sequence
<220> FEATURE:
<223> OTHER INFORMATION: synthetic

<400> SEQUENCE: 72

Thr Phe Phe Tyr Gly Gly Cys Arg Gly Lys Arg Asn Asn Phe Lys Thr

Glu Glu Tyr Cys
        20

<210> SEQ ID NO 73
<211> LENGTH: 20
<212> TYPE: PRT
<213> ORGANISM: Artificial Sequence
<220> FEATURE:
<223> OTHER INFORMATION: synthetic

<400> SEQUENCE: 73

Cys Thr Phe Phe Tyr Gly Ser Cys Arg Gly Lys Arg Asn Asn Phe Lys
1               5                   10                  15

Thr Glu Glu Tyr
        20

<210> SEQ ID NO 74
<211> LENGTH: 20
<212> TYPE: PRT
<213> ORGANISM: Artificial Sequence
<220> FEATURE:
<223> OTHER INFORMATION: synthetic

<400> SEQUENCE: 74

Thr Phe Phe Tyr Gly Gly Ser Arg Gly Lys Arg Asn Asn Phe Lys Thr
1               5                   10                  15

Glu Glu Tyr Cys
        20

<210> SEQ ID NO 75
<211> LENGTH: 19
<212> TYPE: PRT
<213> ORGANISM: Artificial Sequence
<220> FEATURE:
<223> OTHER INFORMATION: synthetic

<400> SEQUENCE: 75

Pro Phe Phe Tyr Gly Gly Cys Arg Gly Lys Arg Asn Asn Phe Lys Thr
1               5                   10                  15

Glu Glu Tyr

<210> SEQ ID NO 76
<211> LENGTH: 19
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (19)..(19)
<223> OTHER INFORMATION: Amidation

<400> SEQUENCE: 76

Thr Phe Phe Tyr Gly Gly Cys Arg Gly Lys Arg Asn Asn Phe Lys Thr
1               5                   10                  15

Lys Glu Tyr

<210> SEQ ID NO 77
<211> LENGTH: 19
<212> TYPE: PRT
<213> ORGANISM: Artificial Sequence
<220> FEATURE:
<223> OTHER INFORMATION: synthetic

```
<400> SEQUENCE: 77

Thr Phe Phe Tyr Gly Gly Lys Arg Gly Lys Arg Asn Asn Phe Lys Thr
1               5                   10                  15

Glu Glu Tyr

<210> SEQ ID NO 78
<211> LENGTH: 19
<212> TYPE: PRT
<213> ORGANISM: Artificial Sequence
<220> FEATURE:
<223> OTHER INFORMATION: synthetic

<400> SEQUENCE: 78

Thr Phe Phe Tyr Gly Gly Cys Arg Gly Lys Arg Asn Asn Phe Lys Thr
1               5                   10                  15

Lys Arg Tyr

<210> SEQ ID NO 79
<211> LENGTH: 19
<212> TYPE: PRT
<213> ORGANISM: Artificial Sequence
<220> FEATURE:
<223> OTHER INFORMATION: synthetic

<400> SEQUENCE: 79

Thr Phe Phe Tyr Gly Gly Lys Arg Gly Lys Arg Asn Asn Phe Lys Thr
1               5                   10                  15

Ala Glu Tyr

<210> SEQ ID NO 80
<211> LENGTH: 19
<212> TYPE: PRT
<213> ORGANISM: Artificial Sequence
<220> FEATURE:
<223> OTHER INFORMATION: synthetic

<400> SEQUENCE: 80

Thr Phe Phe Tyr Gly Gly Lys Arg Gly Lys Arg Asn Asn Phe Lys Thr
1               5                   10                  15

Ala Gly Tyr

<210> SEQ ID NO 81
<211> LENGTH: 19
<212> TYPE: PRT
<213> ORGANISM: Artificial Sequence
<220> FEATURE:
<223> OTHER INFORMATION: synthetic

<400> SEQUENCE: 81

Thr Phe Phe Tyr Gly Gly Lys Arg Gly Lys Arg Asn Asn Phe Lys Arg
1               5                   10                  15

Glu Lys Tyr

<210> SEQ ID NO 82
<211> LENGTH: 19
<212> TYPE: PRT
<213> ORGANISM: Artificial Sequence
<220> FEATURE:
<223> OTHER INFORMATION: synthetic

<400> SEQUENCE: 82

Thr Phe Phe Tyr Gly Gly Lys Arg Gly Lys Arg Asn Asn Phe Lys Arg
1               5                   10                  15
```

Ala Lys Tyr

<210> SEQ ID NO 83
<211> LENGTH: 19
<212> TYPE: PRT
<213> ORGANISM: Artificial Sequence
<220> FEATURE:
<223> OTHER INFORMATION: synthetic

<400> SEQUENCE: 83

Thr Phe Phe Tyr Gly Gly Cys Leu Gly Asn Arg Asn Asn Phe Lys Thr
1               5                   10                  15

Glu Glu Tyr

<210> SEQ ID NO 84
<211> LENGTH: 19
<212> TYPE: PRT
<213> ORGANISM: Artificial Sequence
<220> FEATURE:
<223> OTHER INFORMATION: synthetic

<400> SEQUENCE: 84

Thr Phe Phe Tyr Gly Cys Gly Arg Gly Lys Arg Asn Asn Phe Lys Thr
1               5                   10                  15

Glu Glu Tyr

<210> SEQ ID NO 85
<211> LENGTH: 19
<212> TYPE: PRT
<213> ORGANISM: Artificial Sequence
<220> FEATURE:
<223> OTHER INFORMATION: synthetic

<400> SEQUENCE: 85

Thr Phe Phe Tyr Gly Gly Arg Cys Gly Lys Arg Asn Asn Phe Lys Thr
1               5                   10                  15

Glu Glu Tyr

<210> SEQ ID NO 86
<211> LENGTH: 19
<212> TYPE: PRT
<213> ORGANISM: Artificial Sequence
<220> FEATURE:
<223> OTHER INFORMATION: synthetic

<400> SEQUENCE: 86

Thr Phe Phe Tyr Gly Gly Cys Leu Gly Asn Gly Asn Asn Phe Asp Thr
1               5                   10                  15

Glu Glu Glu

<210> SEQ ID NO 87
<211> LENGTH: 19
<212> TYPE: PRT
<213> ORGANISM: Artificial Sequence
<220> FEATURE:
<223> OTHER INFORMATION: synthetic

<400> SEQUENCE: 87

Thr Phe Gln Tyr Gly Gly Cys Arg Gly Lys Arg Asn Asn Phe Lys Thr
1               5                   10                  15

Glu Glu Tyr

```
<210> SEQ ID NO 88
<211> LENGTH: 19
<212> TYPE: PRT
<213> ORGANISM: Artificial Sequence
<220> FEATURE:
<223> OTHER INFORMATION: synthetic

<400> SEQUENCE: 88

Tyr Asn Lys Glu Phe Gly Thr Phe Asn Thr Lys Gly Cys Glu Arg Gly
1               5                   10                  15

Tyr Arg Phe

<210> SEQ ID NO 89
<211> LENGTH: 19
<212> TYPE: PRT
<213> ORGANISM: Artificial Sequence
<220> FEATURE:
<223> OTHER INFORMATION: synthetic

<400> SEQUENCE: 89

Arg Phe Lys Tyr Gly Gly Cys Leu Gly Asn Met Asn Asn Phe Glu Thr
1               5                   10                  15

Leu Glu Glu

<210> SEQ ID NO 90
<211> LENGTH: 19
<212> TYPE: PRT
<213> ORGANISM: Artificial Sequence
<220> FEATURE:
<223> OTHER INFORMATION: synthetic

<400> SEQUENCE: 90

Arg Phe Lys Tyr Gly Gly Cys Leu Gly Asn Lys Asn Asn Phe Leu Arg
1               5                   10                  15

Leu Lys Tyr

<210> SEQ ID NO 91
<211> LENGTH: 19
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (19)..(19)
<223> OTHER INFORMATION: AMIDATION

<400> SEQUENCE: 91

Arg Phe Lys Tyr Gly Gly Cys Leu Gly Asn Lys Asn Asn Tyr Leu Arg
1               5                   10                  15

Leu Lys Tyr

<210> SEQ ID NO 92
<211> LENGTH: 22
<212> TYPE: PRT
<213> ORGANISM: Artificial Sequence
<220> FEATURE:
<223> OTHER INFORMATION: synthetic

<400> SEQUENCE: 92

Lys Thr Lys Arg Lys Arg Lys Lys Gln Arg Val Lys Ile Ala Tyr Glu
1               5                   10                  15

Glu Ile Phe Lys Asn Tyr
            20
```

```
<210> SEQ ID NO 93
<211> LENGTH: 15
<212> TYPE: PRT
<213> ORGANISM: Artificial Sequence
<220> FEATURE:
<223> OTHER INFORMATION: synthetic

<400> SEQUENCE: 93

Lys Thr Lys Arg Lys Arg Lys Lys Gln Arg Val Lys Ile Ala Tyr
1               5                   10                  15

<210> SEQ ID NO 94
<211> LENGTH: 17
<212> TYPE: PRT
<213> ORGANISM: Artificial Sequence
<220> FEATURE:
<223> OTHER INFORMATION: synthetic

<400> SEQUENCE: 94

Arg Gly Gly Arg Leu Ser Tyr Ser Arg Arg Phe Ser Thr Ser Thr Gly
1               5                   10                  15

Arg

<210> SEQ ID NO 95
<211> LENGTH: 10
<212> TYPE: PRT
<213> ORGANISM: Artificial Sequence
<220> FEATURE:
<223> OTHER INFORMATION: synthetic

<400> SEQUENCE: 95

Arg Arg Leu Ser Tyr Ser Arg Arg Arg Phe
1               5                   10

<210> SEQ ID NO 96
<211> LENGTH: 16
<212> TYPE: PRT
<213> ORGANISM: Artificial Sequence
<220> FEATURE:
<223> OTHER INFORMATION: synthetic

<400> SEQUENCE: 96

Arg Gln Ile Lys Ile Trp Phe Gln Asn Arg Arg Met Lys Trp Lys Lys
1               5                   10                  15

<210> SEQ ID NO 97
<211> LENGTH: 19
<212> TYPE: PRT
<213> ORGANISM: Artificial Sequence
<220> FEATURE:
<223> OTHER INFORMATION: synthetic

<400> SEQUENCE: 97

Thr Phe Phe Tyr Gly Gly Ser Arg Gly Lys Arg Asn Asn Phe Lys Thr
1               5                   10                  15

Glu Glu Tyr

<210> SEQ ID NO 98
<211> LENGTH: 59
<212> TYPE: PRT
<213> ORGANISM: Artificial Sequence
<220> FEATURE:
<223> OTHER INFORMATION: synthetic

<400> SEQUENCE: 98
```

```
Met Arg Pro Asp Phe Cys Leu Glu Pro Pro Tyr Thr Gly Pro Cys Val
1               5                   10                  15

Ala Arg Ile Ile Arg Tyr Phe Tyr Asn Ala Lys Ala Gly Leu Cys Gln
                20                  25                  30

Thr Phe Val Tyr Gly Gly Cys Arg Ala Lys Arg Asn Asn Phe Lys Ser
            35                  40                  45

Ala Glu Asp Cys Met Arg Thr Cys Gly Gly Ala
    50                  55
```

```
<210> SEQ ID NO 99
<211> LENGTH: 19
<212> TYPE: PRT
<213> ORGANISM: Artificial Sequence
<220> FEATURE:
<223> OTHER INFORMATION: synthetic

<400> SEQUENCE: 99

Thr Phe Phe Tyr Gly Gly Cys Arg Gly Lys Arg Asn Asn Phe Lys Thr
1               5                   10                  15

Lys Glu Tyr
```

```
<210> SEQ ID NO 100
<211> LENGTH: 19
<212> TYPE: PRT
<213> ORGANISM: Artificial Sequence
<220> FEATURE:
<223> OTHER INFORMATION: synthetic

<400> SEQUENCE: 100

Arg Phe Lys Tyr Gly Gly Cys Leu Gly Asn Lys Asn Asn Tyr Leu Arg
1               5                   10                  15

Leu Lys Tyr
```

```
<210> SEQ ID NO 101
<211> LENGTH: 19
<212> TYPE: PRT
<213> ORGANISM: Artificial Sequence
<220> FEATURE:
<223> OTHER INFORMATION: synthetic

<400> SEQUENCE: 101

Thr Phe Phe Tyr Gly Gly Cys Arg Ala Lys Arg Asn Asn Phe Lys Arg
1               5                   10                  15

Ala Lys Tyr
```

```
<210> SEQ ID NO 102
<211> LENGTH: 35
<212> TYPE: PRT
<213> ORGANISM: Artificial Sequence
<220> FEATURE:
<223> OTHER INFORMATION: synthetic
<300> PUBLICATION INFORMATION:
<310> PATENT DOCUMENT NUMBER: US 5,807,980
<311> PATENT FILING DATE: 1993-07-01
<312> PUBLICATION DATE: 1998-09-15

<400> SEQUENCE: 102

Asn Ala Lys Ala Gly Leu Cys Gln Thr Phe Val Tyr Gly Gly Cys Leu
1               5                   10                  15

Ala Lys Arg Asn Asn Phe Glu Ser Ala Glu Asp Cys Met Arg Thr Cys
                20                  25                  30

Gly Gly Ala
        35
```

```
<210> SEQ ID NO 103
<211> LENGTH: 24
<212> TYPE: PRT
<213> ORGANISM: Artificial Sequence
<220> FEATURE:
<223> OTHER INFORMATION: synthetic
<300> PUBLICATION INFORMATION:
<310> PATENT DOCUMENT NUMBER: US 5,780,265
<311> PATENT FILING DATE: 1995-07-05
<312> PUBLICATION DATE: 1998-07-14

<400> SEQUENCE: 103

Tyr Gly Gly Cys Arg Ala Lys Arg Asn Asn Phe Lys Ser Ala Glu Asp
1               5                   10                  15

Cys Met Arg Thr Cys Gly Gly Ala
            20

<210> SEQ ID NO 104
<211> LENGTH: 22
<212> TYPE: PRT
<213> ORGANISM: Artificial Sequence
<220> FEATURE:
<223> OTHER INFORMATION: synthetic
<300> PUBLICATION INFORMATION:
<310> PATENT DOCUMENT NUMBER: WO04/060403
<311> PATENT FILING DATE: 2004-01-05
<312> PUBLICATION DATE: 2004-06-22

<400> SEQUENCE: 104

Gly Leu Cys Gln Thr Phe Val Tyr Gly Gly Cys Arg Ala Lys Arg Asn
1               5                   10                  15

Asn Phe Lys Ser Ala Glu
            20

<210> SEQ ID NO 105
<211> LENGTH: 20
<212> TYPE: PRT
<213> ORGANISM: Artificial Sequence
<220> FEATURE:
<223> OTHER INFORMATION: synthetic
<300> PUBLICATION INFORMATION:
<310> PATENT DOCUMENT NUMBER: US 5,118,668
<311> PATENT FILING DATE: 1988-07-20
<312> PUBLICATION DATE: 1992-06-02

<400> SEQUENCE: 105

Leu Cys Gln Thr Phe Val Tyr Gly Gly Cys Glu Ala Lys Arg Asn Asn
1               5                   10                  15

Phe Lys Ser Ala
            20

<210> SEQ ID NO 106
<211> LENGTH: 180
<212> TYPE: DNA
<213> ORGANISM: Artificial Sequence
<220> FEATURE:
<223> OTHER INFORMATION: synthetic
<300> PUBLICATION INFORMATION:
<308> DATABASE ACCESSION NUMBER: x04666
<309> DATABASE ENTRY DATE: 1993-09-13
<313> RELEVANT RESIDUES IN SEQ ID NO: (217)..(396)

<400> SEQUENCE: 106
atgagaccag atttctgcct cgagccgccg tacactgggc cctgcaaagc tcgtatcatc      60
cgttacttct acaatgcaaa ggcaggcctg tgtcagacct cgtatacgg cggctgcaga      120
```
gctaagcgta acaacttcaa atccgcggaa gactgcatgc gtacttgcgg tggtgcttag    180

<210> SEQ ID NO 107
<211> LENGTH: 19
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (19)..(19)
<223> OTHER INFORMATION: Acetylation

<400> SEQUENCE: 107

Thr Phe Phe Tyr Gly Gly Ser Arg Gly Lys Arg Asn Asn Phe Lys Thr
1               5                   10                  15

Glu Glu Tyr

<210> SEQ ID NO 108
<211> LENGTH: 19
<212> TYPE: PRT
<213> ORGANISM: Artificial Sequence
<220> FEATURE:
<223> OTHER INFORMATION: synthetic

<400> SEQUENCE: 108

Arg Phe Phe Tyr Gly Gly Ser Arg Gly Lys Arg Asn Asn Phe Lys Thr
1               5                   10                  15

Glu Glu Tyr

<210> SEQ ID NO 109
<211> LENGTH: 19
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (19)..(19)
<223> OTHER INFORMATION: ACETYLATION

<400> SEQUENCE: 109

Arg Phe Phe Tyr Gly Gly Ser Arg Gly Lys Arg Asn Asn Phe Lys Thr
1               5                   10                  15

Glu Glu Tyr

<210> SEQ ID NO 110
<211> LENGTH: 19
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (19)..(19)
<223> OTHER INFORMATION: ACETYLATION

<400> SEQUENCE: 110

Arg Phe Phe Tyr Gly Gly Ser Arg Gly Lys Arg Asn Asn Phe Arg Thr
1               5                   10                  15

Glu Glu Tyr

```
<210> SEQ ID NO 111
<211> LENGTH: 19
<212> TYPE: PRT
<213> ORGANISM: Artificial Sequence
<220> FEATURE:
<223> OTHER INFORMATION: synthetic

<400> SEQUENCE: 111

Thr Phe Phe Tyr Gly Gly Ser Arg Gly Lys Arg Asn Asn Phe Arg Thr
1               5                   10                  15

Glu Glu Tyr

<210> SEQ ID NO 112
<211> LENGTH: 19
<212> TYPE: PRT
<213> ORGANISM: Artificial Sequence
<220> FEATURE:
<223> OTHER INFORMATION: synthetic

<400> SEQUENCE: 112

Thr Phe Phe Tyr Gly Gly Ser Arg Gly Arg Arg Asn Asn Phe Arg Thr
1               5                   10                  15

Glu Glu Tyr
```

POTENTIATION OF ANTICANCER AGENTS

REFERENCE TO A SEQUENCE LISTING

This application contains a Sequence Listing in computer readable form. The computer readable form is incorporated herein by reference.

FIELD OF THE INVENTION

The present invention relates to carriers conjugates and pharmaceutical compositions and their use to increase the potency of drugs and to modify the pharmacokinetics of compounds. More particularly, the present invention relates to conjugates comprising the carrier described herein and their use in the treatment and diagnostic of cancer.

BACKGROUND OF THE INVENTION

Clinical progress in the treatment of primary tumors has been slow and one of the problems associated with these tumors is their weak response to anticancer drugs. The effectiveness of chemotherapy and immunotherapy have been impaired by inherent or acquired multiple drug resistance (MDR) phenotype by cancer cells. One mechanism involved in MDR phenotype is caused by the expression of P-glycoprotein (P-gp), a membrane transporter that pumps out various anticancer drugs from MDR1 expressing cells. P-gp is also expressed in a large number of normal secretory tissues such as kidney, liver and intestine. This efflux pump is strongly expressed in the brain capillaries where its expression was mainly localized in the luminal membrane of endothelial cells lining these. In human, P-gp is encoded by two MDR genes; MDR1 and MDR3. P-gp encoded by the human MDR1 gene confers the resistance phenotype whereas P-gp encoded by the human MDR3 gene does not. Thus, P-gp may be seen as a guardian that limits the entry of drugs by expulsing them out of the brain or out of cancer cells preventing them from reaching cytotoxic concentrations.

Cancer cells forming brain metastases originate mostly from lung or breast cancers, colorectal carcinoma, melanoma and urinary organ tumors. These metastases, which often occur after surgery, primary chemotherapy treatment or radiotherapy, are chemo-resistant. Chemotherapy against brain metastases could be effective only if it was effective for their corresponding originate tumors. For example, it was shown that brain metastases originating from small cell lung carcinomas and germ cells respond with similar rates than metastases at other sites.

Drug resistance may be an intrinsic property of tumor cells or may be acquired after treatment. The presence of the P-gp efflux pump encoded by MDR1 (also herein referred as P-glycoprotein, MDR1 P-gp or MDR1) has been reported in most of the primary brain tumors where most gliomas and more particularly endothelial cells of newly formed capillaries were stained positive for MDR1 P-gp. Thus, various studies support the idea that the multiple drug resistance phenotype may be caused not only by the expression of P-gp in cancer cells but also from its expression in the newly formed endothelial cells in the tumors. MDR1 levels were also found significantly lower in brain metastasis from melanomas and lung adenocarcinomas. In addition, it was shown that treatments prior to surgery have no major impact on MDR1 levels in brain metastasis from melanomas since they were identical in patients that received radiotherapy, chemotherapy or both treatments. In lung metastasis, MDR1 was only detected in patients that received chemotherapy indicating that these previous treatments may have induced its expression resulting in an acquired MDR phenotype. The lack of MDR1 expression in primary lung tumors and in their corresponding brain metastasis indicates also that these metastases did not acquire the same levels of P-gp expression during their development than the ones found in normal brain tissue. These results also indicate that the MDR1 levels of endothelial cells from capillaries in brain metastasis differed from the one of primary brain tumors. The lack of MDR1 expression in some brain metastasis may explain in part why some of them are more sensitive to chemotherapeutic drugs than primary brain tumors.

Methods for transporting a compound across the blood-brain barrier have been described in international application no. PCT/CA2004/000011 published on Jul. 22, 2004 under publication No. WO2004060403, the entire content of which is incorporated herein by reference. Briefly, in this document, aprotinin, aprotinin fragments and analogs were presented as a drug delivery system for the central nervous system (CNS) and for treating CNS related diseases.

There remains a need for increasing the potency of anticancer drugs.

The present invention seeks to meet these and other needs.

SUMMARY OF THE INVENTION

The present invention relates in one aspect thereof, to a carrier comprising an amino acid sequence selected from the group consisting of the amino acid sequence of aprotinin, a biologically active aprotinin fragment, Angiopep-1, Angiopep-2 and biologically active analogs, derivatives or fragments thereof. The aprotinin sequence as well as some exemplary embodiments of biologically active analogs may be found for example in international application no. PCT/CA2004/000011.

The present invention also relates to a carrier consisting of an amino acid sequence selected from the group consisting of the amino acid sequence of aprotinin, a biologically active aprotinin fragment, Angiopep-1, Angiopep-2 and biologically active analogs, derivatives or fragments thereof.

Exemplary embodiment of carriers encompassed by the present invention includes those which may be selected, for example, from the group consisting of
  aprotinin (SEQ ID NO.:98),
  an aprotinin analogue
  an aprotinin fragment which may comprise (or may consist essentially of) the amino acid sequence defined in SEQ ID NO.:1,
  a biologically active analogue of SEQ ID NO.:1,
  a biologically active fragment of SEQ ID NO.:1, and;
  a biologically active fragment of a SEQ ID NO.:1 analogue.

More particularly, the carrier may be selected, for example, from the group of;
  an aprotinin fragment which may comprise the amino acid sequence defined in SEQ ID NO.:1,
  a biologically active analogue of SEQ ID NO.:1,
  a biologically active fragment of SEQ ID NO.:1 and;
  a biologically active fragment of a SEQ ID NO.:1 analogue.

In accordance with the present invention the aprotinin fragment may consist of the sequence defined in SEQ ID NO.:1. Further in accordance with the present invention, the aprotinin fragment may comprise SEQ ID NO.1 and may have a length of from about 19 amino acids to about 54 amino acids, e.g., from 10 to 50 amino acids in length, from 10 to 30 amino acids in length etc.

In accordance with the present invention, the biologically active analogue of SEQ ID NO.:1, may have a length of from about 19 amino acids to about 54 amino acids (e.g., including for example 21 to 23, 25 to 34, 36 to 50 and 52 to 54), or of from about 19 amino acids to about 50 amino acids, or from about 19 amino acids to about 34 amino acids (e.g., 19, 20, 21, 22, 23, 25, 26, 27, 28, 29, 30, 31, 32, 33, 34), of from about 19 amino acids to about 23 amino acids or of about 19, 20, 21, 22, 23, 24, 35, 51, amino acids.

A biologically active fragment of a polypeptide (e.g., of 19 amino acids) described herein may include for example a polypeptide of from about 7, 8, 9 or 10 to 18 amino acids (i.e., 11-18, 12-18, 13-18, 14-18, 15-18, 16-18, 17-18). Therefore, in accordance with the present invention, a biologically active fragment of SEQ ID NO.:1 or of a SEQ ID NO.:1 analogue may have a length of from about 7 to about 18 amino acids or from about 10 about 18 amino acids.

The polypeptides of the present invention may be amidated, i.e., may have an amidated amino acid sequence. The polypeptides of the present invention may be acylated.

Exemplary embodiments of the peptides of the present invention are those having a Lysine at position 10 (with respect to amino acid sequence of SEQ ID NO.:1). Other exemplary embodiments of the peptides of the present invention are those having a Lysine at position 15 (with respect to amino acid sequence of SEQ ID NO.:1). Further exemplary embodiment of peptides of the present invention are those having Lysines at positions 10 and 15. The peptides of the present invention may also have a serine or cysteine at position 7 (with respect to amino acid sequence of SEQ ID NO.:1). When multimerization of peptides is desired, the peptide may preferably comprises a cysteine at position 7. However, when multimerization of peptides is not required, the peptide may preferably have a serine at position 7.

U.S. Pat. No. 5,807,980 describes a polypeptide which is identified herein as SEQ ID NO.:102.

U.S. Pat. No. 5,780,265 describes a polypeptide which is identified herein as SEQ ID NO.:103.

The aprotinin amino acid sequence (SEQ ID NO.:98), the Angiopep-1 amino acid sequence (SEQ ID NO.:67), as well as some sequences of biologically active analogs may be found for example in international application no. PCT/CA2004/000011 published on Jul. 22, 2004 in under international publication no. WO2004/060403. Additionally, international publication No. WO04/060403 describes a polypeptide which is identified herein as SEQ ID NO.: 104.

U.S. Pat. No. 5,118,668 describes polypeptides which has the sequence illustrated in SEQ ID NO.: 105.

Even more particularly, the carrier may be selected, for example, from the group of;
a SEQ ID NO.:1 analogue which may comprise at least 35% identity with the amino acid sequence of SEQ ID NO.:1,
a SEQ ID NO.:1 analogue which may comprise at least 40% identity with the amino acid sequence of SEQ ID NO.:1,
a SEQ ID NO.:1 analogue which may comprise at least 50% identity with the amino acid sequence of SEQ ID NO.:1,
a SEQ ID NO.:1 analogue which may comprise at least 60% identity with the amino acid sequence of SEQ ID NO.:1,
a SEQ ID NO.:1 analogue which may comprise at least 70% identity with the amino acid sequence of SEQ ID NO.:1,
a SEQ ID NO.:1 analogue which may comprise at least 80% identity with the amino acid sequence of SEQ ID NO.:1,
a SEQ ID NO.:1 analogue which may comprise at least 90% identity with the amino acid sequence of SEQ ID NO.:1 and;
a SEQ ID NO.:1 analogue which may comprise at least 95% (i.e., 96%, 97%, 98%, 99% and 100%) identity with the amino acid sequence of SEQ ID NO.:1.

For example, the biologically active analogue of SEQ ID NO.:1 may comprise an amino acid sequence selected from the group consisting of an amino acid sequence defined in any one of SEQ ID NO.:2 to SEQ ID NO.: 62, SEQ ID NO.: 68 to SEQ ID NO.: 93, and SEQ ID NO.:97 as well as 99, 100, 101 or any of SEQ ID NO.:107-112.

Further in accordance with the present invention, the biologically active analogue of SEQ ID NO.:1 may comprise the amino acid sequence defined in SEQ ID NO.:67. This sequence may more particularly be amidated.

For example and without limitation, conjugates comprising peptides SEQ ID NO.: 102, 103, 104 and 105 are also encompassed by the present invention.

Further in accordance with the present invention, the biologically active fragment of SEQ ID NO.:1 or the biologically active fragment of a SEQ ID NO.:1 analogue may comprise at least 9 or at least 10 (consecutive or contiguous) amino acids of SEQ ID NO.1 or of the SEQ ID NO.:1 analogue.

The polypeptides of the present invention may have an amino acid sequence which may comprise of from between 1 to 12 amino acid substitutions (i.e., SEQ ID NO.:91). For example, the amino acid substitution may be from between 1 to 10 amino acid substitutions, or from 1 to 5 amino acid substitutions. In accordance with the present invention, the amino acid substitution may be a non-conservative amino acid substitution or a conservative amino acid substitution.

For example, when a polypeptide of the present invention comprises amino acids which are identical to those of SEQ ID NO.:1 and other amino acids which are not identical (non-identical), those which are non-identical may be a conservative amino acid substitution. The comparison of identical and non-identical amino acids may be performed by looking at a corresponding location.

Examples of SEQ ID NO.:1 analogue which may have at least 35% identity includes for example, a polypeptide comprising (consisting of) the amino acid sequence defined in SEQ ID NO.:91 (about 36.8% identity, i.e., 7 amino acid out of 19 amino acids of SEQ ID NO.:91 are identical to SEQ ID NO.:1), a polypeptide comprising (consisting of) the amino acid sequence defined in SEQ ID NO.:98 (about 68.4% identity, i.e., 13 amino acid out of 19 amino acids are identical to SEQ ID NO.:1), a polypeptide comprising (consisting of) the amino acid sequence defined in SEQ ID NO.:67 (about 73.7% identity, i.e., 14 amino acid out of 19 amino acids are identical to SEQ ID NO.:1), a polypeptide comprising (consisting of) the amino acid sequence defined in SEQ ID NO.: 76 (about 73.7% identity, i.e., 14 amino acid out of 19 amino acids are identical to SEQ ID NO.:1) and a polypeptide comprising (consisting of) the amino acid sequence defined in SEQ ID NO.:5 (about 79% identity, i.e., 15 amino acid out of 19 amino acids are identical to SEQ ID NO.:1).

Examples of SEQ ID NO.:1 analogue which may have at least 60% identity includes for example, a polypeptide comprising (consisting of) the amino acid sequence defined in SEQ ID NO.:98 (about 68.4% identity, i.e., 13 amino acid out of 19 amino acids are identical to SEQ ID NO.:1), a polypeptide comprising (consisting of) the amino acid sequence defined in SEQ ID NO.:67 (about 73.7% identity, i.e., 14 amino acid out of 19 amino acids are identical to SEQ ID NO.:1), a polypeptide comprising (consisting of) the amino acid sequence defined in SEQ ID NO.: 76 (about 73.7% identity, i.e., 14 amino acid out of 19 amino acids are identical to SEQ ID NO.:1) and a polypeptide comprising (consisting of) the amino acid sequence defined in SEQ ID NO.:5 (about 79% identity, i.e., 15 amino acid out of 19 amino acids are identical to SEQ ID NO.:1).

Examples of SEQ ID NO.:1 analogue which may have at least 70% identity includes for example, a polypeptide comprising (consisting of) the amino acid sequence defined in SEQ ID NO.:67 (about 73.7% identity, i.e., 14 amino acid out of 19 amino acids are identical to SEQ ID NO.:1), SEQ ID NO.: 76 (about 73.7% identity, i.e., 14 amino acid out of 19 amino acids are identical to SEQ ID NO.:1), SEQ ID NO.:5 (about 79% identity, i.e., 15 amino acid out of 19 amino acids are identical to SEQ ID NO.:1).

In accordance, with the present invention, the carrier may more particularly be selected from the group consisting of peptide Nos. 5, 67, 76, 91 and peptide 97 (i.e., SEQ ID NO.:5, 67, 76, 91 and 97 (Angiopep-2)).

The present invention particularly relates to the use of a carrier or the pharmaceutical composition described herein for modifying and/or improving the (in vivo) pharmacokinetics of a compound.

In accordance with the present invention, the compound may be selected, for example, from the group consisting of a label, a protein, a peptide and a small molecule drug and combination thereof.

Also in accordance with the present invention, the small molecule drug may be, for example, an anticancer drug.

In accordance with the present invention the anticancer drug may be conjugated with the carrier thereby forming a conjugate. In an exemplary embodiment of the invention, the conjugate may comprise, for example, at least one anticancer drug molecule for each carrier molecule. In another exemplary embodiment of the invention, the conjugate may comprise, for example, at least two anticancer drug molecules for each carrier molecule. In yet another exemplary embodiment of the invention, the conjugate may comprise, for example, at least three anticancer drug molecules for each carrier molecule.

In accordance with the present invention the carrier may promote accumulation of the drug in a tissue such as, for example, a kidney (kidney tissue), a liver (liver tissue), an eye (eye tissue) and the lungs (lung tissue) of an individual.

Also in accordance with the present invention, the carrier may modify or improve the bioavailability of the compound.

Further in accordance with the present invention, the carrier may also change the (usual) tissue distribution of the compound.

In accordance with the present invention the carrier may also promote accumulation of the drug in the brain (brain tissue) of an individual.

In accordance with the present invention, the brain may be a tumoral brain.

Further in accordance with the present invention, the brain may comprise a lung cancer cell.

Also in accordance with the present invention, the carrier may promote accumulation of the drug in a cancer cell (e.g., intracellular accumulation of the drug in the cancer cell).

As used herein the term "tumoral brain" refers to a brain which comprises a tumor, either a primary tumor or a metastasis of a different tissue origin, such as, without limitation, a metastasis originating from a lung tumor, a breast tumor, from a melanoma, from a colorectal tumor, from a tumor of an urinary organ or else. Examples of tumoral brain cells thus include, for example, glioblastomas, and metastatic cell originating, for example, from the lung, breast, colon, urinary tract or from melanoma.

In accordance with the present invention, the carrier may thus be used, for example, for reducing the dose of a drug, necessary to achieve the same therapeutic effect (e.g., to achieve a reduction in tumor cell growth, etc.).

The present invention further relates to the use of a carrier selected from the group consisting of aprotinin, a biologically active aprotinin fragment, Angiopep-1, Angiopep-2, biologically active analogs, derivatives or fragments and combination thereof for transporting a compound to a desired target site, a desired target tissue or a desired target cell.

Examples of a small molecule drug which may be conjugated with the carrier of the present invention and which are encompassed herewith, includes for example and without limitation, Taxol, a Taxol derivative, vinblastine, vincristine, etoposide, doxorubicin, cyclophosphamide, Taxotere, melphalan, chlorambucil, pharmaceutically acceptable salts, etc. and combination thereof as well as any drug which may be a P-gp substrate.

Other small molecule drug encompassed by the present invention may include, for example, a drug having a group allowing it's conjugation to the carrier of the present invention.

In accordance with the present invention, exemplary embodiments of Taxol derivatives (or analogues) include for example, derivatives disclosed and referred to in U.S. Pat. No. 6,911,549 issued on Jun. 28, 2005, the entire contents of which is incorporated herein by reference.

Examples of labels which may be conjugated with the carrier of the present invention and which are encompassed herewith include, for example and without limitation, an isotope, a fluorescent label (e.g., rhodamine), a reporter molecule (e.g., biotin), etc.

Examples of protein which may be conjugated with the carrier of the present invention and which are encompassed herewith includes, without limitation, an antibody, an antibody fragment, a peptidic- or protein-based drug (e.g., a positive pharmacological modulator (agonist) or an pharmacological inhibitor (antagonist)) etc.

The present invention also provides the use of a carrier selected from the group consisting of aprotinin, a biologically active aprotinin fragment, Angiopep-1, Angiopep-2, biologically active analogs, derivatives or fragments and combination thereof for increasing the potency of a drug. More particularly, the carrier may be used to increase, for example, the potency of a drug which may be a P-gp substrate or drugs which are expulsed (i.e., expelled, ejected from a cell, etc.) by P-gp or P-gp related protein (e.g., a P-gp human or mammalian allelic variant, e.g., a mdr1a and/or mdr1b isoforms from a rodent, etc.).

The carrier may be used for reducing the toxicity of a drug, upon their conjugation, and therefore allows administration of the drug at a dose which is higher than the recommended dose for the drug alone.

Therefore the present invention provides a method of treating a patient having a cancer, the method may comprise administering a conjugate comprising the carrier of the present invention and the desired drug at a dose higher than the therapeutic dose of the drug. At comparable dosage the conjugate may be associated with less toxicity than the unconjugated drug (without the carrier), therefore allowing administration of a higher dose of the drug in the conjugated form.

The term "therapeutic dose" as used herein means the dosage of a drug (without the carrier) that is acceptable for use clinically with respect to its toxicity.

In accordance with the present invention, the carrier may increase for example, the potency of an anticancer drug, for example, an anticancer drug which may be P-gp substrates.

In yet an additional aspect, the present invention more particularly relates to the use of a carrier, conjugate or the pharmaceutical composition described herein for increasing (optimizing) an anti-tumor growth effect of an anticancer drug.

The present invention further provides the use of a carrier selected from the group consisting of aprotinin, a biologically active aprotinin fragment, Angiopep-1, Angiopep-2, biologically active analogs, derivatives or fragments and combination thereof for transporting a drug or a label at or to a desired target site or for transporting a drug or a label inside a target cell and/or for promoting the accumulation of a drug or a label inside a cell, such as for example, a cell which expresses P-gp at its surface or a cell which is able to express P-gp (at its surface).

The carrier may be used, for example, for promoting the accumulation, inside a cell, of a drug which may comprise the characteristic of being expulsed (i.e., expelled, transported outside a cell, ejected) by P-gp or a P-gp related protein.

In accordance with the present invention, the desired site may be, for example and without limitation, the brain or other sites outside the brain (e.g., an extracranial site) such as for example, the kidney, the liver, the pancreas, the colon, the eyes, the lungs and combination thereof. Therefore, the desired target site may be one or more site selected from the group consisting of the brain, the kidney, the liver, the pancreas, the colon, the eyes, the lungs and combination thereof.

In accordance with a particular embodiment of the present invention, a desired target site may be, for example, a brain cell or tissue.

In accordance with another particular embodiment of the present invention, a desired target site may be, for example, a liver cell or tissue.

In accordance with a further particular embodiment of the present invention, a desired target site may be for example, a kidney cell or tissue.

In accordance with yet a further particular embodiment of the present invention, a desired target site may be for example, a pancreas cell or tissue.

In accordance with another particular embodiment of the present invention, a desired target site may be for example, a colon cell or tissue.

In accordance with yet another particular embodiment of the present invention, a desired target site may be for example, eye or an eye cell.

In accordance with a further particular embodiment of the present invention, a desired target site may be for example, a lung cell or tissue.

Further in accordance with the present invention, the desired site may be a site which comprises a cell expressing a carrier receptor or transporter, for example, a cell expressing a low-density lipoprotein related receptor (LRP). The cell may also be a cell which co-expresses P-gp or a P-gp related protein. The cell may be, for example a normal cell, a tumor cell, or a metastatic cell. The carrier of the present invention may thus be used to target a brain cell, a liver cell, a kidney cell, a pancreas cell, a colon cell, an eye cell, a lung cell and combination thereof (either normal or tumoral).

The present invention also relates in a more particular aspect thereof to the use of a carrier described herein (e.g., which may be selected from the group consisting of aprotinin, a biologically active aprotinin fragment, Angiopep-1, Angiopep-2 and biologically active analogs, derivatives or fragments thereof) or the pharmaceutical composition or the conjugate described herein for promoting intracellular accumulation of a compound (i.e., promoting accumulation of the compound inside a cell).

In accordance with an embodiment of the present invention, the compound may be selected, for example, from the group consisting of a label, a protein, a peptide and a small molecule drug.

In accordance with a further embodiment of the present invention, the cell may be a cell which is able to express P-gp or which expresses P-gp. More particularly the cell may express P-gp (MDR1) at the cell surface.

The cell may be, for example, a tumor cell. The tumor cell may originate for example and without limitation, from a brain tumor, a lung tumor, a breast tumor, a kidney tumor, an eye tumor, a liver tumor, a colorectal tumor, a tumor of an urinary organ, etc.

In accordance with the present invention the cell may be located outside of a brain of an individual (mammal, animal, etc.). For example, the cell may be a tumor cell which may be located outside of a brain of an individual (mammal, animal, etc.).

In accordance with a further embodiment of the present invention, the cell may be located inside a brain of an individual. The cell may be, for example, a tumor cell which may be located inside of a brain of an individual (mammal, animal, etc.).

In an exemplary embodiment of the present invention, the tumor cell may be a brain tumor cell. For example, the brain tumor cell may originate from a glioblastoma or may be a glioblastoma.

In another exemplary embodiment of the present invention, the tumor cell may be a lung tumor cell.

The present invention also relates in an additional aspect thereof to the use of the carrier, the conjugate or the pharmaceutical composition described herein for reducing the elimination of a drug from the inside of a cell, such as for example a cell which may be able to express P-gp (MDR1) or which expresses P-gp. In accordance with the present invention, the drug may be a P-gp substrate.

Also in accordance with the present invention, the cell may be a multiple drug resistant cancer cell.

In yet an additional aspect thereof, the present invention relates to the use of a carrier, the conjugate or the pharmaceutical composition described herein for reducing the growth of a cell. For that purpose, the carrier may be conjugated with a drug which may be able to reduce the growth of a cell.

In accordance with a non-limitative exemplary embodiment of the invention, the carrier, the conjugate thus formed or the pharmaceutical composition may be used to reduce the growth of a tumor cell or an endothelial cell.

In a particular embodiment of the invention, the tumor cell may be able to express or expresses P-gp (MDR1).

In an exemplary embodiment of the invention, the tumor cell may be a brain tumor cell. More specifically, the brain tumor cell may originate from a glioblastoma or may be a glioblastoma.

In another exemplary embodiment of the invention, the tumor cell may be a lung tumor cell.

In yet another exemplary embodiment of the invention, the tumor cell may be a breast tumor cell.

In a further exemplary embodiment of the invention, the tumor cell may be a kidney tumor cell.

In yet a further exemplary embodiment of the invention, the tumor cell may be an eye tumor cell.

In an additional embodiment of the invention, the tumor cell may be from a colorectal cancer.

In another embodiment of the invention, the tumor cell may be from the liver.

In yet another additional embodiment of the invention, the tumor cell may be from a urinary organ tumor.

In a particular embodiment of the invention, the anticancer drug may, more specifically be Taxol, Taxotere or a Taxol or Taxotere derivative.

In accordance with another embodiment of the present invention, the anticancer drug may be, for example, vinblastine.

In accordance with yet another embodiment of the present invention, the anticancer drug may be, for example, vincristine.

In accordance with a further embodiment of the present invention, the anticancer drug may be, for example, etoposide.

In accordance with a further embodiment of the present invention, the anticancer drug may be, for example, doxorubicin.

In accordance with an additional embodiment of the present invention, the anticancer drug may be, for example, cyclophosphamide.

In accordance with yet an additional embodiment of the present invention, the anticancer drug may be, for example, melphalan.

In accordance with yet another embodiment of the present invention, the anticancer drug may be, for example chlorambucil.

In another aspect, the present invention relates to the use of a carrier described herein in the making of a pharmaceutical composition or medicament for modifying the pharmacokinetics of the small molecule drug.

More particularly the carrier may be used for reducing the growth of a cell.

Also more particularly, the carrier may be used for promoting accumulation of the small molecule drug inside a cell.

In addition the carrier may be used for reducing the elimination of the small molecule drug from the inside of a cell.

Also, the carrier may be used for increasing an anti-tumor growth effect of the small molecule drug.

Furthermore, the carrier may be used to improve the bioavailability of the small molecule drug.

In addition and in accordance with the present invention, the carrier may be used to change the (usual) tissue distribution of the small molecule drug.

In addition, the present invention relates to the use of a carrier selected from the group consisting of aprotinin, a biologically active aprotinin fragment, Angiopep-1, Angiopep-2, biologically active analog and combination thereof for treating cancer, metastatic cancer and/or metastasis. In accordance with the present invention, an exemplary metastasis may comprise, without limitation, a metastasis which may originate from a breast tumor, a lung tumor, a melanoma, etc.

The present invention also relates to the use of a carrier selected from the group consisting of aprotinin, a biologically active aprotinin fragment, Angiopep-1, Angiopep-2, biologically active analogs, derivatives or fragments and combination thereof for the detection of a desired target cell.

The present invention further provides the use of a carrier selected from the group consisting of aprotinin, a biologically active aprotinin fragment, Angiopep-1, Angiopep-2, biologically active analogs, derivatives or fragments and combination thereof for the diagnostic of a cancer, a metastatic cancer and/or metastasis.

The present invention additionally relates in a further aspect, to a composition (e.g., pharmaceutical composition) comprising a carrier (and/or pharmaceutically acceptable salt thereof) of the present invention and a pharmaceutically acceptable carrier.

The present invention in an additional aspect relates to a conjugate and/or pharmaceutically acceptable salt thereof. The conjugate may comprise, for example, a carrier as described herein and a drug, a label or a protein. The carrier may be covalently attached to the drug, label, protein or peptide.

More particularly, the conjugate may comprise, for example a carrier selected from the group consisting of aprotinin, a biologically active aprotinin fragment, Angiopep-1, Angiopep-2, biologically active analogs, derivatives or fragments and combination thereof and a compound selected from the group consisting of a drug, a label, a protein and combination thereof. In accordance with the present invention, the conjugate may comprise one or more drug molecules.

Also in accordance with the present invention, the compound may or may not be released from the carrier. The compound may therefore be releasable from the conjugate (or from the carrier).

In accordance with the present invention, the conjugate may comprise the formula R-L-M wherein R is a class of molecules related to aprotinin (e.g., aprotinin, aprotinin fragment, Angiopep-1, Angiopep-2, analogs, derivatives or fragments), L may be a linker or a bond and M may be an agent or a drug selected from the group consisting of a drug (e.g., a small molecule drug), a label, a protein (e.g., antibody, an antibody fragment) and a polypeptide. It is to be understood herein that the formula R-L-M is not intended to be restricted to a specific order or specific ratio. As being exemplified herein, M may be found in several ratios over R.

The present invention relates in a further aspect thereof to the use of a conjugate which may comprise a) a carrier which may be selected from the group consisting of aprotinin, a biologically active aprotinin fragment, Angiopep-1, Angiopep-2 and biologically active analogs, derivatives or fragments thereof and b) at least one small molecule drug or label for modifying the pharmacokinetics (in vivo) of the drug or label which is attached thereto.

In accordance with one embodiment of the present invention, the conjugate may be, more particularly, used for reducing the growth of a cell.

Further in accordance with the present invention, the conjugate may be used for promoting accumulation of the small molecule drug or label inside a cell.

Also in accordance with the present invention, the conjugate may also be used for reducing the elimination of the small molecule drug or label from the inside of a cell.

Further in accordance with the present invention, the conjugate may be used for increasing an anti-tumor growth effect of the small molecule drug.

Also in accordance with the present invention, the conjugate may improve the bioavailability of the compound.

Further in accordance with the present invention, the conjugate may also change the tissue distribution of the compound.

In one embodiment of the invention, the small molecule drug may be able to reduce the growth of a cell.

The present invention also provides in an additional aspect thereof for the use of a conjugate which may comprise a) a carrier which may be selected, for example, from the group consisting of aprotinin, a biologically active aprotinin fragment, Angiopep-1, Angiopep-2 and biologically active analogs, derivatives or fragments thereof and b) at least one small molecule drug in the making (manufacture) of a pharmaceutical composition or medicament for modifying the pharmacokinetics of the small molecule drug.

The present invention also relates to the use of the carrier in the manufacture of a composition or medicament for the treatment of a condition such as cancer, metastatic cancer and/or metastasis.

The present invention also provides in an additional aspect thereof for the use of a conjugate which may comprise a) a carrier which may be selected, for example, from the group consisting of aprotinin, a biologically active aprotinin fragment, Angiopep-1, Angiopep-2 and biologically active analogs, derivatives or fragments thereof and b) at least one label, for the detection of a cell (e.g., tumor cell) which may be selected, for example, from the group consisting of an eye cell, a brain cell, a breast cell, a liver cell a kidney cell, a urinary organ cell, a colon cell, a cell from the rectum and a lung cell.

In a particular embodiment of the present invention, the cell which may be detected may be, for example, an eye cell.

In another particular embodiment of the present invention, the cell which may be detected may be, for example, a brain cell.

In an additional particular embodiment of the present invention, the cell which may be detected may be, for example, a liver cell.

In yet an additional particular embodiment of the present invention, the cell which may be detected may be, for example, a breast cell.

In another particular embodiment of the present invention, the cell which may be detected may be, for example, a kidney cell.

In yet another particular embodiment of the present invention, the cell which may be detected may be, for example, lung cell. The present invention additionally relates to a composition (e.g., pharmaceutical composition) comprising a conjugate of the present invention and a pharmaceutically acceptable carrier.

The pharmaceutical composition described herein may be used, for example, in the treatment or detection of cancer, a metastatic cancer and/or metastasis.

The present invention provides in a particular aspect thereof, a pharmaceutical composition which may be able, for example, of reducing the growth of a cell (e.g., tumor cell) or for the detection of a cell (e.g., tumor cell), the pharmaceutical composition may comprise:
  a) a conjugate which may comprise a carrier selected from the group consisting of aprotinin, a biologically active aprotinin fragment, Angiopep-1, Angiopep-2 and biologically active analogs, derivatives or fragments thereof and a label or a small molecule drug able to reduce the growth of a cell (e.g., tumor cell) and;
  b) a pharmaceutically acceptable carrier.

The present invention also provides in a further aspect thereof, a pharmaceutical composition which may comprise:
  a) a conjugate which may comprise a carrier selected from the group consisting of aprotinin, a biologically active aprotinin fragment, Angiopep-1, Angiopep-2 and biologically active analogs, derivatives or fragments thereof and a small molecule drug or a label,
  b) a pharmaceutically acceptable carrier, and;
  c) a solubilizer.

In accordance with the present invention, the solubilizer may be, for example, a poly-oxyethylene ester of fatty acid. Solubilizers encompassed by the present invention, include, for example, Solutol® HS-15.

An exemplary embodiment of the present invention, a suitable solubilizer may comprise, without limitation, a poly-oxyethylene ester of fatty acid such as for example, Solutol® HS-15.

In accordance with an embodiment of the invention, the pharmaceutical composition may be used more specifically for modifying the pharmacokinetics of a compound, for reducing the growth of a tumor cell or for the detection of a tumor cell, etc.

The present invention further relates to the use of at least one conjugate of the present invention for treating cancer, metastatic cancer and/or metastasis. In accordance with the present invention, an exemplary metastasis which may be treated using the conjugate of the present invention is a metastasis which may originate, for example and without limitation from a breast tumor, a lung tumor, a melanoma etc.

The present invention also provides in another aspect thereof, a method for treating a patient having a cancer (such as, for example, a primary tumor or a metastatic cancer and/or a metastasis) or for detecting a cancer cell, the method may comprise administering an individual with a pharmaceutical composition described herein or with a conjugate which may comprise a) a carrier which may be selected from the group consisting of aprotinin, a biologically active aprotinin fragment, Angiopep-1, Angiopep-2 and biologically active analogs, derivatives or fragments thereof and b) an anticancer drug or a label.

In accordance with the present invention, the individual may have, for example, an extracranial tumor, a primary brain tumor or a brain tumor of metastatic origin.

The method may also comprise a step of assessing whether the tumor of the individual comprises a multiple drug resistant tumor cell or for example a cell expressing P-gp (MDR1) or determining whether the tumor may have or has a multiple resistance drug phenotype.

The individual may be one which has a tumor. The individual may also be one which has received or which will receive chemotherapy or radiotherapy or both. The individual may also be one who has had surgery. Furthermore, the individual may be one that has a brain tumor or may also be one who has a tumor at another site than brain (is free of a brain tumor). An individual in need may also be, for example, an individual which present or is at risk of presenting, a resistance (a multiple drug resistance (MDR) phenotype) to at least one drug.

More particularly and in accordance with the present invention, the individual may have, for example, an extracranial tumor.

In accordance with the present invention, the extracranial tumor may be, for example, a lung tumor.

Also in accordance with the present invention, the extracranial tumor may be, for example, an extracranial metastasis from a brain tumor. In a more specific embodiment of the present invention, the extracranial brain tumor may be, for example, a glioblastoma (extracranial metastasis from glioblastoma).

In another particular embodiment of the present invention, the individual may have a brain tumor of metastatic origin. The brain tumor of metastatic origin may originate, for example, from a lung tumor. The brain tumor of metastatic origin may also originate, for example, from a breast tumor. Additionally, the brain tumor of metastatic origin may also originate, for example, from a melanoma. Furthermore and as described herein, the brain tumor of metastatic origin may also originate, for example, from a colorectal cancer. In addition, the brain tumor of metastatic origin may also originate, for example, from a urinary organ tumor.

In accordance with the present invention, the tumor may comprise a tumor cell which may be able to express P-gp or which expresses P-gp.

In accordance with the present invention the tumor may comprise a tumor cell which may be able to express LRP or which expresses LRP.

In accordance with the present invention, the tumor cell may comprise a tumor cell which may be able to co-express P-gp and LRP or which co-expresses P-gp and LRP. P-gp and LRP may be located, for example, at a cell surface.

More particularly, the present invention in an aspect thereof, relates to a method of promoting accumulation of a drug in the brain of an individual having a metastasis. The method may comprise administering a carrier or conjugate as described herein to an individual having a brain metastasis. In accordance with the present invention, the metastasis may originate from a lung cancer, etc.

The present invention provides in an additional aspect thereof, a method for promoting intracellular accumulation of a compound selected from the group consisting of a label, a protein, a peptide and a small molecule drug.

The method may comprise the step of contacting the cell or providing the cell with a conjugate which may comprise a) a carrier which may be selected from the group consisting of aprotinin, a biologically active aprotinin fragment, Angiopep-1, Angiopep-2 and biologically active analogs, derivatives or fragments thereof and b) the desired compound.

In accordance with the present invention, the cell may be, for example, a cell expressing P-gp.

Further in accordance with the present invention, the cell may be, for example, a brain cell, a lung cell, a breast cell, a kidney cell, an eye cell or a liver cell.

Also in accordance with the present invention, the cell may be, for example, a tumor cell which may be located outside of a brain of an individual (mammal, animal, etc.).

The present invention also provides in yet an additional aspect, a method for reducing the elimination of a drug from the inside of a cell which is able to express or which expresses P-gp (MDR1).

The method may comprise conjugating the drug with a carrier described herein, thereby forming a conjugate and providing the cell with the conjugate.

In an exemplary embodiment of the invention, the cell may be a multiple drug resistant cancer cell.

In a further exemplary embodiment of the invention, the cell may be comprised within an extracranial tumor of an individual.

In an additional exemplary embodiment of the invention, the cell may be comprised within a brain of an individual. The cell may be a tumor cell, such as for example a brain tumor cell (primary) or a metastatic brain tumor cell.

Means for providing a cell with a conjugate is, for example, to provide the conjugate to an individual who comprises a multiple drug resistant cell or a multiple drug resistant tumor cell (e.g. or a cell which expresses MDR1).

In accordance with the present invention the method may be used to reduce elimination of a drug which is a P-gp substrate or which may be a P-gp substrate.

In another aspect, the present invention provides a method for reducing the growth of a cell. The method may comprise contacting the cell with a conjugate which may comprise a) a carrier which may be selected from the group consisting of aprotinin, a biologically active aprotinin fragment, Angiopep-1, Angiopep-2 and biologically active analogs, derivatives and; b) a drug able to reduce the growth of a cell, or with the pharmaceutical composition described herein.

In accordance with the present invention the carrier may be used to increase the potency (efficiency, effectiveness) of the small molecule drug.

Also in accordance with the present invention, conjugation of the small molecule drug with the carrier may be achieved through several means which may include using a linker (e.g., a linker able to generate an ester bond) which may allow association of the drug through a suitable atom, for example, through an oxygen atom.

In an additional aspect the present invention provides a method for modifying the pharmacokinetics of a compound which may be selected, for example, from the group consisting of a label, a protein, a peptide and a small molecule drug, the method may comprise the step of conjugating the compound with a carrier described herein thereby forming a conjugate and providing the conjugate to an individual in need.

In accordance with the present invention, a ratio of one molecule of the compound for each carrier molecule may be used for the conjugation step.

Further in accordance with the present invention, a ratio of at least two molecules of the compound for each carrier molecule may be used for the conjugation step.

Also in accordance with the present invention, a ratio of at least three molecules of the compound for each carrier molecule may be used for the conjugation step.

In a particular embodiment of the invention, the compound may be, for example, a small molecule drug.

In another particular embodiment of the invention, the compound may be, for example, a label.

In accordance with the present invention, the individual in need may be, more particularly, an individual having a tumor. For example, the individual may have a brain tumor. In accordance with the present invention, the brain tumor may be, for example, a primary brain tumor. Also in accordance with the present invention, the brain tumor may be, for example, of a different tissue origin than brain tissue.

In an exemplary embodiment of the invention, the brain tumor of the individual may be, for example, an extracranial brain tumor.

In accordance with the present invention, the tumor may comprise a tumor cell expressing or which is able to express P-gp (MDR1).

The brain tumor may originate, for example, from a lung tumor. The brain tumor may also originate, for example, from a breast tumor. Also, for example, the brain tumor may originate from a melanoma.

In accordance with a particular embodiment of the present invention, the method may increase (optimize), for example, an anti-tumor growth effect of an anticancer drug (as compared with unconjugated drug).

In accordance with another particular embodiment of the present invention, the method may promote, for example, the accumulation of the compound within a cell (i.e., inside a cell).

In accordance with yet another particular embodiment of the present invention, the method may allow a reduction in the elimination of the small molecule drug from the inside of a cell (e.g., a cell expressing P-gp).

In accordance with an additional embodiment of the present invention, the method may allow a reduction of cell growth (e.g., reduction of tumor cell growth).

Furthermore, the method may allow an improvement in the bioavailability of the small molecule drug.

In addition and in accordance with the present invention, the method may be used to change the (usual) tissue distribution of the small molecule drug.

In yet a further aspect, the present invention provides for the use of a carrier, conjugate or the pharmaceutical composition as described herein for reducing LRP-dependent accumulation of RAP and for reducing RAP-mediated cellular (e.g., intracellular) event or effect.

For the purpose of the present invention the following terms are defined below.

The term "Angiopep" as used herein refers to Angiopep-1 and Angiopep-2.

The terms "Taxol-Angiopep" and "TxlAn" are used interchangeably and refer to Taxol-Angiopep-1 and Taxol-Angiopep-2, comprising 1, 2 or 3 Taxol molecules.

The terms "Taxol-Angiopep-1" and "TxlAn1" are used interchangeably and refer to Taxol-Angiopep-1, comprising either 1, 2 or 3 Taxol molecules.

The terms "Taxol-Angiopep-2" and "TxlAn2" are used interchangeably and refer to Taxol-Angiopep-2, comprising either 1, 2 or 3 Taxol molecules.

The term "TxlAn1 (2:1)" refers to the ratio of Taxol over Angiopep-1 molecules in a given conjugate. For example, the term "TxlAn1 (2:1) relates to a conjugate having 2 molecules of Taxol associated with one molecule of Angiopep-1. In addition, the term "TxlAn1 (3:1) relates to a conjugate having 3 molecules of Taxol associated with one molecule of Angiopep-1.

Similarly, the term "TxlAn2 (2:1)" refers to the ratio of Taxol over Angiopep-2 molecules in a given conjugate. For example, the term "TxlAn2 (2:1) relates to a conjugate having 2 molecules of Taxol associated with one molecule of Angiopep-2. In addition, the term "TxlAn2 (3:1) relates to a conjugate having 3 molecules of Taxol associated with one molecule of Angiopep-2.

The term "carrier" or "vector" is intended to mean a compound or molecule that is able to transport a molecule at a desired targeted site or cell. A carrier may be attached to (covalently or not) or conjugated to another compound or agent and thereby may be able to transport the other compound or agent a desired targeted site. The carrier may be, but is not limited to, a protein, a peptide or to a peptidomimetic and can be naturally occurring or produced by chemical synthesis or recombinant genetic technology (genetic engineering).

The expression "small molecule drug" is intended to mean a drug having a molecular weight of 1000 g/mol or less or between 300 and 700 g/mol.

The terms "treatment", "treating" and the like are intended to mean obtaining a desired pharmacologic and/or physiologic effect, e.g., inhibition of cancer cell growth, death of a cancer cell or amelioration of a neurological disease or condition. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, particularly a human, and includes: (a) preventing a disease (e.g., preventing cancer) or condition from occurring in an individual who may be predisposed to the disease but has not yet been diagnosed as having it; (b) inhibiting a disease, (e.g., arresting its development); or (c) relieving a disease (e.g., reducing symptoms associated with a disease). "Treatment" as used herein covers any administration of a pharmaceutical agent or compound to an individual to treat, cure, alleviate, improve, diminish or inhibit a condition in the individual, including, without limitation, administering a drug comprising a carrier described herein or a conjugate to an individual in need thereof.

The term "cancer" is intended to mean any cellular malignancy whose unique trait is the loss of normal controls which results in unregulated growth, lack of differentiation and ability to invade local tissues and metastasize. Cancer can develop in any tissue of any organ. More specifically, cancer is intended to include, without limitation, cancer of the brain.

The term "administering" and "administration" is intended to mean a mode of delivery including, without limitation, intra-arterially, intra-nasally, intra-peritoneally, intravenously, intramuscularly, sub-cutaneously, transdermally or per os. A daily dosage may be divided into one, two or more doses in a suitable form to be administered at one, two or more times throughout a time period.

The term "therapeutically effective" or "effective amount" is intended to mean an amount of a compound sufficient to substantially improve some symptom associated with a disease or a medical condition. For example, in the treatment of cancer, an agent or compound which decreases, prevents, delays, suppresses, or arrests any symptom of the disease or condition would be therapeutically effective. A therapeutically effective amount of an agent or compound is not required to cure a disease or condition but will provide a treatment for a disease or condition such that the onset of the disease or condition is delayed, hindered, or prevented, or the disease or condition symptoms are ameliorated, or the term of the disease or condition is changed or, for example, is less severe or recovery is accelerated in an individual.

The carrier and conjugate of the present invention may be used in combination with either conventional methods of treatment and/or therapy or may be used separately from conventional methods of treatment and/or therapy.

When the conjugates of this invention are administered in combination therapies with other agents, they may be administered sequentially or concurrently to an individual. Alternatively, pharmaceutical compositions according to the present invention may be comprised of a combination of a carrier-agent conjugate of the present invention in association with a pharmaceutically acceptable carrier or pharmaceutically acceptable excipient, as described herein, and another therapeutic or prophylactic agent known in the art.

Pharmaceutically acceptable acid (addition) salts may be prepared by methods known and used in the art.

As used herein, "pharmaceutical composition" means therapeutically effective amounts of the agent together with pharmaceutically acceptable diluents, preservatives, solubilizers, emulsifiers, adjuvant and/or carriers. A "therapeutically effective amount" as used herein refers to that amount which provides a therapeutic effect for a given condition and administration regimen. Such compositions are liquids or lyophilized or otherwise dried formulations and include diluents of various buffer content (e.g., Tris-HCl, acetate, phosphate), pH and ionic strength, additives such as albumin or gelatin to prevent absorption to surfaces, detergents (e.g., Tween 20, Tween 80, Pluronic F68, bile acid salts). Solubilizing agents (e.g., glycerol, polyethylene glycerol), antioxidants (e.g., ascorbic acid, sodium metabisulfite), preservatives (e.g., thimerosal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polyglycolic acid, hydrogels, etc, or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance. Controlled or sustained release compositions include formulation in lipophilic depots (e.g., fatty acids, waxes, oils). Also comprehended by the invention are particulate compositions coated with polymers (e.g., poloxamers or poloxamines). Other embodiments of the compositions of the invention incorporate particulate forms protective coatings, protease inhibitors or permeation enhancers for various routes of administration, including parenteral, pulmonary, nasal, oral, vaginal, rectal routes. In one embodiment the pharmaceutical composition is administered parenterally, paracancerally, transmucosally, transdermally, intramuscularly, intravenously, intradermally, subcutaneously, intraperitonealy, intraventricularly, intracranially and intratumorally.

Further, as used herein "pharmaceutically acceptable carrier" or "pharmaceutical carrier" are known in the art and include, but are not limited to, 0.01-0.1 M or 0.05 M phosphate buffer or 0.8% saline. Additionally, such pharmaceutically acceptable carriers may be a buffer, an aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's orfixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like.

A "fragment" is to be understood herein as a polypeptide originating from (encompassing) a portion of an original or parent sequence. Fragments encompass polypeptides having truncations of one or more amino acids, wherein the truncation may originate from the amino terminus (N-terminus), carboxy terminus (C-terminus), or from the interior of the protein. A fragment may comprise the same sequence as the corresponding portion of the original sequence. Biologically active fragments of the carrier described herein are encompassed by the present invention.

A "derivative" in the context of proteins or peptides is to be understood herein as a polypeptide originating from an original sequence or from a portion of an original sequence and which may comprise one or more modification; for example, one or more modification in the amino acid sequence (e.g., an amino acid addition, deletion, insertion, substitution etc.) and one or more modification in the backbone or side-chain of one or more amino acid, or an addition of a group or another molecule to one or more amino acids (side-chains or backbone). Biologically active derivatives of the carrier described herein are encompassed by the present invention.

An "analogue" in the context of proteins or peptides is to be understood herein as a molecule having a biological activity and chemical structure similar to that of a polypeptide described herein. An analog comprises a polypeptide which may have, for example, one or more amino acid insertion, either at one or both of the end of the polypeptide and/or inside the amino acid sequence of the polypeptide.

An "analogue" may have sequence similarity with that of an original sequence or a portion of an original sequence and may also have a modification of its structure as discussed herein. For example, an "analogue" may have at least 90% sequence similarity with an original sequence or a portion of an original sequence. An "analogue" may also have, for example; at least 70% or even 50% sequence similarity with an original sequence or a portion of an original sequence. An "analogue" may have, for example, 50%, 70%, 80% or 90% sequence similarity to an original sequence with a combination of one or more modification in a backbone or side-chain of an amino acid, or an addition of a group or another molecule, etc. Amino acids which are intended to be similar (a conservative amino acid) to another are known in the art and includes, for example, those listed in Table 1.

In addition, an "analogue" may have at least 50%, 70%, 80% or 90% sequence identity with an original sequence or a portion of an original sequence. Also, an "analogue" may have, for example, 50%, 70%, 80% or 90% sequence identity to an original sequence with a combination of one or more modification in a backbone or side-chain of an amino acid, or an addition of a group or another molecule, etc.

Similarity or identity may be compared, for example, over a region of 2, 3, 4, 5, 10, 19, 20 amino acids or more (and any number therebetween). Identity may include herein, amino acids which are identical to the original peptide and which may occupy the same or similar position when compared to the original polypeptide. An analog which have, for example, 50% identity with an original polypeptide may include for example, an analog comprising 50% of the amino acid of the original polypeptide and similarly with the other percentages. It is to be understood herein that gaps may be found between the amino acids of an analogs which are identical or similar to amino acids of the original peptide. The gaps may include no amino acids, one or more amino acids which are not identical or similar to the original peptide. Biologically active analogs of the carrier of the present invention are encompassed herewith.

Thus, biologically active polypeptides in the form of the original polypeptides, fragments (modified or not), analogues (modified or not), derivatives (modified or not), homologues, (modified or not) of the carrier described herein are encompassed by the present invention.

Therefore, any polypeptide having a modification compared to an original polypeptide which does not destroy significantly a desired biological activity is encompassed herein. It is well known in the art, that a number of modifications may be made to the polypeptides of the present invention without deleteriously affecting their biological activity. These modifications may, on the other hand, keep or increase the biological activity of the original polypeptide or may optimize one or more of the particularity (e.g. stability, bioavailability, etc.) of the polypeptides of the present invention which, in some instance might be needed or desirable. Polypeptides of the present invention comprises for example, those containing amino acid sequences modified either by natural processes, such as posttranslational processing, or by chemical modification techniques which are known in the art. Modifications may occur anywhere in a polypeptide including the polypeptide backbone, the amino acid side-chains and the amino- or carboxy-terminus. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from posttranslational natural processes or may be made by synthetic methods. Modifications comprise for example, without limitation, pegylation, acetylation, acylation, addition of acetomidomethyl (Acm) group, ADP-ribosylation, alkylation, amidation, biotinylation, carbamoylation, carboxyethylation, esterification, covalent attachment to flavin, covalent attachment to a heme moiety, covalent attachment of a nucleotide or nucleotide derivative, covalent attachment of drug, covalent attachment of a marker (e.g., fluorescent, radioactive, etc.), covalent attachment of a lipid or lipid derivative, covalent attachment of phosphatidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation and ubiquitination, etc. It is to be understood herein that more than one modification to the polypeptides described herein are encompassed by the present invention to the extent that the biological activity is similar to the original (parent) polypeptide.

As discussed above, polypeptide modification may comprise, for example, amino acid insertion (i.e., addition), deletion and substitution (i.e., replacement), either conservative or non-conservative (e.g., D-amino acids, desamino acids) in the polypeptide sequence where such changes do not substantially alter the overall biological activity of the polypeptide.

Example of substitutions may be those, which are conservative (i.e., wherein a residue is replaced by another of the same general type or group) or when wanted, non-conservative (i.e., wherein a residue is replaced by an amino acid of another type). In addition, a non-naturally occurring amino acid may substitute for a naturally occurring amino acid (i.e., non-naturally occurring conservative amino acid substitution or a non-naturally occurring non-conservative amino acid substitution).

As is understood, naturally occurring amino acids may be sub-classified as acidic, basic, neutral and polar, or neutral and non-polar. Furthermore, three of the encoded amino acids are aromatic. It may be of use that encoded polypeptides differing from the determined polypeptide of the present invention contain substituted codons for amino acids, which are from the same type or group as that of the amino acid to be replaced. Thus, in some cases, the basic amino acids Lys, Arg and His may be interchangeable; the acidic amino acids Asp and Glu may be interchangeable; the neutral polar amino acids Ser, Thr, Cys, Gln, and Asn may be interchangeable; the non-polar aliphatic amino acids Gly, Ala, Val, Ile, and Leu are interchangeable but because of size Gly and Ala are more closely related and Val, Ile and Leu are more closely related to each other, and the aromatic amino acids Phe, Trp and Tyr may be interchangeable.

It should be further noted that if the polypeptides are made synthetically, substitutions by amino acids, which are not naturally encoded by DNA (non-naturally occurring or unnatural amino acid) may also be made.

A non-naturally occurring amino acid is to be understood herein as an amino acid which is not naturally produced or found in a mammal. A non-naturally occurring amino acid comprises a D-amino acid, an amino acid having an acetylaminomethyl group attached to a sulfur atom of a cysteine, a pegylated amino acid, etc. The inclusion of a non-naturally occurring amino acid in a defined polypeptide sequence will therefore generate a derivative of the original polypeptide. Non-naturally occurring amino acids (residues) include also the omega amino acids of the formula $NH_2(CH_2)_nCOOH$ wherein n is 2-6, neutral nonpolar amino acids, such as sarcosine, t-butyl alanine, t-butyl glycine, N-methyl isoleucine, norleucine, etc. Phenylglycine may substitute for Trp, Tyr or Phe; citrulline and methionine sulfoxide are neutral nonpolar, cysteic acid is acidic, and ornithine is basic. Proline may be substituted with hydroxyproline and retain the conformation conferring properties.

It is known in the art that analogues may be generated by substitutional mutagenesis and retain the biological activity of the polypeptides of the present invention. These analogues have at least one amino acid residue in the protein molecule removed and a different residue inserted in its place. Examples of substitutions identified as "conservative substitutions" are shown in Table 1. If such substitutions result in a change not desired, then other type of substitutions, denominated "exemplary substitutions" in Table 1, or as further described herein in reference to amino acid classes, are introduced and the products screened.

In some cases it may be of interest to modify the biological activity of a polypeptide by amino acid substitution, insertion, or deletion. For example, modification of a polypeptide may result in an increase in the polypeptide's biological activity, may modulate its toxicity, may result in changes in bioavailability or in stability, or may modulate its immunological activity or immunological identity. Substantial modifications in function or immunological identity are accomplished by selecting substitutions that differ significantly in their effect on maintaining (a) the structure of the polypeptide backbone in the area of the substitution, for example, as a sheet or helical conformation. (b) the charge or hydrophobicity of the molecule at the target site, or (c) the bulk of the side chain. Naturally occurring residues are divided into groups based on common side chain properties:

(1) hydrophobic: norleucine, methionine (Met), Alanine (Ala), Valine (Val), Leucine (Leu), Isoleucine (Ile)

(2) neutral hydrophilic: Cysteine (Cys), Serine (Ser), Threonine (Thr)

(3) acidic: Aspartic acid (Asp), Glutamic acid (Glu)

(4) basic: Asparagine (Asn), Glutamine (Gln), Histidine (His), Lysine (Lys), Arginine (Arg)

(5) residues that influence chain orientation: Glycine (Gly), Proline (Pro); and aromatic: Tryptophan (Trp), Tyrosine (Tyr), Phenylalanine (Phe)

Non-conservative substitutions will entail exchanging a member of one of these classes for another.

TABLE 1 amino acid substitution

| Original residue | Exemplary substitution | Conservative substitution |
|---|---|---|
| Ala (A) | Val, Leu, Ile | Val |
| Arg (R) | Lys, Gln, Asn | Lys |
| Asn (N) | Gln, His, Lys, Arg | Gln |
| Asp (D) | Glu | Glu |
| Cys (C) | Ser | Ser |
| Gln (Q) | Asn | Asn |
| Glu (E) | Asp | Asp |
| Gly (G) | Pro | Pro |
| His (H) | Asn, Gln, Lys, Arg | Arg |
| Ile (I) | Leu, Val, Met, Ala, Phe, norleucine | Leu |
| Leu (L) | Norleucine, Ile, Val, Met, Ala, Phe | Ile |
| Lys (K) | Arg, Gln, Asn | Arg |
| Met (M) | Leu, Phe, Ile | Leu |
| Phe (F) | Leu, Val, Ile, Ala | Leu |
| Pro (P) | Gly | Gly |
| Ser (S) | Thr | Thr |
| Thr (T) | Ser | Ser |
| Trp (W) | Tyr | Tyr |
| Tyr (Y) | Trp, Phe, Thr, Ser | Phe |
| Val (V) | Ile, Leu, Met, Phe, Ala, norleucine | Leu |

A biologically active analog may be, for example, an analogue having at least one conservative amino acid substitution in the original sequence. A biologically active analog may also be for example, an analog having an insertion of an amino acid.

For example, an Angiopep-1 analog may have the formula I: $X_1$-Angiopep-1-$X_2$ For example, an Angiopep-2 analog may have the formula II: $X_1$-Angiopep-2-$X_2$ $X_1$ and $X_2$ may independently be an amino acid sequence of from between 0 to about 100 (e.g., from between 0 to about 60) amino acids. $X_1$ and $X_2$ may be derived from consecutive amino acids of aprotinin or aprotinin analogs (homologous amino acid sequence) or may be any other amino acid sequence (heterologous amino acid sequence).

A compound of either formula I or II, may also comprises an amino acid substitution, deletion or insertion within the amino acid sequence of Angiopep-1 or Angiopep-2. The analog however would preferably be biologically active as determined by one of the assays described herein or by any similar or equivalent assays.

Examples of aprotinin analogs may be found by performing a protein blast (Genebank: www.ncbi.nlm.nih.gov/BLAST/) of the synthetic aprotinin sequence (or portion thereof) disclosed in international application no. PCT/CA2004/000011. Exemplary aprotinin analogs may be found, for example under accession nos. CAA37967 (GI: 58005), 1405218C (GI:3604747) etc.

A biologically active fragment of a polypeptide (e.g., of 19 amino acids) described herein may include for example a polypeptide of from about 7, 8, 9 or 10 to 18 amino acids.

A biologically active polypeptide (e.g., carrier) may be identified by using one of the assays or methods described herein. For example a candidate carrier may be produced by conventional peptide synthesis, conjugated with Taxol as described herein and tested in an in vivo model as described in Example 5. A biologically active carrier may be identified, for example, based on its efficacy at reducing tumor burden compared to placebo-treated mice. A small molecule drug candidate which may be used in the conjugation of a carrier described herein may be identified, for example, by determining or not whether the drug is expulsed from P-gp over-expressing cells as described herein and evaluating whether its conjugation to the carrier increases its accumulation inside a desired cell.

Examples of biologically active carrier (i.e., biologically active analog of Angiopep-1 and/or Angiopep-2) may include for example, peptides derived from the kunitz-domain such as TFFYGGCRGKRNNFKTKEY (SEQ ID NO: 76), RFKYGGCLGNKNNYLRLKY (SEQ ID NO: 91) and TFFYGGCRAKRNNFKRAKY (SEQ ID NO: 5). Other examples of biologically active analogs may be found in Table 2A and 2B and in the Sequence Listing.

TABLE 2A

Design of 96 peptides from similar domain to aprotinin and Angiopep-1 with different charges and amino acid insertions (SEQ ID NOS:1-96)

96 PEPTIDES ORDERED AT SYNPEP (California, USA)

| Proteins | Characteristics | #Pep SEQ ID NO: | 1 | 2 | 3 | 4 | 5 | 6 | 7 | 8 | 9 | 10 | 11 | 12 | 13 | 14 | 15 | 16 | 17 | 18 | 19 | 20 | 21 | 22 |
|---|---|---|---|---|---|---|---|---|---|---|---|---|---|---|---|---|---|---|---|---|---|---|---|---|
| Aprot-synth | CHARGE (+6) | 1 | T | F | V | Y | G | G | C | R | A | K | R | N | N | F | K | S | A | E | D | | | |
| Blkunin HI-30 | | 2 | T | F | Q | Y | G | G | C | M | G | N | G | N | N | F | V | T | E | K | E | | | |
| Amyloid | | 3 | P | F | F | Y | G | G | C | G | G | N | R | N | N | F | D | T | E | E | Y | | | |
| Kunitz-Inhib 1 | | 4 | S | F | Y | Y | G | G | C | L | G | N | K | N | N | Y | L | R | E | E | E | | | |
| Peptides | | 5 | T | F | F | Y | G | G | C | R | A | K | R | N | N | F | K | R | A | K | Y | | | |
| | | 6 | T | F | F | Y | G | G | C | R | G | K | R | N | N | F | K | R | A | K | Y | | | |
| | | 7 | T | F | F | Y | G | G | C | R | A | K | K | N | N | Y | K | R | A | K | Y | | | |
| | | 8 | T | F | F | Y | G | G | C | R | G | K | K | N | N | F | K | R | A | K | Y | | | |
| | | 9 | T | F | Q | Y | G | G | C | R | A | K | R | N | N | F | K | R | A | K | Y | | | |
| | | 10 | T | F | Q | Y | G | G | C | R | G | K | K | N | N | F | K | R | A | K | Y | | | |
| | CHARGE (+5) | 11 | T | F | F | Y | G | G | C | L | G | K | R | N | N | F | K | R | A | K | Y | | | |
| | | 12 | T | F | F | Y | G | G | S | L | G | K | R | N | N | F | K | R | A | K | Y | | | |
| | | 13 | P | F | F | Y | G | G | C | G | G | K | N | N | N | F | K | R | A | K | Y | | | |
| | | 14 | T | F | F | Y | G | G | C | R | G | K | G | N | N | Y | K | R | A | K | Y | | | |
| | | 15 | P | F | F | Y | G | G | C | R | G | K | R | N | N | F | L | R | A | K | Y | | | |
| | | 16 | T | F | F | Y | G | G | C | R | G | K | R | N | N | F | K | R | E | K | Y | | | |
| | | 17 | P | F | F | Y | G | G | C | R | A | K | K | N | N | F | K | R | A | K | E | | | |
| | | 18 | T | F | F | Y | G | G | C | R | G | K | R | N | N | F | K | R | A | K | D | | | |

TABLE 2A-continued

Design of 96 peptides from similar domain to aprotinin and Angiopep-1 with different charges and amino acid insertions (SEQ ID NOS:1-96)

96 PEPTIDES ORDERED AT SYNPEP (California, USA)

| Proteins | Characteristics | #Pep SEQ ID NO: | 1 | 2 | 3 | 4 | 5 | 6 | 7 | 8 | 9 | 10 | 11 | 12 | 13 | 14 | 15 | 16 | 17 | 18 | 19 | 20 | 21 | 22 |
|---|---|---|---|---|---|---|---|---|---|---|---|---|---|---|---|---|---|---|---|---|---|---|---|---|
| | CHARGE (+4) | 19 | T | F | F | Y | G | G | C | R | A | K | R | N | N | F | D | R | A | K | Y | | | |
| | | 20 | T | F | F | Y | G | G | C | R | G | K | K | N | N | F | K | R | A | E | Y | | | |
| | | 21 | P | F | F | Y | G | G | C | G | A | N | R | N | N | F | K | R | A | K | Y | | | |
| | | 22 | T | F | F | Y | G | G | C | G | G | K | K | N | N | F | K | T | A | K | Y | | | |
| | | 23 | T | F | F | Y | G | G | C | R | G | N | R | N | N | F | L | R | A | K | Y | | | |
| | | 24 | T | F | F | Y | G | G | C | R | G | N | R | N | N | F | K | T | A | K | Y | | | |
| | | 25 | T | F | F | Y | G | G | S | R | G | N | R | N | N | F | K | T | A | K | Y | | | |
| | CHARGE (+3) | 26 | T | F | F | Y | G | G | C | L | G | N | G | N | N | F | K | R | A | K | Y | | | |
| | | 27 | T | F | F | Y | G | G | C | L | G | N | R | N | N | F | L | R | A | K | Y | | | |
| | | 28 | T | F | F | Y | G | G | C | L | G | N | R | N | N | F | K | T | A | K | Y | | | |
| | | 29 | T | F | F | Y | G | G | C | R | G | N | G | N | N | F | K | S | A | K | Y | | | |
| | | 30 | T | F | F | Y | G | G | C | R | G | K | K | N | N | F | D | R | E | K | Y | | | |
| | | 31 | T | F | F | Y | G | G | C | R | G | K | R | N | N | F | L | R | E | K | E | | | |
| | | 32 | T | F | F | Y | G | G | C | R | G | K | G | N | N | F | D | R | A | K | Y | | | |
| | | 33 | T | F | F | Y | G | G | S | R | G | K | G | N | N | F | D | R | A | K | Y | | | |
| | CHARGE (+2) | 34 | T | F | F | Y | G | G | C | R | G | N | G | N | N | F | V | T | A | K | Y | | | |
| | | 35 | P | F | F | Y | G | G | C | G | G | K | G | N | N | Y | V | T | A | K | Y | | | |
| | | 36 | T | F | F | Y | G | G | C | L | G | K | G | N | N | F | L | T | A | K | Y | | | |
| | | 37 | S | F | F | Y | G | G | C | L | G | N | K | N | N | F | L | T | A | K | Y | | | |
| | HUMAN | 38 | T | F | F | Y | G | G | C | G | G | N | K | N | N | F | V | R | E | K | Y | | | |
| | HUMAN | 39 | T | F | F | Y | G | G | C | M | G | N | K | N | N | F | V | R | E | K | Y | | | |
| | HUMAN | 40 | T | F | F | Y | G | G | S | M | G | N | K | N | N | F | V | R | E | K | Y | | | |
| | HUMAN | 41 | P | F | F | Y | G | G | C | L | G | N | R | N | N | Y | V | R | E | K | Y | | | |
| | HUMAN | 42 | T | F | F | Y | G | G | C | L | G | N | R | N | N | F | V | R | E | K | Y | | | |
| | HUMAN | 43 | T | F | F | Y | G | G | C | L | G | N | K | N | N | Y | V | R | E | K | Y | | | |
| | CHARGE (+1) | 44 | T | F | F | Y | G | G | C | G | G | N | G | N | N | F | L | T | A | K | Y | | | |
| | | 45 | T | F | F | Y | G | G | C | R | G | N | R | N | N | F | L | T | A | E | Y | | | |
| | | 46 | T | F | F | Y | G | G | C | R | G | N | G | N | N | F | K | S | A | E | Y | | | |
| | | 47 | P | F | F | Y | G | G | C | L | G | N | K | N | N | F | K | T | A | E | Y | | | |
| | | 48 | T | F | F | Y | G | G | C | R | G | N | R | N | N | F | K | T | E | E | Y | | | |
| | | 49 | T | F | F | Y | G | G | C | R | G | K | R | N | N | F | K | T | E | E | D | | | |
| | HUMAN | 50 | P | F | F | Y | G | G | C | G | G | N | G | N | N | F | V | R | E | K | Y | | | |
| | HUMAN | 51 | S | F | F | Y | G | G | C | M | G | N | G | N | N | F | V | R | E | K | Y | | | |
| | HUMAN | 52 | P | F | F | Y | G | G | C | G | G | N | G | N | N | F | L | R | E | K | Y | | | |
| | HUMAN | 53 | T | F | F | Y | G | G | C | L | G | N | G | N | N | F | V | R | E | K | Y | | | |
| | HUMAN | 54 | S | F | F | Y | G | G | C | L | G | N | G | N | N | Y | L | R | E | K | Y | | | |
| | HUMAN | 55 | T | F | F | Y | G | G | S | L | G | N | G | N | N | F | V | R | E | K | Y | | | |
| | CHARGE (+0) | 56 | T | F | F | Y | G | G | C | R | G | N | G | N | N | F | V | T | A | E | Y | | | |
| | | 57 | T | F | F | Y | G | G | C | L | G | K | G | N | N | F | V | S | A | E | Y | | | |
| | | 58 | T | F | F | Y | G | G | C | L | G | N | R | N | N | F | D | R | A | E | Y | | | |
| | HUMAN | 59 | T | F | F | Y | G | G | C | L | G | N | R | N | N | F | L | R | E | E | Y | | | |
| | HUMAN | 60 | T | F | F | Y | G | G | C | L | G | N | K | N | N | Y | L | R | E | E | Y | | | |
| | HUMAN | 61 | P | F | F | Y | G | G | C | G | G | N | R | N | N | Y | L | R | E | E | Y | | | |
| | HUMAN | 62 | P | F | F | Y | G | G | S | G | G | N | R | N | N | Y | L | R | E | E | Y | | | |
| Aprotinin | vs APROTININ M-term | 63 | M | R | P | D | F | C | L | E | P | P | Y | T | G | P | C | V | A | R | I | | | |
| | (1 helix α, A-term) | 64 | A | R | I | I | R | Y | F | Y | N | A | K | A | G | L | C | Q | T | F | V | Y | G | |
| | (2β sheets, Y-term) | 65 | Y | G | G | C | R | A | K | R | N | N | Y | K | S | A | E | D | C | M | R | T | C | G |
| | (1α, 1β) | 66 | P | D | G | C | L | E | P | P | Y | T | G | P | C | V | A | R | I | I | R | Y | F | Y |
| AngloPep | AngloPep-1 | 67 | T | F | F | Y | G | G | C | R | G | K | R | N | N | F | K | T | E | E | Y | | | |
| | AngloPEP1 (lysine) | 68 | K | F | F | Y | G | G | C | R | G | K | R | N | N | F | K | T | E | E | Y | | | |
| | AngloPEP1 (4Y) | 69 | T | F | Y | Y | G | G | C | R | G | K | R | N | N | Y | K | T | E | E | Y | | | |
| | cys bridge | 70 | T | F | F | Y | G | G | S | R | G | K | R | N | N | F | K | T | E | E | Y | | | |
| | cys-Nterminal | 71 | C | T | F | F | Y | G | C | R | G | K | R | N | N | F | K | T | E | E | Y | | | |
| | cys-Cterminal | 72 | T | F | F | Y | G | G | C | R | G | K | R | N | N | F | K | T | E | E | Y | C | | |
| | cys-Nterminal | 73 | C | T | F | F | Y | G | S | C | R | G | K | R | N | N | F | K | T | E | E | Y | | |
| | cys-Cterminal | 74 | T | F | F | Y | G | G | S | R | G | K | R | N | N | F | K | T | E | E | Y | C | | |
| | pro | 75 | P | F | F | Y | G | G | C | R | G | K | R | N | N | F | K | T | E | E | Y | | | |
| | charge (+3) | 76 | T | F | F | Y | G | G | C | R | G | K | R | N | N | F | K | T | K | E | Y | | | |
| | charge (+3)-cys | 77 | T | F | F | Y | G | G | K | R | G | K | R | N | N | F | K | T | E | E | Y | | | |
| | charge (+4) | 78 | T | F | F | Y | G | G | C | R | G | K | R | N | N | F | K | T | K | R | Y | | | |
| | charge (+4)-cys | 79 | T | F | F | Y | G | G | K | R | G | K | R | N | N | F | K | T | A | E | Y | | | |
| | charge (+5) | 80 | T | F | F | Y | G | G | K | R | G | K | R | N | N | F | K | T | A | G | Y | | | |
| | charge (+6) | 81 | T | F | F | Y | G | G | K | R | G | K | R | N | N | F | K | R | E | K | Y | | | |
| | charge (+7) | 82 | T | F | F | Y | G | G | K | R | G | K | R | N | N | F | K | R | A | K | Y | | | |
| | charge (0) | 83 | T | F | F | Y | G | G | C | L | G | N | R | N | N | F | K | T | E | E | Y | | | |
| | permut cys(−) | 84 | T | F | F | Y | G | C | G | R | G | K | R | N | N | F | K | T | E | E | Y | | | |
| | permut cys(+) | 85 | T | F | F | Y | G | G | R | C | G | K | R | N | N | F | K | T | E | E | Y | | | |
| | charge (−4) | 86 | T | F | F | Y | G | G | C | L | G | N | G | N | N | F | D | T | E | E | E | | | |
| | Q instead of F | 87 | T | F | Q | Y | G | G | C | R | G | K | R | N | N | F | K | T | E | E | Y | | | |

TABLE 2A-continued

Design of 96 peptides from similar domain to aprotinin and Angiopep-1 with different charges and amino acid insertions (SEQ ID NOS:1-96)

96 PEPTIDES ORDERED AT SYNPEP (California, USA)

| Proteins | Characteristics | #Pep SEQ ID NO: | 1 | 2 | 3 | 4 | 5 | 6 | 7 | 8 | 9 | 10 | 11 | 12 | 13 | 14 | 15 | 16 | 17 | 18 | 19 | 20 | 21 | 22 |
|---|---|---|---|---|---|---|---|---|---|---|---|---|---|---|---|---|---|---|---|---|---|---|---|---|
| | ANGIOPEP scramble | 88 | Y | N | K | E | F | G | T | F | N | T | K | G | C | E | R | G | Y | R | F | | | |
| TFPI | TFPI (similar domain) | 89 | R | F | K | Y | G | G | C | L | G | N | M | N | N | F | E | T | L | E | E | | | |
| | Charge+5 (HUMAN) | 90 | R | F | K | Y | G | G | C | L | G | N | K | N | N | F | L | R | L | K | Y | | | |
| | Charge+5 (HUMAN) | 91 | R | F | K | Y | G | G | C | L | G | N | K | N | N | Y | L | R | L | K | Y | | | |
| | TFPI (c-terminal) (2Y) | 92 | K | T | K | R | K | R | K | K | Q | R | V | K | I | A | Y | E | E | I | F | K | N | Y |
| | TFPI (c-terminal tronque) | 93 | K | T | K | R | K | R | K | K | Q | R | V | K | I | A | Y | | | | | | | |
| Basic-Peptides | SynB1 | 94 | R | G | G | R | L | S | Y | S | R | R | F | S | T | S | T | G | R | | | | | |
| | SynB3 | 95 | R | R | L | S | Y | S | R | R | R | F | | | | | | | | | | | | |
| | Penetratin (pAntp43-68) | 96 | R | Q | I | K | I | W | F | Q | N | R | M | K | W | K | K | | | | | | | |

TABLE 2B

| Peptide Name | Peptide Sequences | Reactive amines (positions) | Charge | SEQ ID No. |
|---|---|---|---|---|
| Angiopep 1 | TFFYGGCRGKRNN FKTEEY | 3 and 1 cyst (1, 10, 15, 7) | +2 | 67 |
| Angiopep-2 | TFFYGGSRGKRNN FKTEEY | 3 (1, 10, 15) | +2 | 97 |
| Angiopep-3* | Ac¹-TFFYGGSRG KRNNFKTEEY | 2 (10, 15) | +1 | 107 |
| Angiopep-4b | RFFYGGSRGKR NNFKTEEY | 3 (1, 10, 15) | +3 | 108 |
| Angiopep-4a | Ac¹-RFFYGGSR GKRNNFKTEEY | 2 (10, 15) | +2 | 109 |
| Angiopep-5 | Ac¹-RFFYGGSR GKRNNFRTEEY | 1 (10) | +2 | 110 |
| Angiopep-6 | TFFYGGSRGKR NNFRTEEY | 2 (1, 10) | +2 | 111 |
| Angiopep-7 | TFFYGGSRGRR NNFRTEEY | 1 (1) | +2 | 112 |

*Angiopep-3 is an acetylated form of Angiopep-2.
¹Ac represents acetylation.

It is to be understood herein, that if a "range" or "group of substances" is mentioned with respect to a particular characteristic (e.g., temperature, concentration, time and the like) of the present invention, the present invention relates to and explicitly incorporates herein each and every specific member and combination of sub-ranges or sub-groups therein whatsoever. Thus, any specified range or group is to be understood as a shorthand way of referring to each and every member of a range or group individually as well as each and every possible sub-ranges or sub-groups encompassed therein; and similarly with respect to any sub-ranges or sub-groups therein. Thus, for example, with respect to a length of 19 amino acid long or less, is to be understood as specifically incorporating herein each and every individual length, e.g., a length of 18, 17, 15, 10, 5, etc.; Therefore, unless specifically mentioned, every range mentioned herein is to be understood as being inclusive. For example, in the expression from 5 to 19 amino acids long is to be as including 5 and 19;

and similarly with respect to other parameters such as sequences, length, concentrations, elements, etc. . . .

It is in particular to be understood herein that the sequences, regions, portions defined herein each include each and every individual sequences, regions, portions described thereby as well as each and every possible sub-sequences, sub-regions, sub-portions whether such sub-sequences, sub-regions, sub-portions is defined as positively including particular possibilities, as excluding particular possibilities or a combination thereof; for example an exclusionary definition for a region may read as follows: "provided that said polypeptide is no shorter than 4, 5, 6, 7, 8 or 9 amino acids. Yet a further example of a negative limitation is the following; a sequence comprising SEQ ID NO.: X with the exclusion of a polypeptide of SEQ ID NO. Y.; etc. Other examples of exemplary negative limitations are the following; "other than brain cancer" or "other than brain tissue" or "other than brain cells".

BRIEF DESCRIPTION OF THE DRAWINGS

In drawings which illustrates exemplary embodiments of the invention,

FIG. 1. is an amino sequence of aprotinin-derived peptides;

FIGS. 16A and 16B are pictures representing immunodetection of LRP in human brain tumor biopsies;

DETAILED DESCRIPTION OF THE INVENTION

Figure 2:
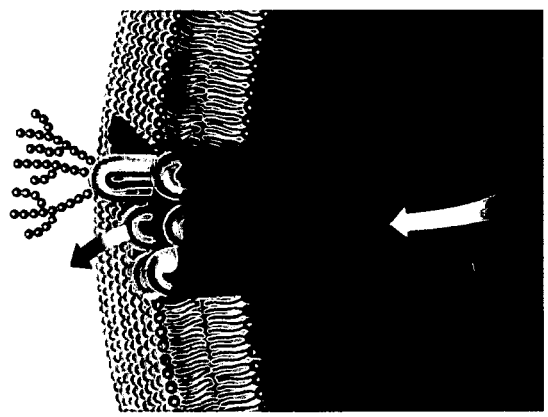
FIG. 2. is a schematic representation of the efflux pump, P-glycoprotein (P-gp or MDR1) at the cell surface. The efflux pump, P-gp or MDR1, associated with multidrug resistance is highly expressed at the cell surface of many cancer cells and various tissues including the blood-brain barrier.

Angiopep-1 and -2 represents two non-limitative, exemplary embodiments of aprotinin derived peptides which have been tested herein (FIG. 1). Taxol which represents a non-limitative exemplary embodiment of a molecule or compound conjugated to the carrier of the present invention was chosen as a candidate anticancer drug as this natural compound, isolated from the bark and needles of the yew tree, is a highly efficient chemotherapeutic. Moreover, this compound is approved by the Food and Drug Administration (FDA) for ovarian cancer, breast cancer, non-small cell lung cancer and Kaposi's sarcoma and is a well characterized anticancer agent.

EXAMPLES

Cell Proliferation Assay

For the in vitro cell proliferation assay, between 2.5 and 5×10$^4$ of U87 or A549 cells were seeded in a 24 well tissue culture microplate in a final volume of 1 ml of medium with 10% serum and incubated for 24 hours at 37° C. and 5% CO$_2$. The medium was then replaced with serum-free medium and incubated overnight. The next morning the drug was freshly dissolved in dimethyl sulfoxide (DMSO) and the medium was replaced with complete medium containing the drug at different concentrations in triplicates. The final concentration of DMSO was 0.1%. The control used is a microplate well with cells and without drug. The cells were incubated for 48 to 72 hrs at 37° C. and 5% CO$_2$. After the incubation, the medium was changed and replaced with 1 ml of complete medium containing [$^3$H]-thymidine (1 μCi/assay). The plate was incubated at 37° C. and 5% CO$_2$ for 4 hrs. The medium was removed and the cells washed with PBS heated at 37° C. The cells were fixed with a mix of ethanol:acetic acid (3:1), then washed with water and precipitated 3 times with 10% of ice-cold TCA (trichloroacetic acid). Finally 500 µl of PCA (perchloric acid) were added to the wells and the microplates were heated for 30 min at 65° C. and 30 min at 75° C. The contents of each well was then transferred in a scintillation vial with 10 ml of scintillation cocktail and the activity was measured in CPM (count per minute) on a liquid scintillation counter Tri-Carb from Packard.

Iodination of Peptides

Peptides were iodinated with standard procedures using iodo-beads from Sigma. Both Angiopep-1 and Angiopep-2 were diluted in 0.1M phosphate buffer, pH 6.5 (PB). Two iodo-beads were used for each protein. These beads were washed twice with 3 ml of PB on a whatman filter and re-suspended in 60 µl of PB. $^{125}$I (1 mCi) from Amersham-Pharmacia biotech was added to the bead suspension for 5 min at room temperature. Each iodination was initiated by the addition of the peptide (100 µg). After an incubation of 10 min at room temperature, the free iodine was removed by HPLC.

Subcutaneous Implantation

In order to estimate the efficiency of the Taxol-conjugates and formulations on tumor growth, we developed a subcutaneous model of glioblastomas. In this model, 2.5×10$^6$ cells in 100 µl of cell medium without serum containing 1% methylcellulose were subcutaneously injected in the mice flank. The tumor was clearly visible and could be measured using a vernier caliper. The estimated tumor volume was then plotted as a function of time.

In Situ Mouse Brain Perfusion

The uptake of [$^{125}$I]-peptides to the luminal side of mouse brain capillaries was measured using the in situ brain perfusion method adapted in our laboratory for the study of drug uptake in the mouse brain. Briefly, the right common carotid of ketamine/xylazine (140/8 mg/kg i.p.) anesthetized mice was exposed and ligated at the level of the bifurcation of the common carotid, rostral to the occipital artery. The common carotid was then catheterized rostrally with polyethylene tubing filled with heparin (25 U/ml) and mounted on a 26-gauge needle. The syringe containing the perfusion fluid ([$^{125}$I]-peptides or [$^{14}$C]-inulin in Krebs/bicarbonate buffer at a pH7.4 gassed with 95% O$_2$ and 5% CO$_2$) was placed in an infusion pump (Harvard pump PHD 2000; Harvard Apparatus) and connected to the catheter. Prior to the perfusion, the contralateral blood flow contribution was eliminated by severing heart ventricles. The brain was perfused for the indicated times at a flow rate of 1.15 ml/min. After 14.5 min of perfusion, the brain was further perfused for 60 s with Krebs buffer, to wash the excess of [$^{125}$I]-proteins. Mice were then decapitated to terminate perfusion and the right hemisphere was isolated on ice before being subjected to capillary depletion. Aliquots of homogenates, supernatants, pellets and perfusates were taken to measure their contents in [$^{125}$I]-conjugates by TCA precipitation and to evaluate the apparent volume of distribution.

Example 1—Preparation of Conjugates

Since the resistance towards various drugs such as vincristine, etoposide, and doxorubicin is mediated through P-gp (MDR1) overexpression (FIG. 2), any methods of bypassing this efflux pump may potentiate the action of these drugs on various cancer types. The bypass of P-gp may therefore be useful to increase the potency of drugs which are associated with resistance mediated by P-gp. Carriers described herein were therefore tested for their ability to bypass P-gp.

Figure 3A:
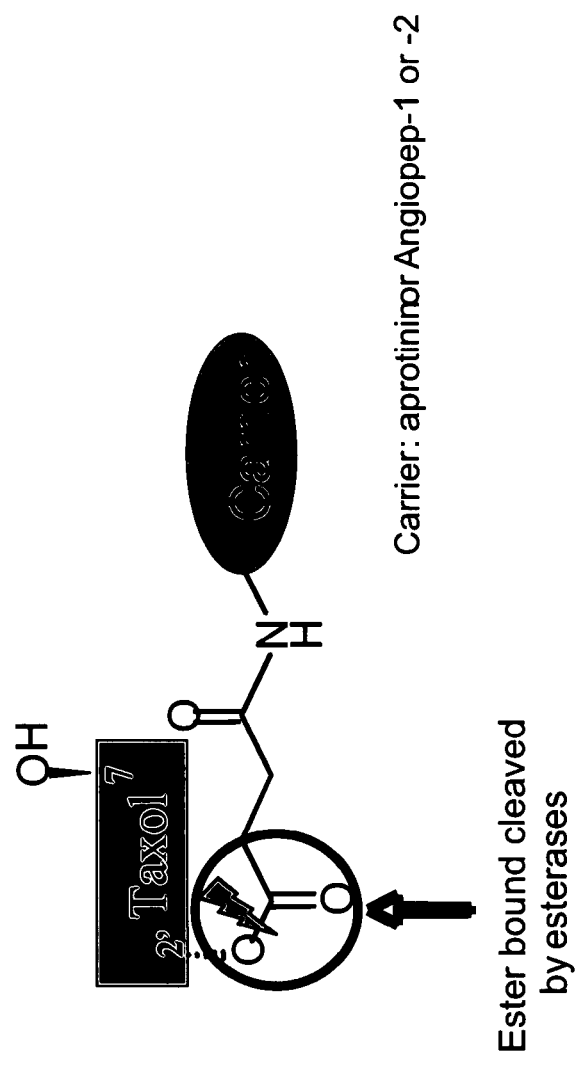
FIG. 3A. is a schematic representation of conjugation of a drug to the carrier peptide of the present invention.
Figure 3B:
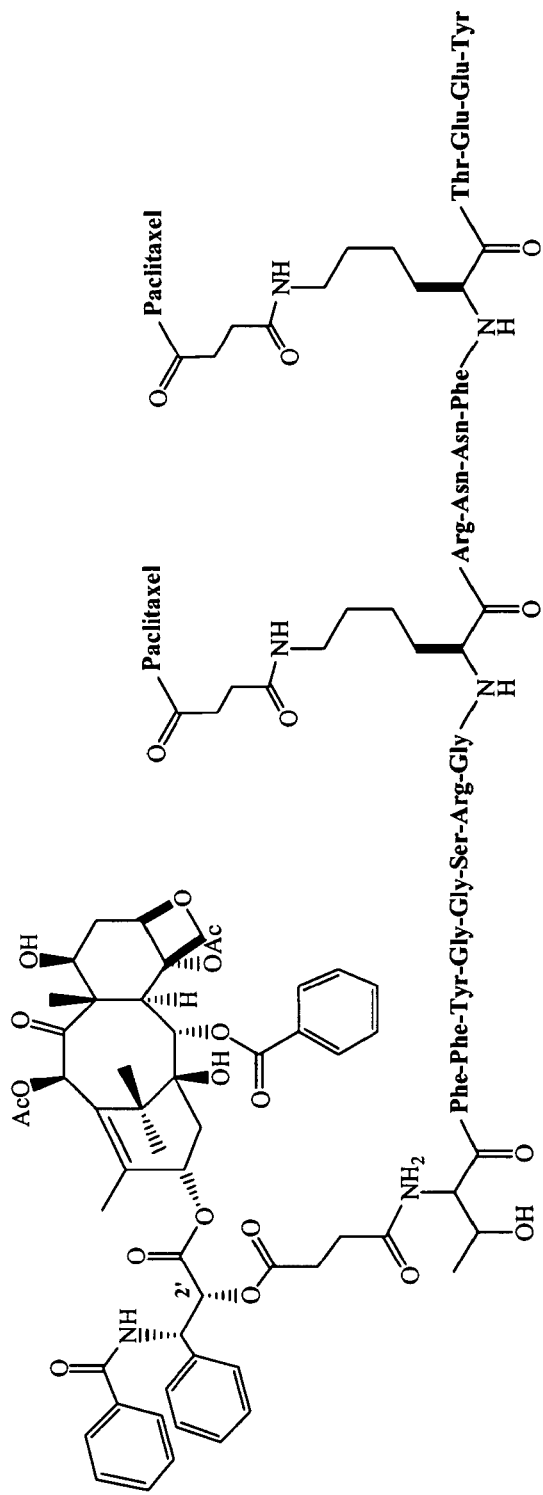
FIG. 3B is a representation of the chemical structure of TxlAn2 (3:1)

The conjugation of a drug to the carrier described herein is illustrated in FIG. 3. Briefly, in order to conjugate Taxol to the Angiopep-1 or Angiopep-2 carrier, Taxol was first activated into N-succinimide (2'-NHS-Txl) derivative. Then amines found for example in lysine residue or amino-terminal of Angiopep-1 or Angiopep-2 reacted on this activated-Taxol by forming a peptide bond (amide bond). In Angiopep-1 or Angiopep-2, the amino-terminal (in position 1) and the lysines (at position 10 and 15) were able to react with activated-Taxol. Therefore, multiple combinations of conjugates was found to occur by the addition of 1, 2 or 3 Taxols to the peptide depending on the molar ratio used (FIG. 3). The whole conjugation was analyzed by HPLC and conjugation was confirmed by Mass spectra (Maldi-Tof). Taxol was found to be releasable from the carrier by the cleavage of the ester bond by esterases. Conjugates were therefore efficiently produced by combining the carrier with an anticancer drug.

Figure 4:
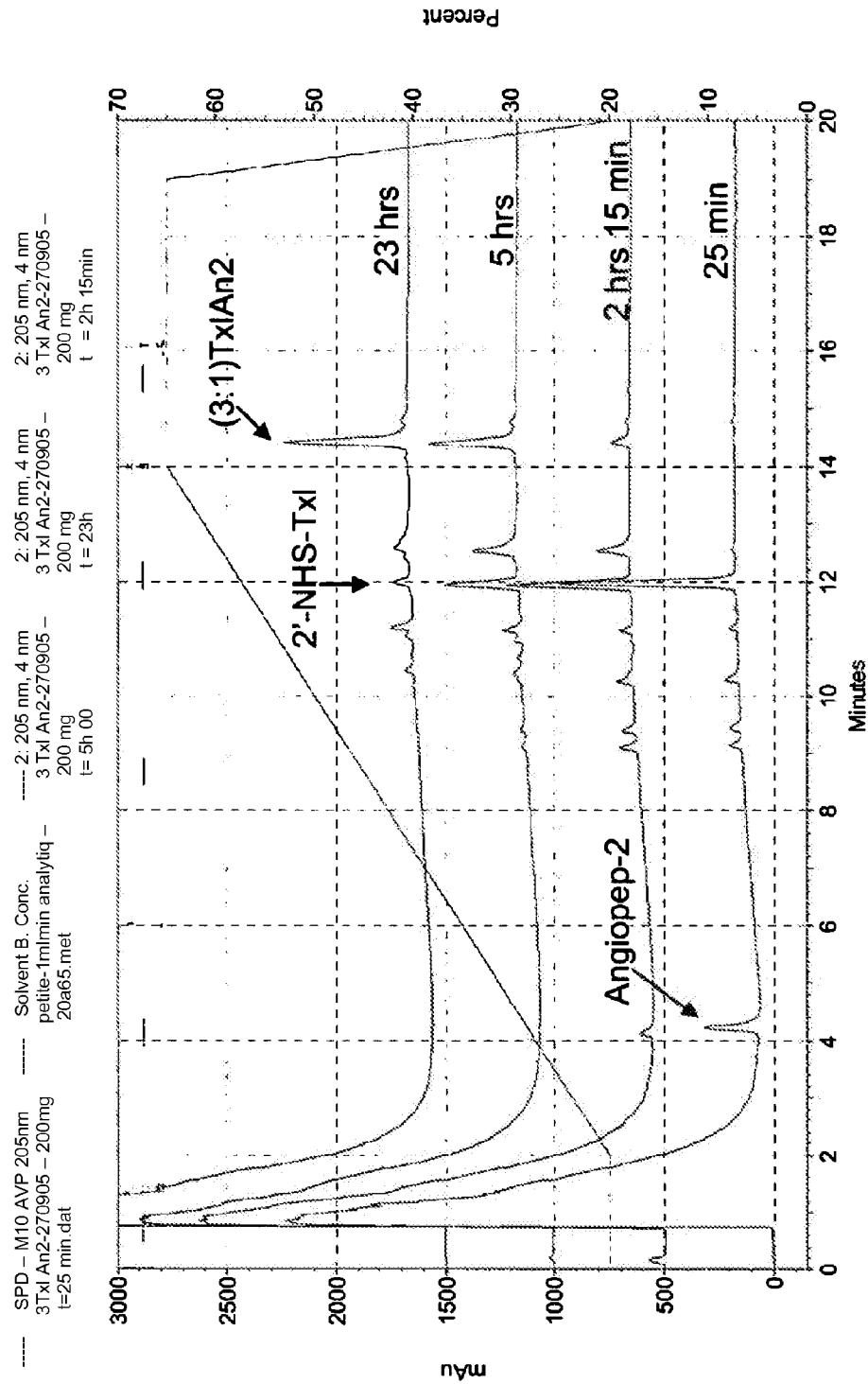
FIG. 4. is a chromatogram illustrating the production in high amount of TxlAn2 (3:1) conjugate.

In an exemplary embodiment of the present invention, the production of the TxlAn2 (3:1) conjugate, was carried out by directly adding 1 mole equivalent of Angiopep-2 to a solution of 2.5 moles equivalent of 2'-NHS-Taxol. The reaction was performed in 68% DMSO in Ringer solution (pH 7.3), for 1 hr at 12° C. and after removing the cold bath, for about 22 hrs at room temperature (FIG. 4). Angiopep-2, 2'-NHS-Taxol and TxlAn2 (3:1) conjugate are shown on the chromatogram by arrows. Aliquots of the reaction were sampled and analyzed by HPLC after 25 min, 2 hrs 15 min, 5 hrs and 23 hrs as indicated in FIG. 4. The peaks of Angiopep-2, 2'-NHS-Taxol and TxlAn2 (3:1) conjugate are shown by arrow on the chromatogram. Results of FIG. 4 illustrate the disappearance of Angiopep-2 and 2'-NHS-Taxol during the reaction mainly to the profit of the TxlAn2 (3:1) conjugate.

Figure 5:
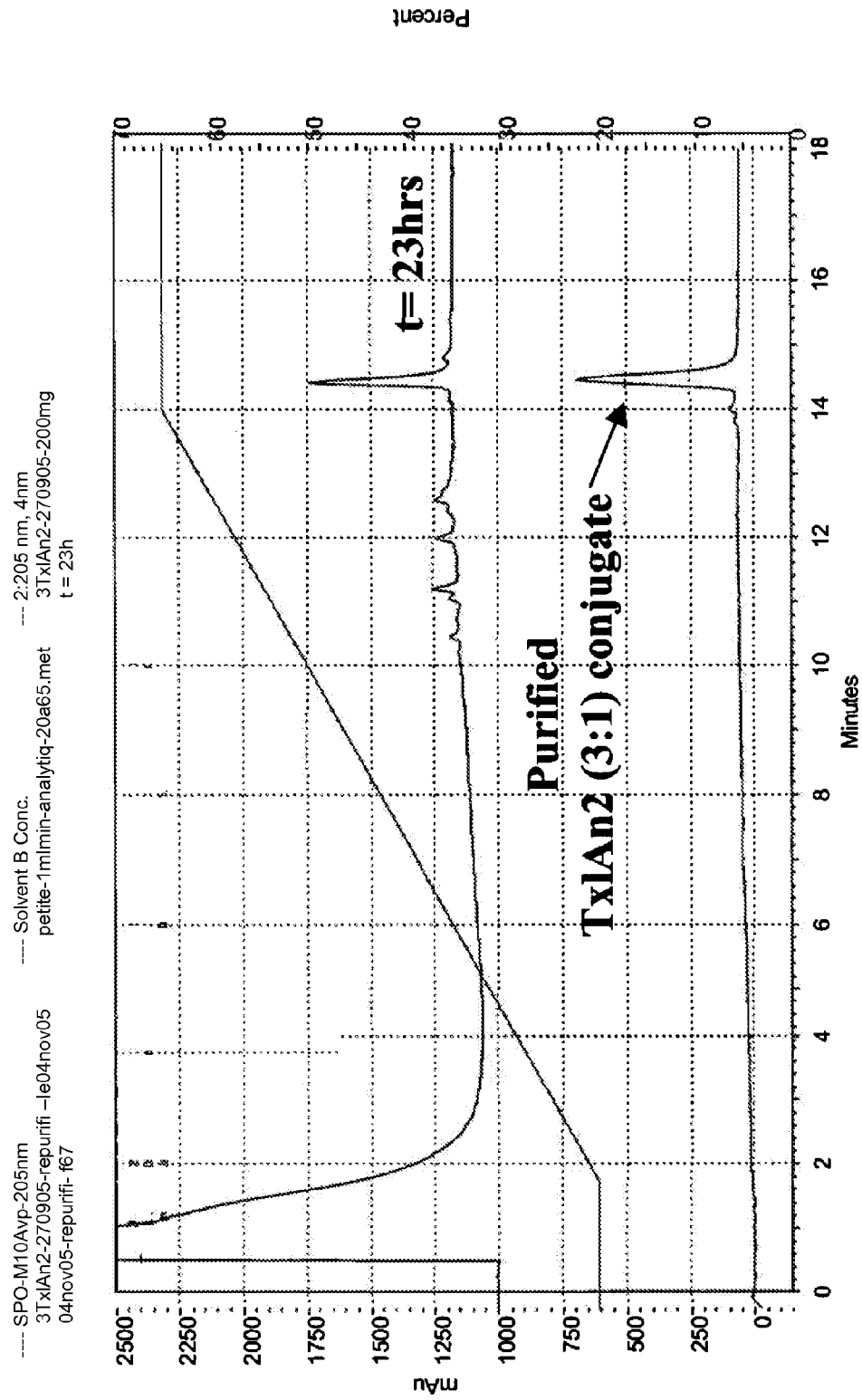
FIG. 5. is a HPLC analysis of the peak purified on a hydrophobic column using AKTA-explorer.

This mixture of products was separated by hydrophobic chromatography on a RPC 300 mm column with a flow rate at 4 ml/min using AKTA-explorer (FIG. 5). For the peak that corresponds to the TxlAn2 (3:1) conjugate, fractions were pooled, analyzed by HPLC and MS. In FIG. 5, the upper chromatogram corresponds to the running reaction at t=23 hrs whereas the lower one corresponds to the TxlAn2 (3:1) conjugate which has been confirmed by mass spectrometry (MW 5107) after AKTA purification.

Example 2—In Situ Brain Perfusion of Taxol-Angiopep-2 Conjugates

Figure 6:
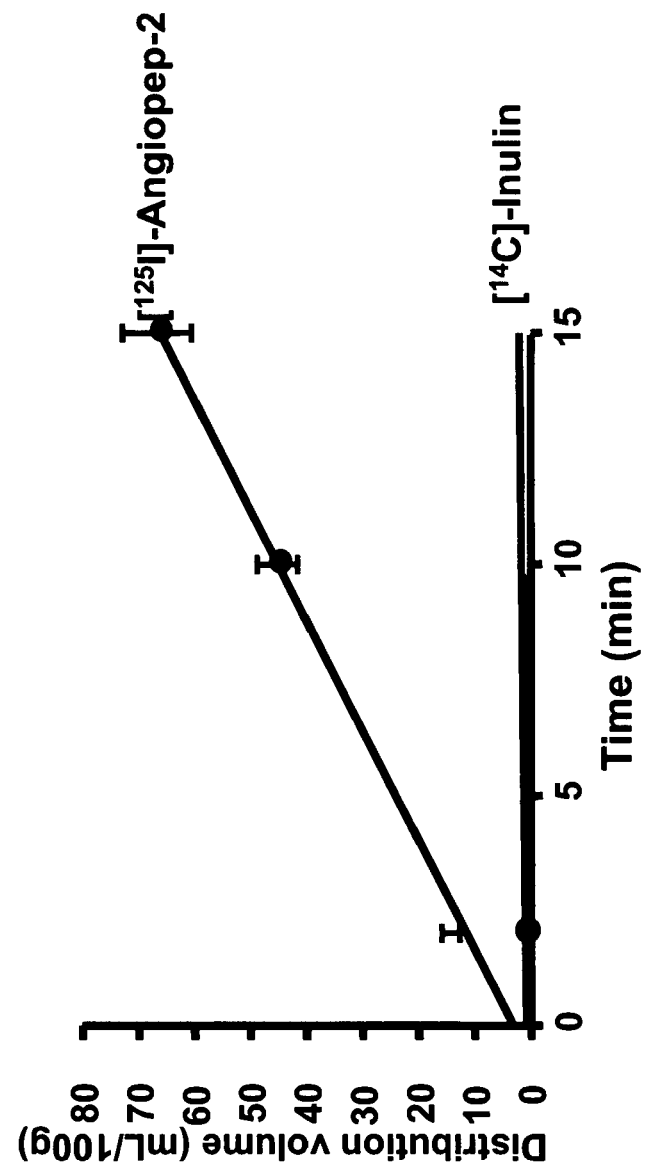
FIG. 6. is a diagram illustrating the In situ brain perfusion of radiolabeled Angiopep-2 and the vascular marker inulin.

To evaluate the brain uptake of Angiopep in vivo, the initial rate of transport for [$^{125}$I]-Angiopep into mouse brain parenchyma was measured using in situ brain perfusion as described herein. Mouse brain was perfused for the indicated times with either [$^{125}$I]-Angiopep-2 or [$^{14}$C]-inulin. After perfusion, the brain was further perfused for 60 sec with Ringer solution to wash the excess of radiolabeled molecules and then the right hemisphere was isolated on ice before being subjected to capillary depletion. Aliquots of homogenates, supernatants, pellets and perfusates were taken to measure their contents in [$^{125}$I]-Angiopep-2 or [$^{14}$C]-inulin. Results obtained for the accumulation for these molecules into the brain parenchyma are illustrated in FIG. 6. The accumulation of [$^{125}$I]-Angiopep-2 increased as a function of time and is higher than that of the vascular marker, [$^{14}$C]-inulin.

Figure 7:
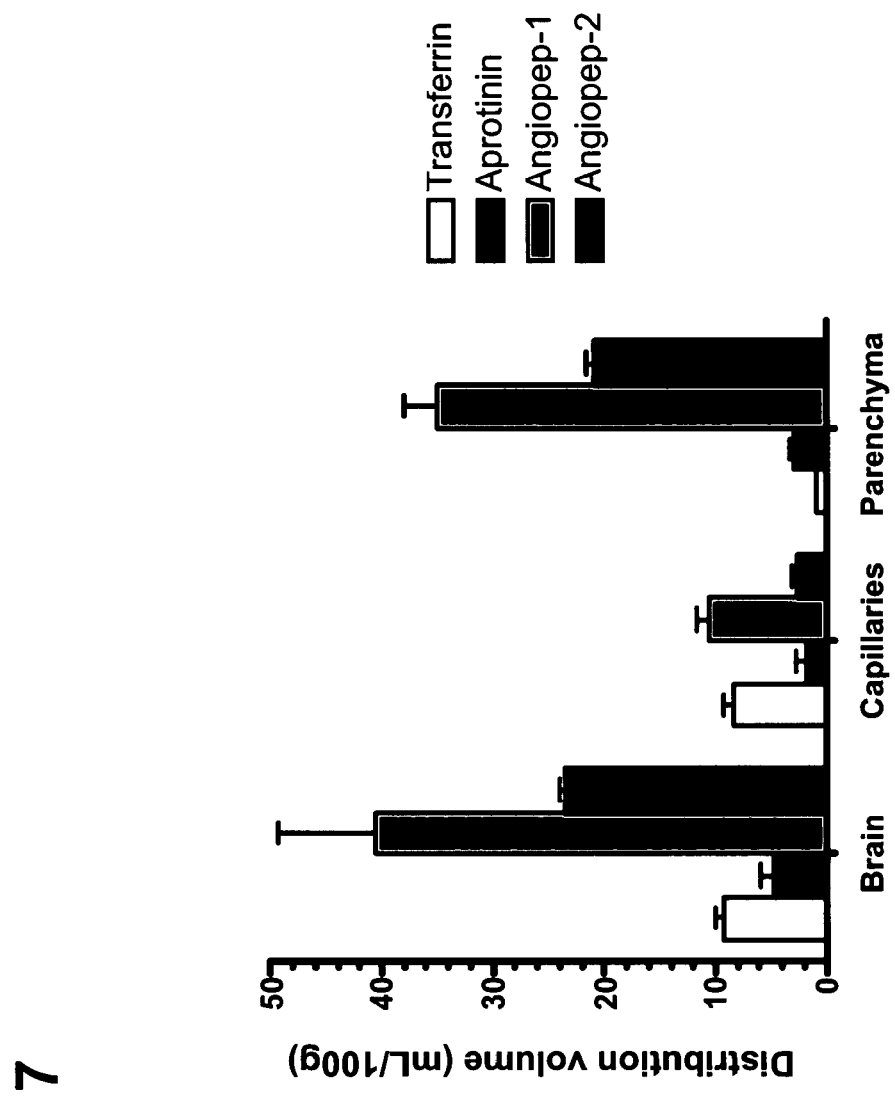
FIG. 7. is an histogram illustrating the apparent distribution volume of transferrin, aprotinin and Angiopeps in total brain, brain capillaries and brain parenchyma.

We further compared the initial brain uptake after a 5 min perfusion for [$^{125}$I]-aprotinin, [$^{125}$I]-transferrin and [$^{125}$I]-Angiopeps (FIG. 7) (1:1). Results show that Angiopep and aprotinin have a highest initial transport rate than transferrin.

Example 3—Effect of Conjugates on Cell Growth

Figure 8:
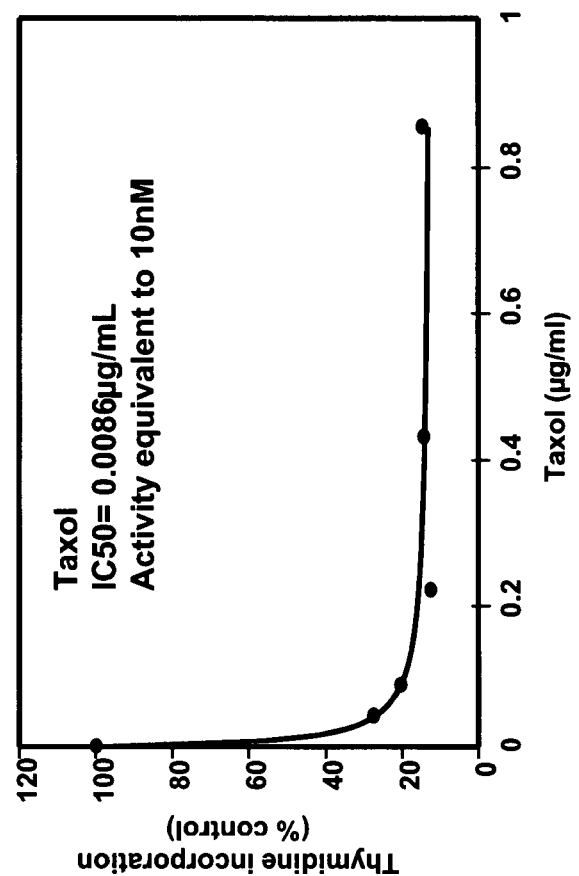
FIG. 8. is a diagram of cell proliferation in the presence of the parent drug Taxol. Glioblastoma cells (U-87) were exposed to various concentrations of Taxol for 3-days. $^3$H-Thymidine incorporated in cells were plotted as a function of Taxol concentrations.

In an in vitro assay, Taxol (unconjugated) was shown herein to block the proliferation of glioblastoma cells (U-87) with IC50 value of around 10 nM (FIG. 8). The effect of Taxol conjugated with the carrier described herein on the proliferation of various cell lines was then evaluated and compared to unconjugated Taxol (referred as Taxol). As shown in Table 3A, the IC50 values obtained for the Taxol-Angiopep-2 (TxlAn2) conjugate were very similar to that of unconjugated Taxol in many cancer cells. Endothelial cells from rat brain (RBE4) were less sensitive than the tested cancer cell lines. Overall, these results indicate that the potency of conjugates to block cell proliferation in vitro is similar to the unconjugated Taxol. For comparison purposes, results obtained were expressed in term of Taxol concentration.

TABLE 3A

Effect of conjugate on cell proliferation.

| | IC50 (nM) | |
|---|---|---|
| Cell lines | Taxol | Taxol-Angiopep-2 (3:1) |
| Glioblastomas | | |
| U-87 | 9.5 | 9.7 |
| U-118 | 7.2 | 8.1 |
| Lung carcinoma | | |
| NCI-H460 | 9.3 | 12.5 |
| A549 | 3.6 | 6.0 |
| Calu-3 | 17.2 | 25.0 |
| Endothelial cells | | |
| RBE4 | 137 | 139 |

Most of theses cells (U-87, U-118, NCI-H460, A549) express LRP. This data is however unavailable for RBE4 cells.

The anti-proliferatice activity of the conjugate against cancer cells in vitro was further assessed. In this assay, cancer cells (U87 and U118) were exposed for 48 hrs to Taxol® and TxlAn2 (3:1) conjugate. Incorporation of [$^3$H]-thymidine in U87 and U118 cells decreased as a function of drug concentrations. The values required to inhibit cell proliferation by 50% (IC50) were expressed. Results obtained from the proliferation assays indicate that the IC50 values required for the inhibition of cancer cell proliferation are expressed in nM and demonstrate that TxlAn2 (3:1) conjugate is 3 times more potent than paclitaxel, and are in the same range when reported in paclitaxel equivalent (Table 3B).

The capacity of TxlAn2 (3:1) conjugate to block the proliferation of other cancer cell types was also estimated. Lung cancer cells (NCI-H460) as well as the breast cancer cell line (MDA-MB231, MDA-MB-468, HCC-1954, BT-474) in hepatocarcinomas (SK-Hep1) and glioblastomas (U-87MG) were also very sensitive to TxlAn2 (3:1) conjugate (Table 3B).

TABLE 3B

In vitro cytotoxicity of taxol and TxlAn2 (3:1) conjugate

| | Paclitaxel | | | | TxlAn2 (3:1) conjugate | | | |
|---|---|---|---|---|---|---|---|---|
| | IC50 (nM) | | Residual survival % | | IC50 (nM) | | Residual survival % | |
| Cell line | Mean | SD | Mean | SD | Mean | SD | Mean | SD |
| BT-474 | 62.86 | — | 52.24 | 3.87 | 40.22 | — | 51.83 | 1.70 |
| HCC1954 | 6.12 | — | 48.82 | 11.17 | 8.26 | 3.37 | 44.08 | 8.63 |
| MDA-MB-231 | 17.61 | — | 45.62 | 13.89 | 28.16 | — | 46.95 | 7.50 |
| MDA-MB-468 | 13.52 | — | 54.26 | 10.34 | 1.41 | — | 55.34 | 5.55 |
| NCI-H460 | 6.61 | 3.35 | 24.98 | 10.80 | 12.68 | 10.08 | 30.44 | 9.36 |
| SK-HEP-1 | 8.84 | — | 55.18 | 13.17 | 7.83 | — | 54.09 | 11.03 |
| U-87 MG | 12.94 | 2.49 | 40.35 | 2.40 | 17.75 | 10.82 | 44.13 | 1.85 |

Example 4—By-Passing of P-gp by Conjugates

Figure 9A:
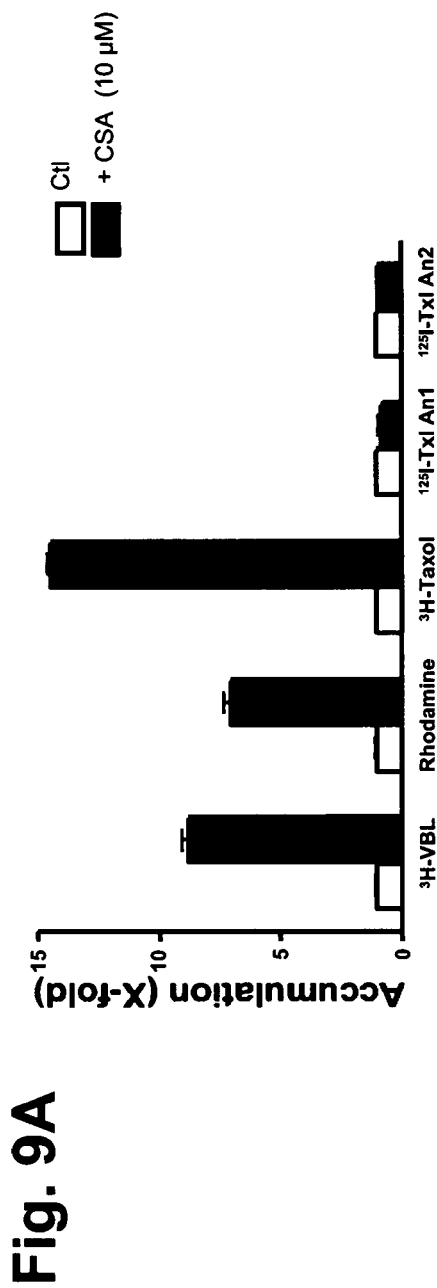
FIG. 9A is a diagram representing the accumulation of various drugs in MDCK cells transfected with MDR1 in the presence or absence (control) of 10 uM CsA, a P-gp inhibitor. The experiment was performed in the presence of 1% DMSO.

In order to determine whether the conjugates of the present invention were P-gp substrates or not, MDCK cells were stably transfected with human MDR1 (MDCK-MDR1) and were subsequently incubated with unconjugated-anticancer drug or with the conjugates of the present invention. In a first experiment, MDCK-MDR1 cells were incubated with $^3$H-vinblastine ($^3$H-VBL), rhodamine, $^3$H-Taxol, $^{125}$I-Taxol-Angiopep-1 ($^{125}$I-TxlAn1), $^{125}$I-Taxol-Angiopep-2 ($^{125}$I-TxlAn2) for 1 hr at 37° C. in the presence or absence of 10 μM of cyclosporine A (CsA); a P-gp competitive inhibitor (FIG. 9A). After the incubation, cells were washed and accumulation of radioactivity inside the cells or intracellular fluorescence was quantified. The increased in the accumulation of these drugs is expressed in term of x-fold compared to their respective control measured in the absence of CsA. Thus, the control value for each drug was set to 1-fold.

Figure 9B:
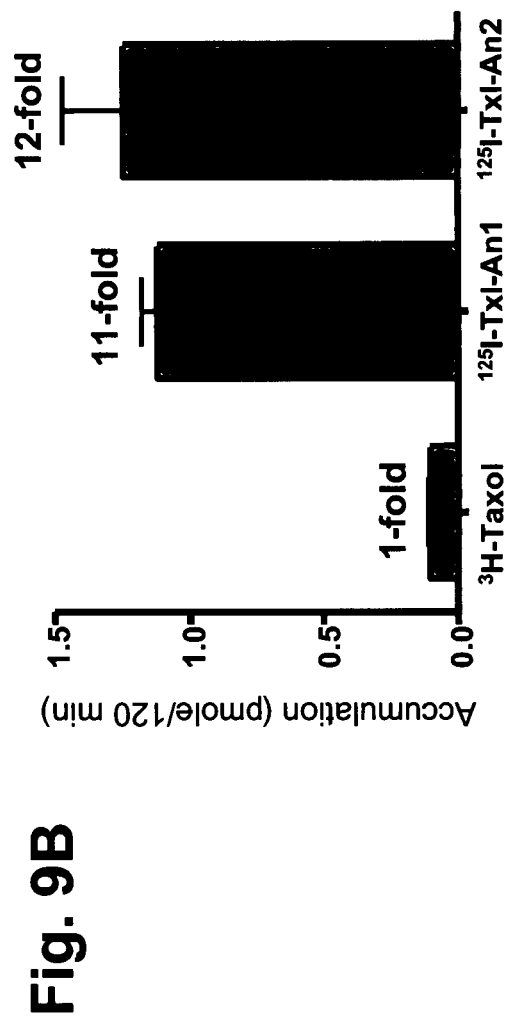
FIG. 9B. is a diagram representing the accumulation of the conjugate in cells over-expressing P-gp.

In another experiment, the ability of the conjugates to accumulate in cells overexpressing P-gp was monitored (FIG. 9B). MDCK-MDR1 cells were incubated with 50 nM of either $^3$H-Taxol, $^{125}$I-Taxol-Angiopep-1 ($^{125}$I-TxlAn1) or $^{125}$I-Taxol-Angiopep-2 ($^{125}$I-TxlAn2) for 2 hrs at 37° C. After the incubation, the cells were washed and the radioactivity accumulated in cells was quantified. The results were expressed as drug accumulation in pmole/120 min.

As shown in FIG. 9A, the accumulation of [$^3$H]-Taxol increased by 15-fold in the presence of the P-gp competitive inhibitor; cyclosporin A (CsA). The accumulation of rhodamine and [$^3$H]-vinblastine also increased by 7.5-fold and 10-fold respectively in the presence of CsA. These results show that Taxol, rhodamine and vinblastine are P-gp substrates. However, the lack of CsA effect on the accumulation of both [$^{125}$I]-Taxol-Angiopep-1 and [$^{125}$I]-Taxol-Angiopep-2 conjugates, indicates that they are not P-gp substrates. The accumulation of both conjugates, in the absence of CsA, was at least 11-fold higher than of [$^3$H]-Taxol (FIG. 9B). These later results strongly confirm that both conjugates bypass the action of P-gp since P-gp is not able to expulse them from the cells. These results additionally demonstrate that the presence of a carrier in conjugation with an anticancer drug increases the potency of the drug. Therefore, the carriers described herein are useful for the transport and/or accumulation of drugs inside a cell and are especially useful for drugs which are usually expulsed by P-gp (i.e., drugs which are P-gp substrates).

Example 5—Distribution and Pharmacokinetics of Conjugates

Figure 10B:
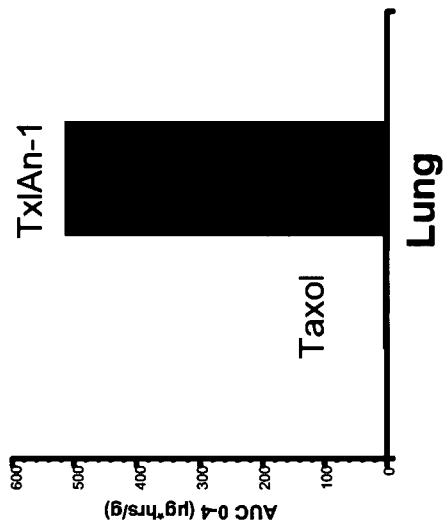
FIGS. 10A and 10B are diagrams representing tissue distribution of Taxol and TxlAn1 conjugate.
Figure 10A:
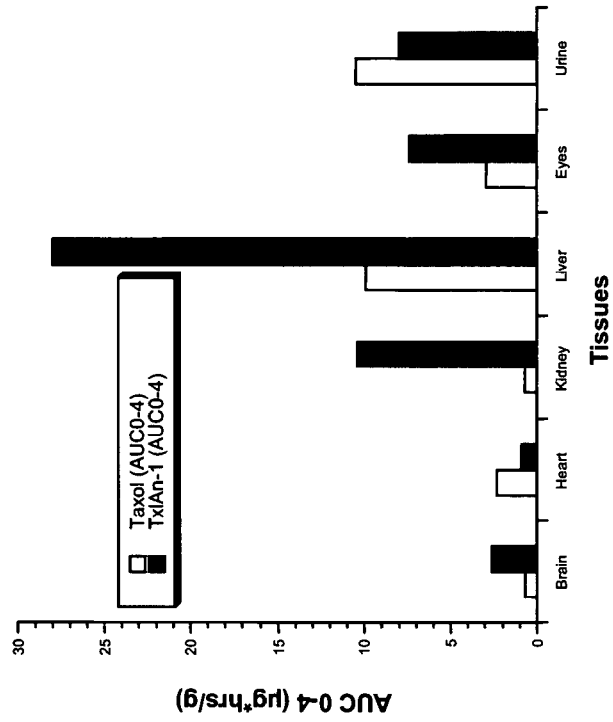

The impact of conjugation of the drug to the carrier on drug distribution was evaluated by administering either $^3$H-Taxol (5 mg/kg) or $^{125}$I-Taxol-Angiopep-1 (TxlAn-1) (10 mg/kg, equivalent to 5 mg of Taxol/kg) to mice. The unconjugated anticancer drug and the conjugates were injected intra-venously (i.v.) in mice as a bolus. Tissues were collected at different times (0.25, 0.5, 1 and 4 hrs) and homogenized. In order to quantify the amount of $^3$H-Taxol, tissue homogenates were digested with tissue solubilizer (soluble) and 10 ml of liquid scintillator was then added to samples. The amount of the $^{125}$I-labeled conjugate, in the different tissues was measured after TCA precipitation. Radioactivity associated with the tissues was therefore quantified. The area under the curve (AUCO-4) was estimated using the Prism software and was plotted for the different tissues (FIG. 10). Results of FIG. 10A indicate that the AUCO-4 values obtained for the conjugate are higher than that of Taxol in various tissues including the brain, kidney, liver and the eyes which indicates a higher accumulation of the conjugate in these tissues compared to the unconjugated drug. More particularly, results presented in FIG. 10B indicate that the accumulation of the conjugate is much higher than unconjugated drug in the lung.

Results of a similar experimentation conducted with the Taxol-angiopep-2 conjugate are summarized in Table 4 below. Although there is difference with results obtained for the TxlAn-1 conjugate, the conjugate of Table 4 also accumulates in the lungs, brain and liver more efficiently than unconjugated Taxol.

TABLE 4

| Tissue | AUC 0-4 (μg/g of tissue) | | Ratio (TxlAn-2/Taxol) |
|---|---|---|---|
|  | TxlAn-2 | Taxol |  |
| Plasma | 170 | 2.2 | 77.3 |
| Brain | 0.32 | 0.07 | 4.6 |
| Lung | 3.4 | 1.1 | 3.0 |
| Kidney | 11.2 | 8.0 | 1.4 |
| Heart | 5.0 | 2.5 | 2.0 |
| Liver | 513 | 22 | 23 |
| Eye | 0.99 | 0.57 | 1.7 |
| Urine | 35.7 | 88 | 0.4 |

Treatments equivalent to 5 mg/kg of Taxol

Figure 11:
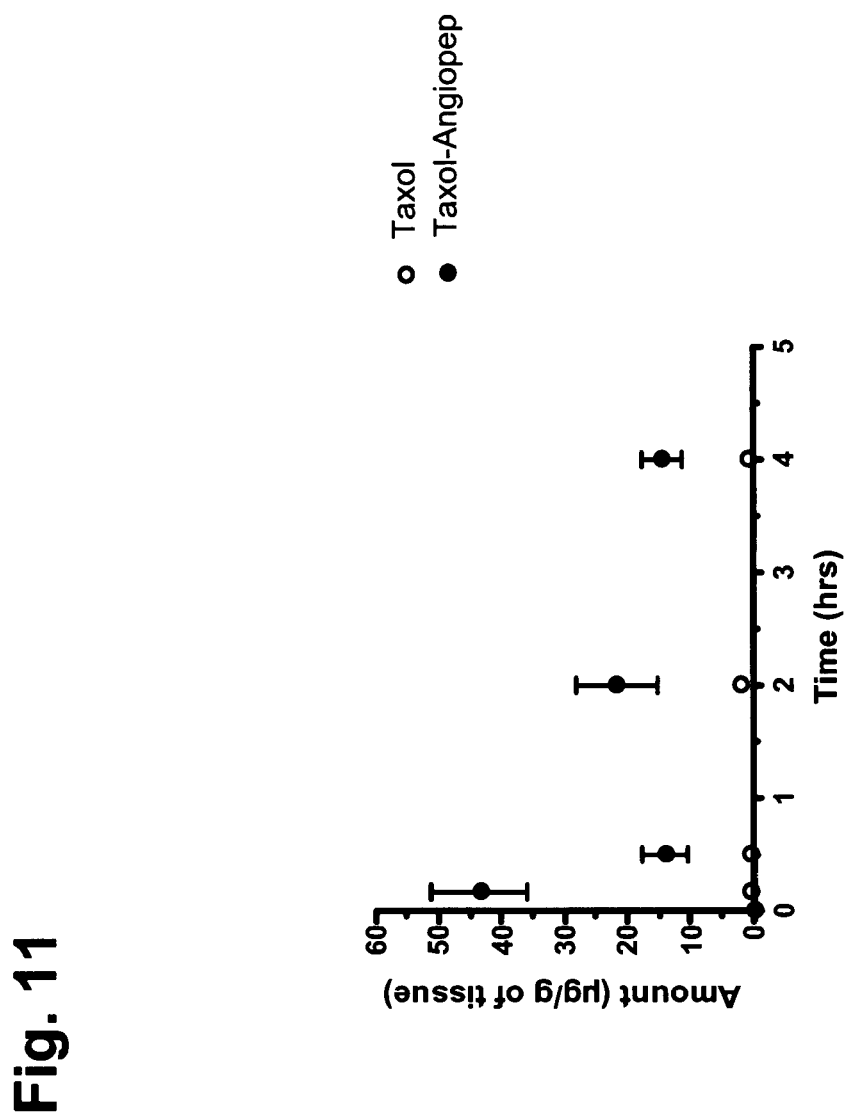
FIG. 11 is a diagram representing lung distribution of Taxol and TxlAn1.
Figure 12:
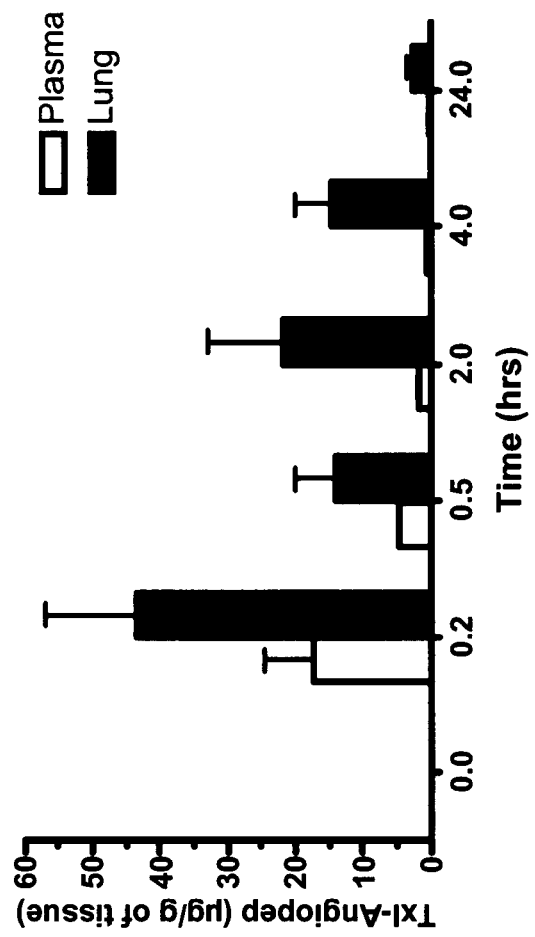
FIG. 12 is a diagram representing the levels of TxlAn1 conjugate in plasma and lung.

The kinetics of Taxol and Taxol-Angiopep-1 accumulation in the lung is also presented in FIG. 11. Results clearly show that the amount of the conjugate measured in the lungs at different times is much higher than for the unconjugated drug. Moreover, we also observed that the accumulation of the conjugate in the lung is also much higher than its concentration in the serum (plasma) at various times (FIG. 12). Results presented in FIGS. 10, 11 and 12, strongly indicate that the conjugation of an anticancer drug (e.g., Taxol) to the carrier of the present invention (e.g., Angiopep-1 or 2) modifies the biodistribution of the anticancer drug and its pharmacokinetics.

Example 6—Inhibition of Tumor Growth In Vivo (U-87)

Figure 13A:
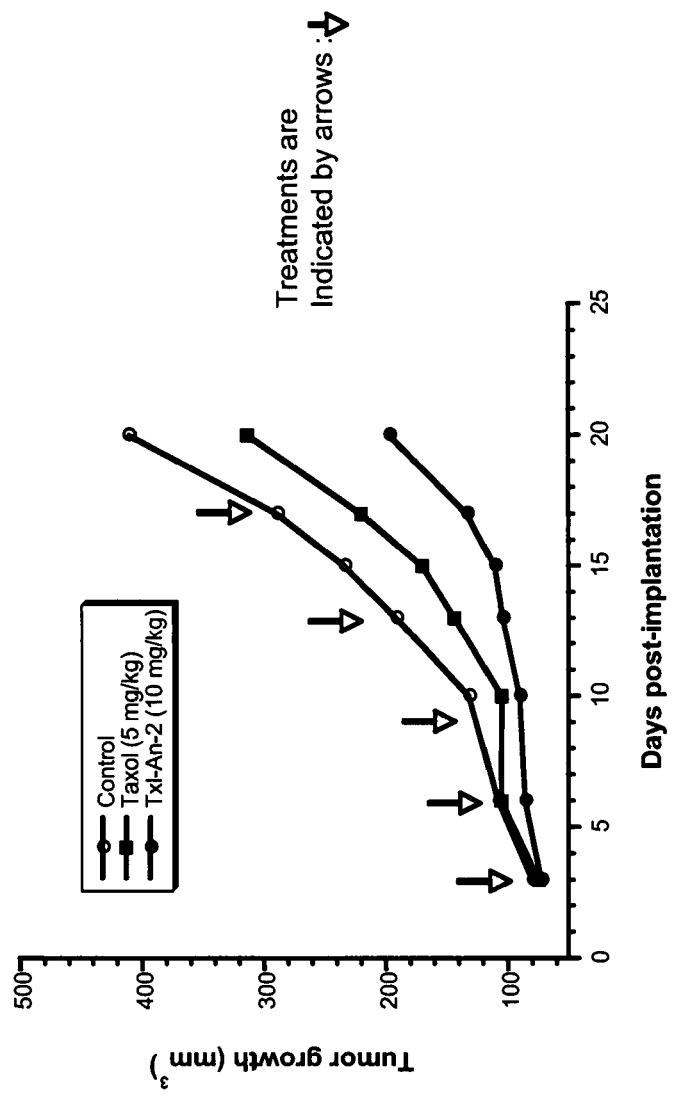
FIG. 13A is a diagram representing the effect of TxlAn2 treatment on subcutaneous glioblastomas (U-87) tumor growth.

The ability of conjugate to inhibit tumor growth was next evaluated in an in vivo model (FIG. 13A). U-87 cells were therefore subcutaneously implanted in the right flank of mice and on day 3 post-implantation, mice were injected with the vehicle (DMSO/Ringer: 80/20; control), Taxol (5 mg/kg) or Taxol-Angiopep-2 (10 mg/kg; equivalent to 5 mg of Taxol/kg (3 Taxol: 1 Angiopep-2)). We observed that the tumor growth inhibition was more pronounced in mice treated with the conjugate than in mice treated with the unconjugated anticancer drug.

In fact at day 17 post-implantation, tumor growth was inhibited by more than 75% by the conjugate whereas tumor growth was inhibited by only 34% using the unconjugated drug (Table 5). These results show that the conjugates described herein are more efficient than unconjugated Taxol at inhibiting tumor growth in vivo. Overall, a 2.2-fold tumor growth inhibition level was measured for the conjugate compared to the unconjugated drug.

TABLE 5

Inhibition of tumor growth with conjugates.

| Groups | Tumor volume (mm³) (mean ± sem) Days post-injection | | Tumor growth Δ (mm³) | Inhibition (%) | T/C (%) |
|---|---|---|---|---|---|
|  | Day 0* | Day 14** |  |  |  |
| Control | 79 ± 7 | 289 ± 50 | 203 ± 47 |  | 100 |
| Taxol (5 mg/kg) | 74 ± 5 | 219 ± 52 | 134 ± 55 | 34 | 66 |
| TxlAn2 (3:1) (10 mg/kg) | 88 ± 9 | 144 ± 27 | 56 ± 32 | 73 | 27 |

Treatment equivalent to 5 mg/kg of Taxol
*corresponds to 3 days post-implantation (first treatment)
**corresponds to 17 days post-implantation (after 4 treatments)

Example 7—Inhibition of Tumor Growth In Vivo (Hepatocarcinoma)

Figure 13B:
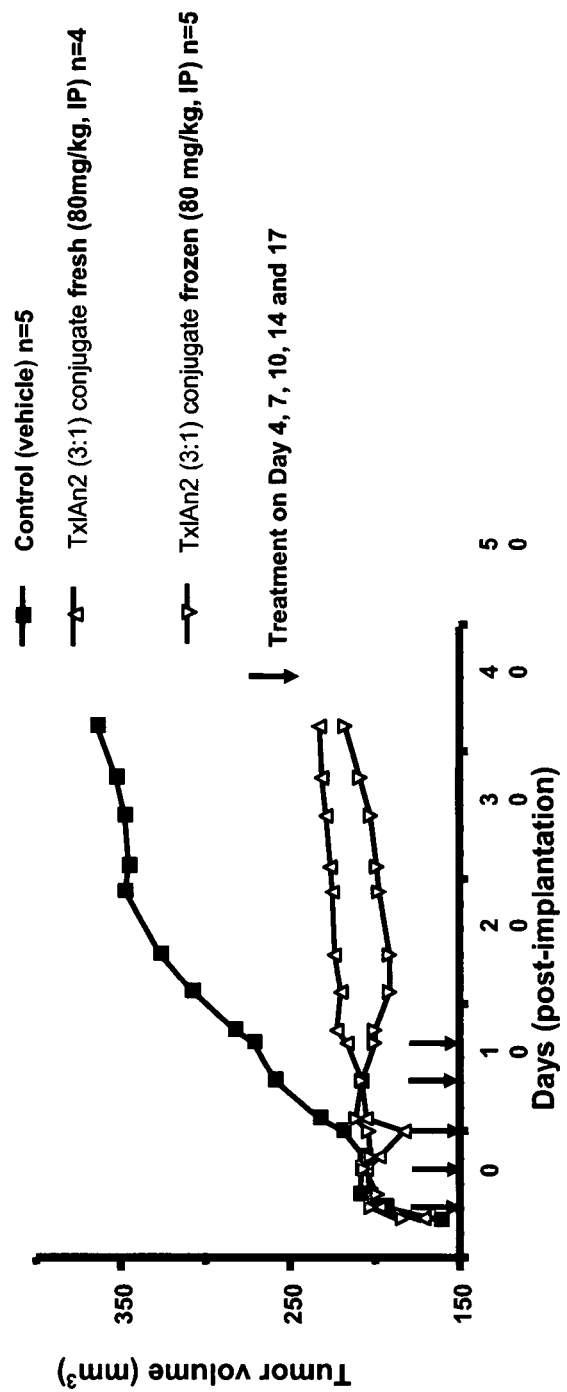
FIG. 13B is a diagram representing the effect of high dose of TxlAn2 (3:1) conjugate on SK-Hep 1 subcutaneous tumour growth.

In vivo studies were conducted to determine whether TxlAn2 (3:1) conjugate could inhibit the growth of Hepatocarcinoma cells (SK-Hep 1) that have been implanted subcutaneously. For these in vivo models, nude mice received a subcutaneous injection of 2.5×10⁶ human SK-Hep 1 cells in their right flank. Different treatments were started once the size of the implanted tumor reach approx. 200 mm³. Animals received treatment TxlAn2 (3:1) conjugate or vehicle by peritoneal injections (i.p.). TxlAn2 (3:1) conjugate was administered at 80 mg/kg by IP injection (TxlAn2 (3:1) conjugate was taken from 2 different batch stored in different conditions). In FIG. 13B treatments are indicated by black arrows.

Treatments were given twice a week for 5 treatments maximum at the dose indicated of 80 mg/kg. FIG. 13B shows that TxlAn2 (3:1) conjugate when administered i.p., shows high efficacy in inhibiting the growth of hepatocarcinomas. This type of cancer is usually not sensitive to Taxol®.

Example 8—Mechanism of Action of Conjugates

Figure 14:
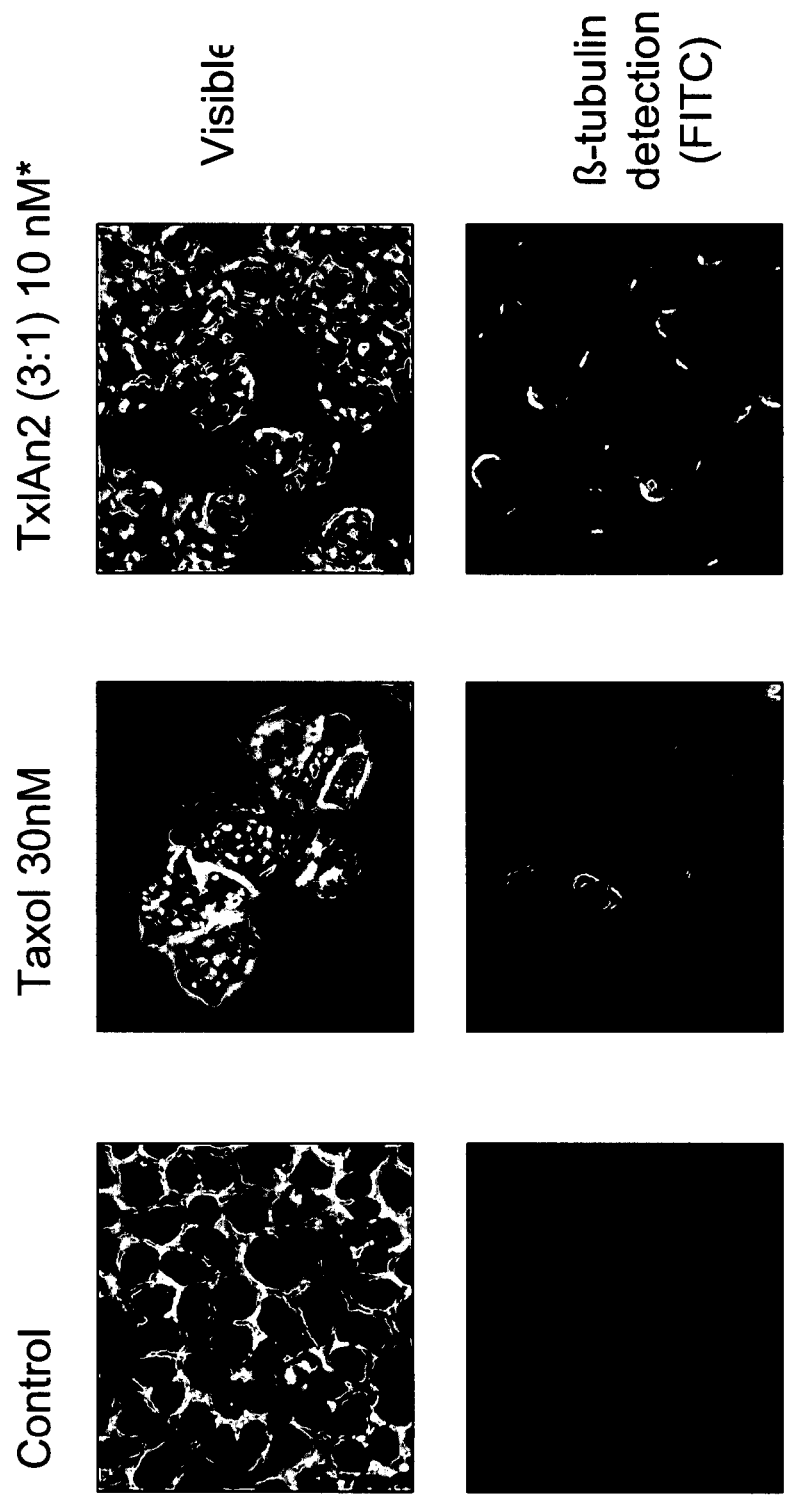
FIG. 14. are photographs illustrating the detection of β-tubulin in NCI-H460 by immunofluoresence or visible light in cancer cells exposed to Taxol or TxlAn2 conjugate, as control, cells were exposed to 1% DMSO.
Figure 15:
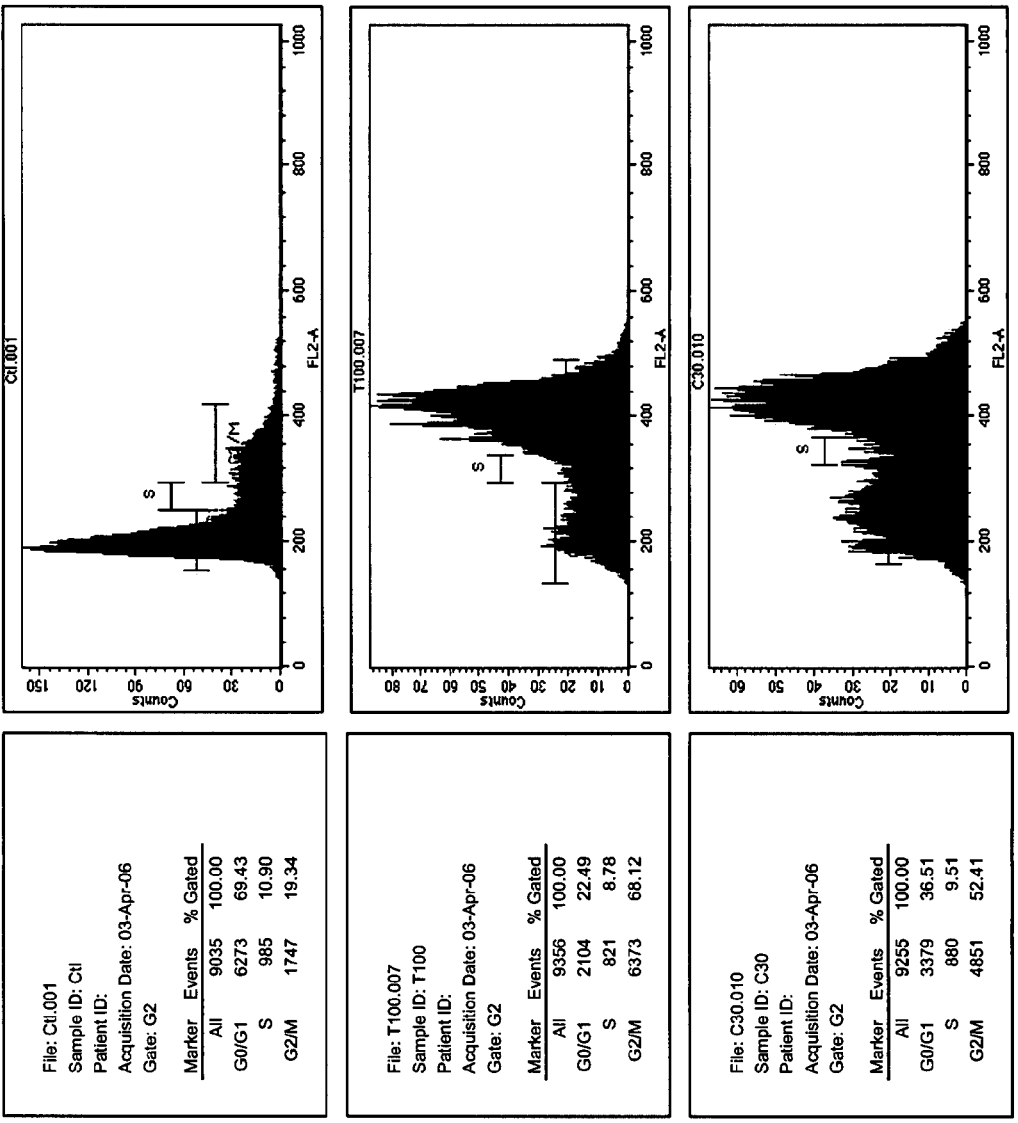
FIG. 15. are diagrams illustrating the effect of Taxol and TxlAn2 conjugate on NCI-H460 cell-cycle measured by FACS. Cells were exposed for 24 hrs with the vehicle (DMSO), Taxol (100 nM) or TxlAn2 conjugate (30 nM, equivalent to 100 nM of Taxol)

In FIG. 14, lung cancer cells (NCI-H460) were incubated for 24 hrs with either free Taxol (30 nM) or TxlAn2 conjugate (10 nM; equivalent to 30 nM of Taxol). After cells were labeled for β-tubulin by using a secondary antibody linked to FITC. Pictures were taken in visible and fluorescence modes. These results indicate that both Taxol and Taxol-Angiopep conjugate have similar effect on β-tubulin leading to its polymerization. Moreover, as indicated in FIG. 15, the addition of Taxol and Taxol-Angiopep conjugate induce a blockade of NCI-H460 cell in G2/M phase. Results obtained for the β-tubulin polymerization and cell cycle suggest that TxlAn conjugate has a similar mechanism of action on cancer cells than Taxol.

Example 9—Effect on LRP-Mediated RAP Accumulation

It was previously shown in international patent application No. PCT/CA2004/00011, that the receptor-associated protein (RAP) inhibited transcytosis of aprotinin in an in vitro model of the blood brain barrier. According to these data we proposed that the low-density lipoprotein related receptor (LRP) is involved in the penetration of aprotinin into the brain. Similar inhibition of Angiopep transport across an in vitro model of the blood-brain barrier was also obtained (data not show) suggesting that transcytosis of Angiopep across brain endothelial cell also involved LRP. LRP is a heterodimeric membrane receptor of 600 kDa composed of two subunits; the subunit-α (515 kDa) and the subunit β (85 kDa). Immunodetection of LRP was then performed to assess whether this receptor is expressed in human primary brain tumors such as glioblastomas and in human brain metastasis from breast, lung and melanoma cancers (FIG. 16). Briefly, equal amount of protein homogenates from human primary brain tumors (glioblastomas) or human brain metastasis were separated by gel electrophoresis. After electrophoresis, proteins were transferred to PVDF membrane and LRP was immunodetected by using a monoclonal antibody directed against the subunit-α obtained from Cedarlane Laboratories (Hornby, ON, Canada). LRP was visualized by a secondary antibody directed against mouse IgG linked to horseradish peroxidase and chemiluminescence reagents.

Under the experimental conditions used, the subunit a of LRP was immunodetected at 515 kDa in glioblastoma U-87 cells. LRP was also detected in all human primary brain tumors and human brain metastases (FIG. 16). In contrast, megalin (LRP2) was detected in only one brain metastasis of the lung (not shown). The expression of LRP in the different patient biopsies may explain in part why we previously observed a higher accumulation of Taxol-Aprotinin conjugate in brain tumors. Overall, since LRP may be involved in the transport of the carrier described herein, these results indicate that the conjugates may also target cells and tumors which express this receptor.

Figure 17A:
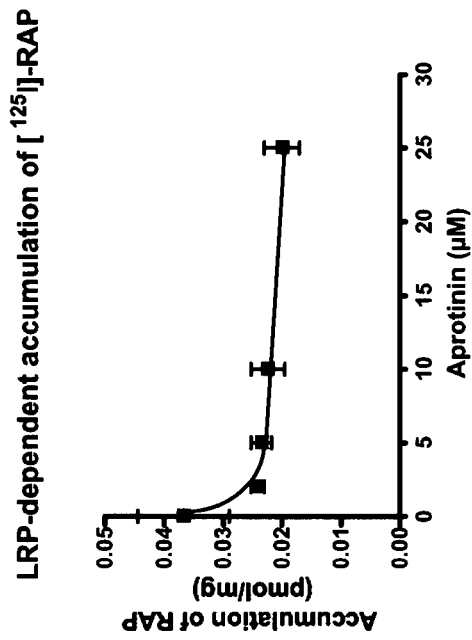
FIG. 17A. is a diagram illustrating the accumulation of [$^{125}$I]-RAP in fibroblasts MEF-1 and PEA-13 in the presence of various aprotinin concentrations.
Figure 17B:
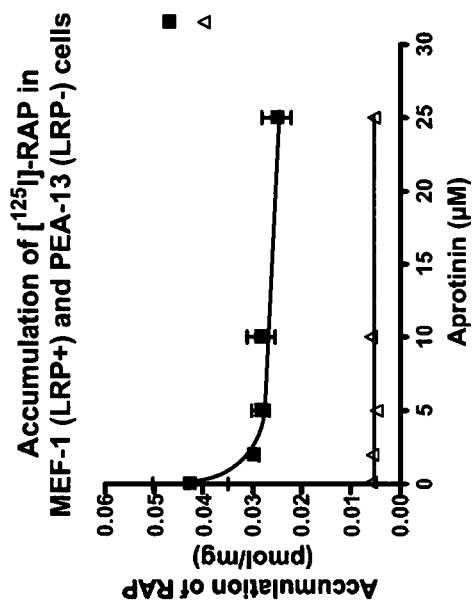
FIG. 17B. is a diagram expressing the results of FIG. 17A, where the LRP-dependent accumulation of [$^{125}$I]-RAP was calculated by subtracting the results for the uptake obtained with PEA-13 cells from the results with MEF-1 and expressed as a function of aprotinin concentrations.
Figure 18:
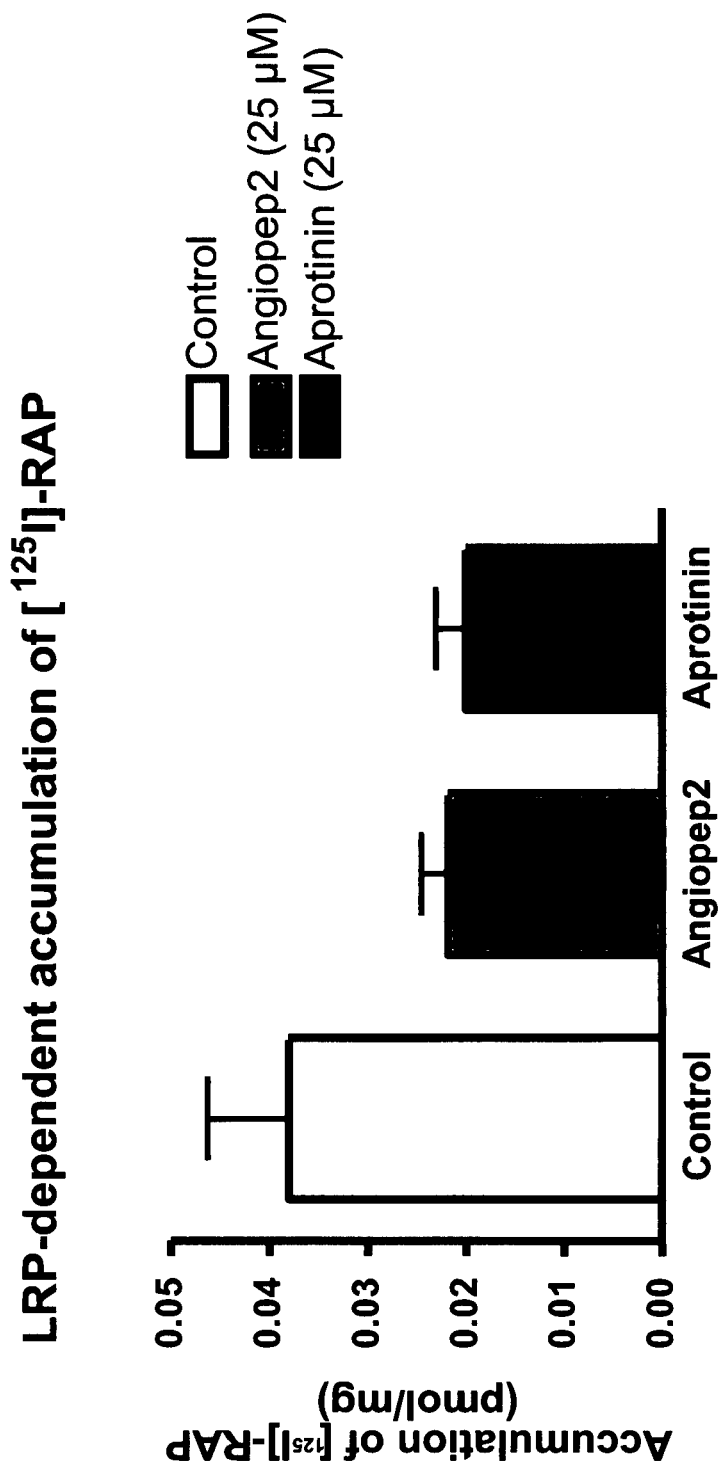
FIG. 18. is an histogram illustrating the effect of aprotinin and Angiopep-2 on RAP uptake. The accumulation of [$^{125}$I]-RAP in fibroblasts MEF-1 and PEA-13 was measured in the presence of 25 μM aprotinin or Angiopep. The LRP-dependent accumulation of [$^{125}$I]-RAP was calculated by subtracted the results for the uptake obtained with PEA-13 cells from the results obtained with MEF-1.

In order to determine whether aprotinin and Angiopep transcytosis could involve LRP, their impact on the uptake of the receptor-associated protein (RAP), an endogenous ligand for LRP, was determined (FIG. 17A). The uptake of RAP was measured in fibroblasts expressing LRP (MEF-1) and in fibroblasts that do not express LRP (PEA-13) (FIGS. 17A and 17B). The addition of aprotinin inhibited the transport of [$^{125}$I]-RAP in positive LRP cells in a dose-dependent manner. In contrast, the RAP uptake in negative LRP cells was almost unaffected by these aprotinin concentrations. In FIG. 17B the difference between the uptake of [$^{125}$I]-RAP measured in MEF-1 and PEA-13 was calculated and plotted as a function of aprotinin concentration. These results show that a portion of the LRP-dependent uptake of RAP could be reduced by aprotinin indicating that aprotinin could interact with this receptor. In a different experiment (FIG. 18), the uptake of [$^{125}$I]-RAP was also measured in the presence of an excess of aprotinin and Angiopep. Results show that both aprotinin and Angiopep affect the LRP-dependent accumulation of [$^{125}$I]-RAP.

In summary, data obtained for the conjugates described herein indicate that the conjugation of anticancer drugs to the carrier allows the anticancer drug to escape from P-gp action and therefore increase their potency (when conjugated with the carrier). These conjugates are active in vitro at inhibiting cancer cell proliferation. Moreover, results obtained on in vivo tumor growth indicate that the conjugation of anticancer drug to the carrier may increase their efficiency by bypassing P-gp, possibly targeting the receptor LRP or by modifying the pharmokinetics or biodisponibility of the unconjugated drug.

Taken together, data described herein indicates that the conjugates may be used against primary tumors including breast, lung and skin cancers as wells as metastasis originating from primary tumors.

Example 10—Improved Formulation of Taxol-Angiopep Conjugates

Preliminary assays performed to assess the solubility of the different TxlAn conjugates indicated that all conjugates had a low solubility in aqueous solution (e.g., in Ringer/Hepes solution) due to the highly hydrophobic nature of Taxol. However, all of the conjugates were very soluble in dimethyl sulfoxide (DMSO)/Ringer (80%/20%). Different strategies were thus assessed to increase their solubility and to reduce the amount of DMSO necessary for their solubilization. Interestingly, we were able to completely remove DMSO from the formulation by using the solubilizer agent macrogol 15 hydroxystearate (Solutol® HS15 (BASF)). For example, TxlAn2 (3.1) at 5 mg/ml was efficiently solubilized in 20% macrogol 15 hydroxystearate (Solutol® HS15) and Ringer/Hepes solution pH 5.5. As this agent has been approved for several drugs applications for intravenous (i.v.) and intraperitoneal (i.p.) administration, its use provides a commercial advantage to the formulations of the present invention.

Formulations of the present invention may thus comprise, for example, a) Taxol-Angiopep conjugates, b) macrogol 15 hydroxystearate (Solutol® HS15) and c) an aqueous solution or buffer (e.g., Ringer/Hepes solution at a pH of 5 to 7). The concentration of macrogol 15 hydroxystearate (Solutol® HS15) in the formulation may reach, for example, 30%. Concentration higher than 30% may also be useful. The concentration of conjugate may be determined based upon the dose required for efficiently treating a patient.

Example 11—Blood Kinetics of the Improved Formulations

For tissue distribution and blood kinetic studies, iodinated [$^{125}$I]-conjugates (i.e., [$^{125}$I]-TxlAn conjugates) and [$^{3}$H]-Taxol were used. Briefly, TxlAn2 conjugates (1 mg) were radioiodinated using iodobeads and Txl-[$^{125}$I]-An2. Conjugate was then purified using a column containing resource RPC resin. Free iodine was removed by washing the column thoroughly with 20% acetonitrile. During column washes radioactivity was counted to assess the decrease in free iodine. The Txl-[$^{125}$I]-An2 conjugate was then pulled-down by a 100% acetonitrile wash. Acetonitrile was then evaporated and the iodinated conjugate was diluted in 100% DMSO (100 μL). An aliquot of the radioiodinated conjugate was then injected in HPLC and fractions were collected to verify that the radioactivity was associated to the fractions corresponding to the conjugates.

Figure 19A:
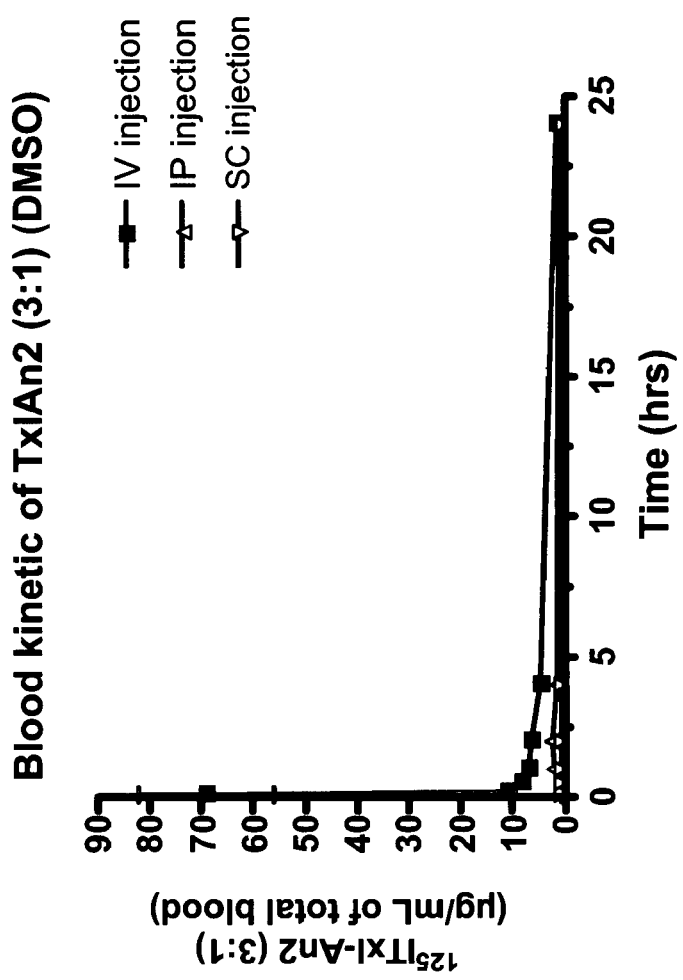
FIG. 19A is a diagram illustrating the blood kinetics of TxlAn2 (3:1) conjugate in DMSO 80% after a bolus injection.

Blood kinetics were assessed after intravenous ((i.v.) tail vein), intraperitoneal (i.p.) and subcutaneous (s.c.) injections performed on awake mice (FIG. 19) Briefly TxlAn2 (3:1) conjugate was diluted in DMSO/Ringer-Hepes (80/20) or in macrogol 15 hydroxystearate (Solutol®)/Ringer-Hepes (20/80), Txl-[$^{125}$I]-An2. Injections of CD-1 mice with the formulations were then performed to obtain a 10 mg/kg concentration. After injections blood fractions (50 μL) were collected at the tail end and radioactivity was directly assessed. Using the same protocol, Taxol blood kinetic was also determined using [$^3$H]-Taxol. Taxol was dissolved in DMSO/Ringer-Hepes (80/20) at a concentration allowing a 5 mg/kg injection and [$^3$H]-Taxol was then added (2.5 µCi/injection). After injections blood fractions were collected at the tail end, scintillation cocktail was added and radioactivity was counted in a Packard counter. Results of this experiment are illustrated in FIG. 19A, FIG. 19 and in FIG. 19C and are summarized in Table 6 below.

Figure 19B:
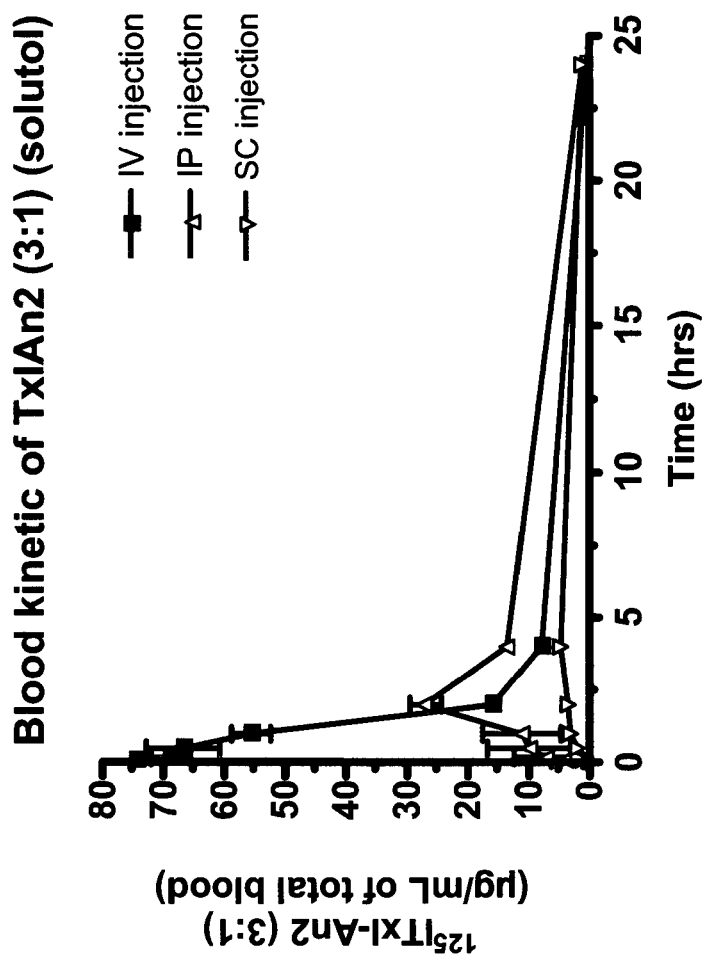
FIG. 19B is a diagram illustrating the blood kinetics of Tx1An2 (3:1) conjugate in macrogol 15 hydroxystearate (SOLUTOL® HS 15) 20% after a bolus injection.
Figure 19C:
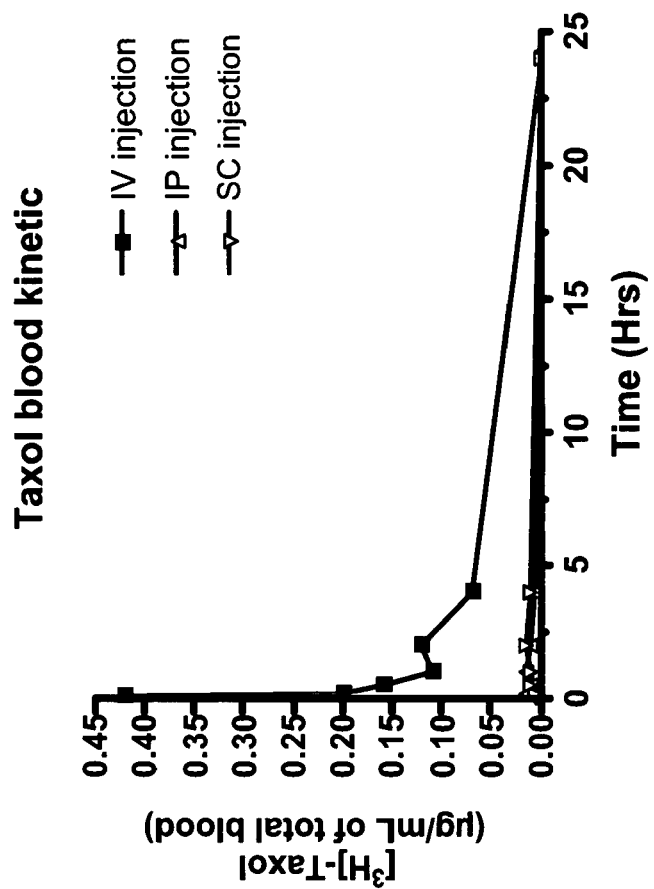
FIG. 19C is a diagram illustrating the blood kinetics of Taxol in DMSO 80% after a bolus injection.

In summary, results of FIG. 19 and Table 6 show that TxlAn2 bioavailability is much higher than Taxol bioavailability. For example, the AUC$_{(0-24hrs)}$ TxlAn2/AUC$_{(0-24hrs)}$ Taxol is 169 (i.e., 203.3/1.2).

In terms of Taxol, the AUC$_{(0-24hrs)}$ TxlAn2/AUC$_{(0-24hrs)}$ Taxol is 84.7 (i.e., 101.65/1.2).

Since there is three Taxol molecules on each molecule of Angiopep-2, the amount of Taxol represents about 0.5 of Angiopep's molecular weight (i.e., 3×854/5301). Therefore the AUC of the conjugate (i.e., 203) has to be multiplied by 0.5 in order to be expressed in term of Taxol.

In addition the blood biodisponibility of TxlAn2 conjugates is equivalent after intravenous and intraperitoneal injections whereas this is not the case for Taxol. Finally, results of FIG. 19 and Table 6 indicate that the blood biodisponibility of TxlAn2 is higher when macrogol 15 hydroxystearate (Solutol®) is used as solubilizer compared to DMSO.

tol®)/Ringer-Hepes (20%/80%) or in DMSO/Ringer-Hepes (80/20). Briefly CD-1 mice were injected via the tail vein with a formulation of TxlAn2 solubilized in macrogol 15 hydroxystearate (Solutol®) or DMSO and also containing Txl-[$^{125}$I]-An2. At predetermined time points a blood sample was collected and anesthetized mice were perfused with cold PBS. Tissues were then excised and radioactivity was counted in a gamma counter.

Figure 20:
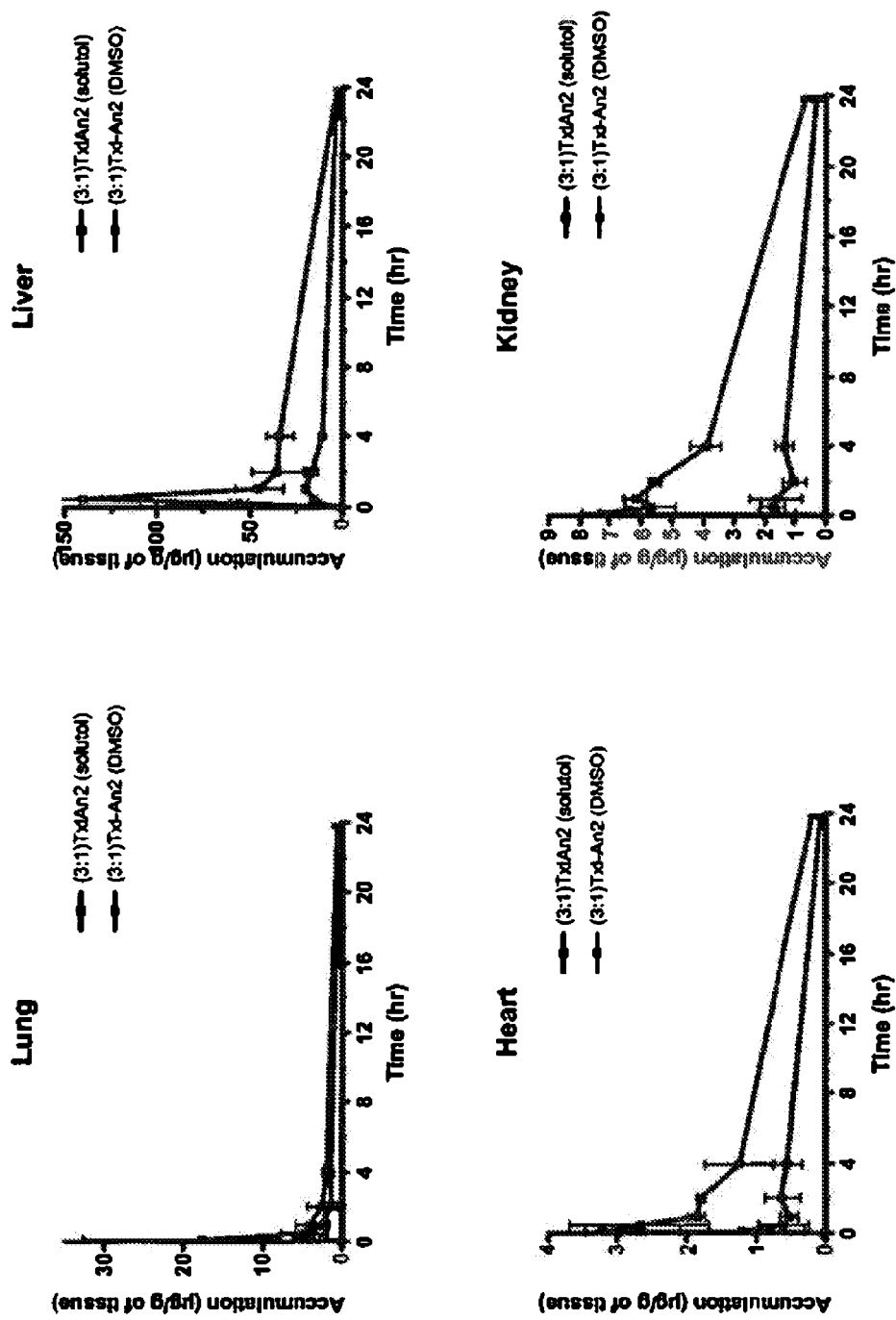
FIG. 20 are diagrams of tissue distribution or Tx1An2 (3:1) conjugate diluted in DMSO (80%) or macrogol 15 hydroxystearate (SOLUTOL® HS51) (20%)
Figure 20:
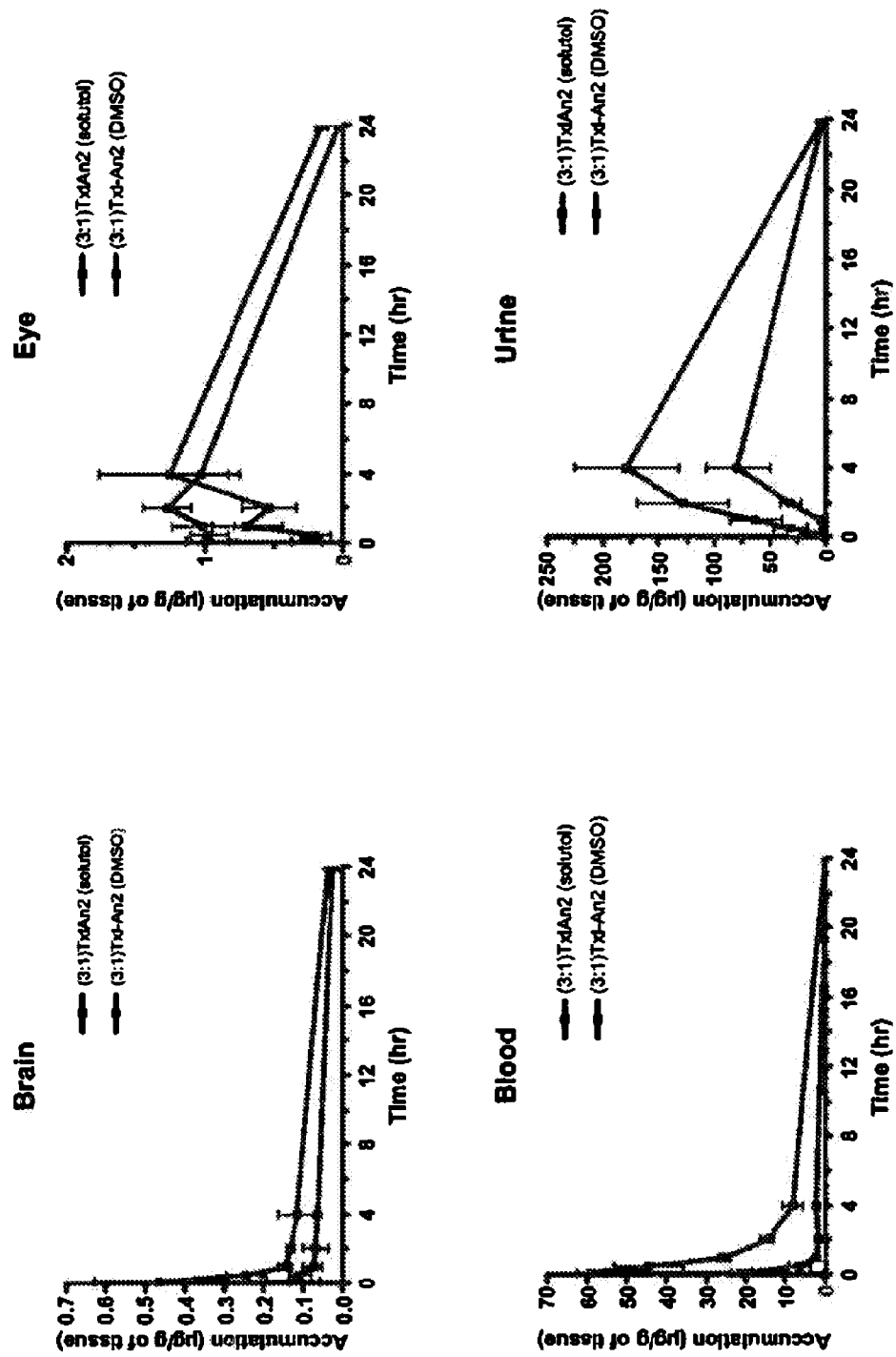

Results of FIG. 20 show that the use of macrogol 15 hydroxystearate (Solutol®) allows a higher distribution of TxlAn2 (3:1) conjugate in most tissues.

Example 13—Preliminary Comparative Toxicity of Paclitaxel and TxlAn2 (3:1) Conjugate A direct comparison of the toxicity of paclitaxel versus TxlAn2 (3:1) conjugate was made on beagle dogs, using IV injection of 2.5 mg/kg of paclitaxel vs 5 mg/kg of TxlAn2 (3:1) conjugate. Four dogs were treated in each cohort. The following observation was made:

Preclinical Observation

During initial infusion, paclitaxel was not well tolerated, as opposed to TxlAn2 (3:1) conjugate which was very well tolerated.

Later on, the paclitaxel group lost weight during days 2 and 3 and recovered. No significant weight loss for TxlAn2 (3:1) conjugate.

Biological Observation

TABLE 7

| | Clinical pathology | | | | | |
|---|---|---|---|---|---|---|
| | White Blood Cells ×109 cells/L | | Reticulocytes ×1012 cells/L | | Platelets ×109 cells/L | |
| | Taxol ® | TxlAn2 (3:1) conjugate | Taxol ® | TxlAn2 (3:1) conjugate | Taxol ® | TxlAn2 (3:1) conjugate |
| Pre-treatment | 9.7 | 10.6 | 0.031 | 0.044 | 250 | 275 |
| 4-days post-treatment | 4.3 | 9.7 | 0.011 | 0.065 | 200 | 275 |
| 8-days post treatment | 8.7 | 10.4 | 0.11 | 0.10 | 340 | 290 |

TABLE 6

Area under curves from 0 to 24 hours were calculated using GraphPad software.

| AUC (0-24 h) (µg · h per mL) | Intravenous injection | Intraperitoneal injection | Subcutaneous injection |
|---|---|---|---|
| TxlAn2 (3:1) (DMSO) (10 mg/kg) | 98.1 | 34.7 | 15.5 |
| TxlAn2 (3:1) (Macrogol 15 hydroxystearate (Solutol ®) (10 mg/kg) | 203.3 | 211.3 | 74.5 |
| Taxol (DMSO) (5 mg/kg) | 1.2 | 0.09 | 0.14 |

Example 12—Tissue Distribution

TxlAn2 tissue distribution was evaluated in normal CD-1 mice after tail vein intravenous injection of 10 mg/kg TxlAn2 solubilized in macrogol 15 hydroxystearate (Solu- These biological observations demonstrate that at an equivalent molecular dose of Taxol®, TxlAn2 (3:1) conjugate does not trigger bone marrow toxicity as opposed to paclitaxel alone. The more favorable toxicity profile than paclitaxel will allow administration of TxlAn2 (3:1) conjugate at a higher dosage than Taxol®, thus further increasing the concentration of active drug to the tumor.

Example 14—Toxicity Studies

Single Acute Dose Toxicity in Rats and Dogs (GLP)
Single infusions of 0, 100, 200, 400, 850 mg/m$^2$ (14-120 mg/kg of TxlAn2 (3:1) conjugate) in rats (n=3/sex/group):
  The observations are as fellows:
  Dose-dependent hematological effects (decreased platelets, WBCs and reticulocytes) observed at all dose levels—maximum effects on Day 4 with recovery thereafter
  Some decreases in body weight gain (10-15%) at 850 mg/m2
  Clinical chemistry normal, no remarkable macroscopic findings
  Maximum Tolerated Dose (MTD) determined at 400 mg/m$^2$ or 56 mg/kg Single infusions of 0, 100, 200, 400 mg/m² (5-20 mg/kg of TxlAn2 (3:1) conjugate) in dogs (n=1/sex/group):
  The observations are as fellows:
  Transient anaphylactoid reactions (face and head swelling) to macrogol 15 hydroxystearate (Solutol®)
  Dose-dependent hematological effects
  High dose male and female dogs sacrificed on Day 4
  Mid dose not well tolerated by female (poor food consumption for ~1 week)
  MTD determined to be at 200 mg/m² or 20 mg/kg
Dose Range Finding Toxicity Studies in Rats and Dogs (Non-GLP)
Twice weekly infusions of 0, 25, 75, 150 mg/m² for 2 weeks (4 doses total) in rats (n=3/sex/group):
  The observations are as follows:
  Dose-dependent hematological effects (platelets, WBCs, reticulocytes, Hb)
  1 high dose female found dead on Day 10 (2 days post 3rd dose); 1 high dose male sacrificed on Day 15 (4 days post 4th dose)—both rats had low hematological values
  Infusion twice a week at 75 mg/m² is well tolerated for 2 weeks.
Twice weekly infusions of 0, 25, 75, 150 mg/m² for 2 weeks (4 doses total) in dogs (n=1/sex/group):
  The observations are as follows:
  Dose-dependent hematological effects (platelets, WBCs, reticulocytes, Hb)
  High dose female found dead on Day 7 and high dose male sacrificed on Day 7 (poor food consumption and body deterioration)
  Infusion twice a week at 75 mg/m² is well tolerated for 2 weeks.
TxlAn2 (3:1) conjugate is well tolerated and as indicated in Table 8 is better tolerated than Paclitaxel or Abraxane.

TABLE 8

MTD comparison with Paclitaxel: data based on rat GLP toxicity programs

| Product | MTD | Improvement compared to Paclitaxel |
| --- | --- | --- |
| Paclitaxel | 8 mg/kg | 3.5 times |
| TxlAn2 (3:1) conjugate | 56 mg/kg (28 mg/kg) | |
| Abraxane (ABI-007) Abraxis Inc. Paclitaxel incorporated and bound to human serum albumin associated to nanoparticles | 12 mg/kg | 1.5 times |
| Tocosol-Paclitaxel (TP) Sonus Pharmaceutical Inc. Vitamin E based Taxol Emulsion incorporating a Pgp inhibitor and particle size-based tumour | 12 mg/kg | 1.5 times |
| Xyotax (PG-TXL) Cell Therapeutics Inc. Paclitaxel polyglumex, biodegradable polyglutamate polymer of paclitaxel | 16 mg/kg | 2 times |

Example 15—Distribution in Brain Tumors

In an attempt to evaluate the distribution of TxlAn2 (3:1) conjugate in a brain tumor model, nude mice were intracerebrally implanted with NCI-H460 lung cancer cells. Ten days after implantation, mice weight loss was significant indicating that the brain tumors were well established. Taxol, TxlAn2 (3:1) and TxlAn2 (2:1) tissue distributions were evaluated (FIG. 21), as precedently described.

Mice were thus given an intravenous injection of either Taxol (5 mg/kg) solubilized in DMSO or TxlAn2 (3:1) (10 mg/kg) or TxlAn2 (2:1) (12.5 mg/kg) each solubilized in macrogol 15 hydroxystearate (Solutol®). After 10 minutes, mice were perfused on ice using cold PBS, organs were collected and radioactivity was measured. To evaluate the difference of accumulation between normal brain and brain tumor, brains were cut in half with the right hemisphere (site of injection of the tumor cells) corresponding to the tumor brain and the left hemisphere to the normal brain.

Figure 21A:
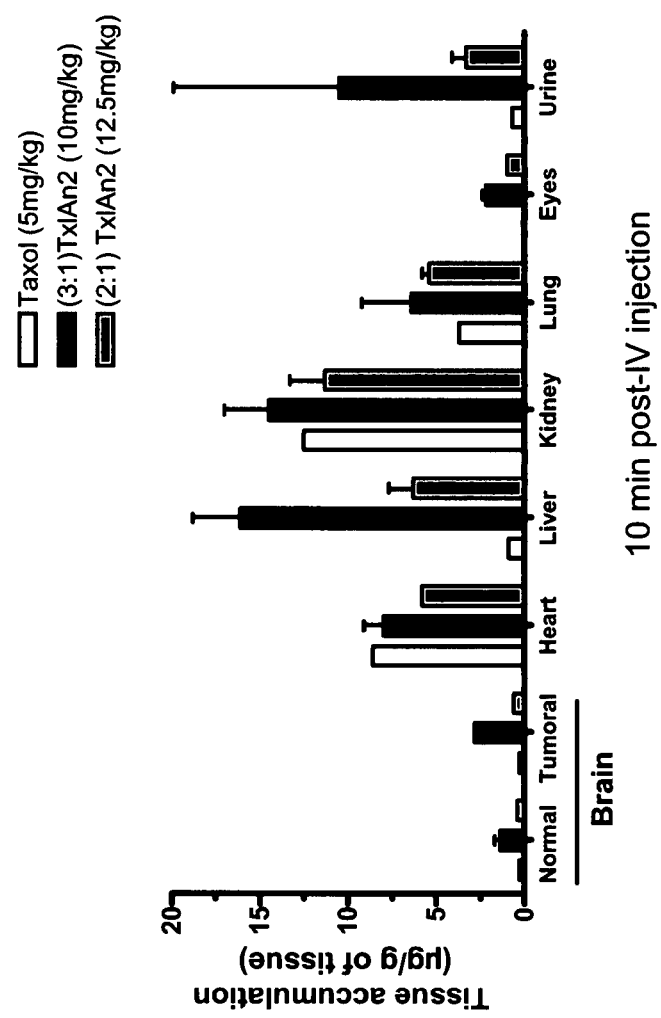
FIG. 21A is an histogram illustrating tissue distribution of Taxol, TxlAn2 (3:1) and TxlAn2 (2:1) after intravenous (i.v.) injection in several tissues.
Figure 21B:
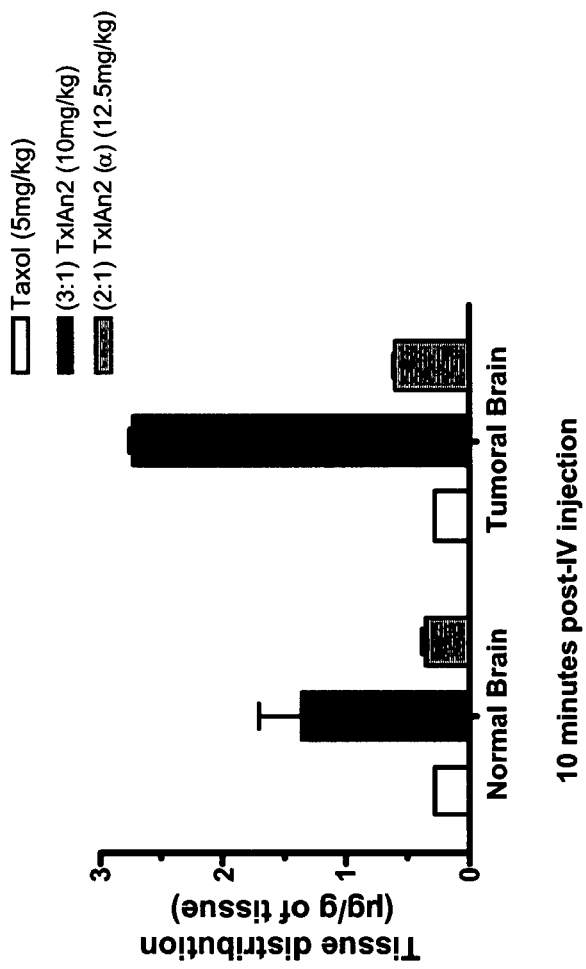
FIG. 21B is an histogram illustrating tissue distribution of Taxol, TxlAn2 (3:1) and TxlAn2 (2:1) after intravenous (i.v.) injection in normal and tumoral brain.

Results of FIG. 21A and FIG. 21B show that TxlAn2 (3:1) conjugates present a higher distribution in brain tumor compared to normal brain (2-fold increase) whereas no difference is observed for Taxol distribution between normal and tumoral brain. TxlAn2 (3:1) conjugate distribution is much higher than Taxol distribution in brain tumor (10-fold increase) and was also higher than TxlAn2 (2:1) distribution (4.5-fold).

Example 16

Effect of Taxol-Angiopep Conjugates Improved Formulation on s.c. Tumor Growth

In vivo studies were conducted to determine whether the improved formulation comprising the Taxol-Angiopep conjugate could inhibit lung cancer cell (NCI-H460) growth or glioblastoma cells (U87) growth in an in vivo model of mice implanted subcutaneously with these cancer cells.

Briefly, mice received a subcutaneous injection of 2.5× $10^6$ human U87 glioma cells or NCI-H460 cells. When tumor growth was observed, mice received treatment with free Taxol, Taxol-Angiopep conjugates or vehicle by i.v. or i.p. injections. Treatments were then administered twice a week until animals were sacrificed. Mice were monitored every day for clinical symptoms and weight loss. Tumor volume was estimated with a kaliper and the following equation (tumor volume=$\pi/2\times$(length (mm)$\times$width² (mm)).

Figure 22A:
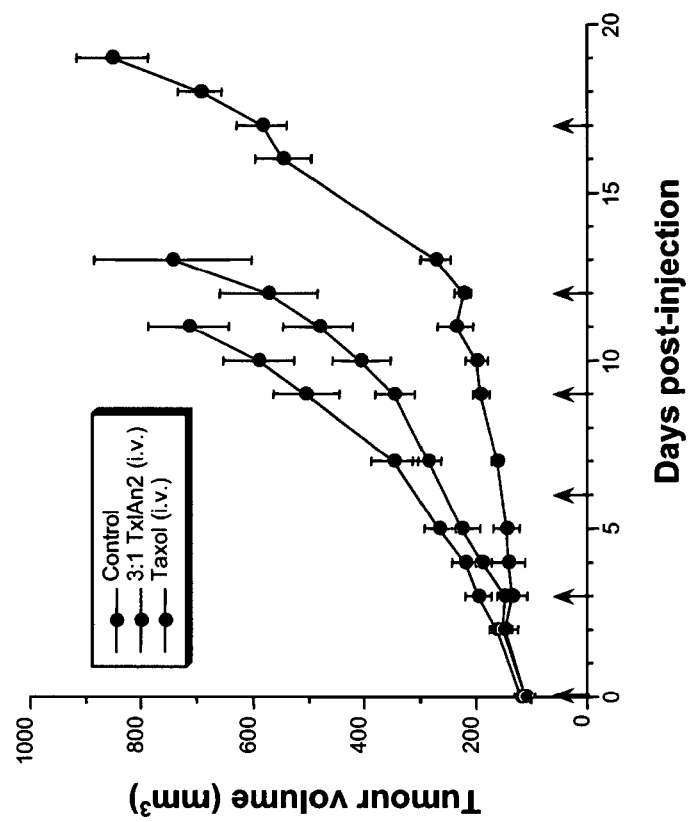
FIG. 22A is a graph illustrating tumor volume following i.v. administration of Taxol (10 mg/kg) or TxlAn2 (3:1) conjugate (20 mg/kg) formulation (in macrogol 15 hydroxystearate (SOLUTOL®) in mice with NCI-H460 cells implanted in their right flank.
Figure 22B:
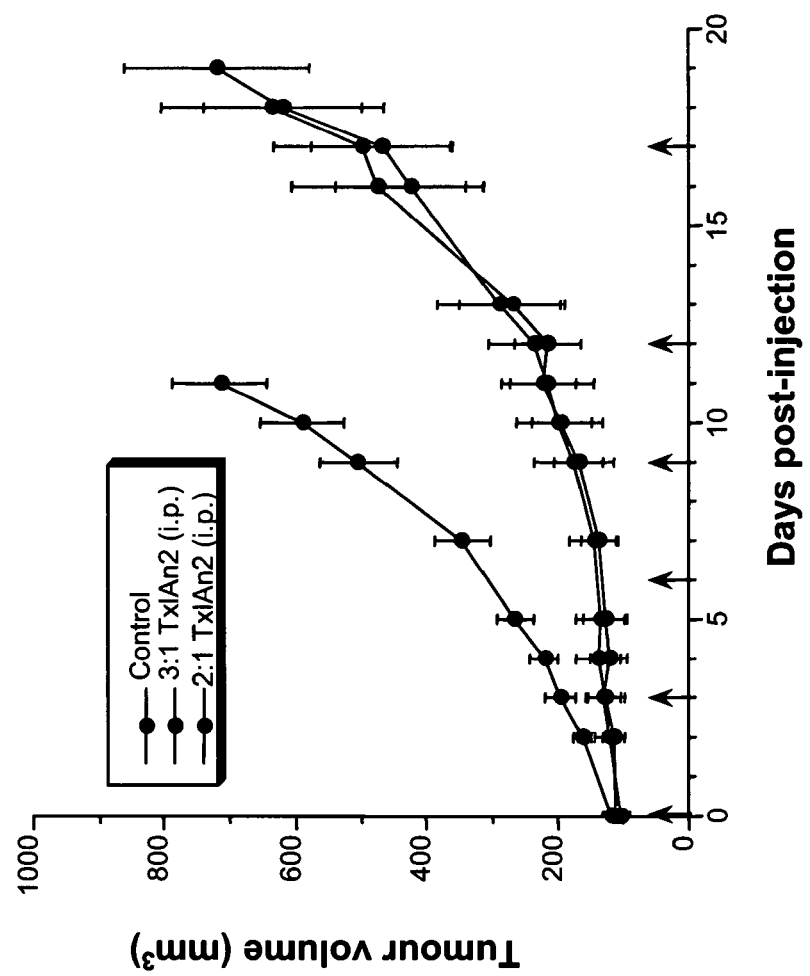
FIG. 22B is a graph illustrating tumor volume following i.p. administration of Tx1An2 (2:1) or Tx1An2 (3:1) conjugate formulation (macrogol 15 hydroxystearate (SOLUTOL®)) in mice with NCI-H460 cells implanted in their right flank.

In the first subcutaneous tumor growth study, NCI-H460 cells were implanted in mice right flank (FIG. 22A). Mice received the vehicle, Taxol or Taxol-Angiopep-2 (3:1) conjugate formulation by i.v. injections in the tail vein or i.p. injections. Conjugates were administered at an equivalent of 10 mg/kg of Taxol. Results presented in FIG. 22 show that the improved formulation of TxlAn2 (3:1) conjugate containing 20% macrogol 15 hydroxystearate (Solutol® HS15) in Ringer/Hepes solution (pH 5.5) caused a much stronger inhibition of NCI-H460 tumor growth than Taxol. These results are also summarized in Table 9 below.

TABLE 9

| Molecules | Tumor volume (mm³) Days post-injection | | Tumor growth | T/C |
| --- | --- | --- | --- | --- |
| | Day 0 | Day 11 | Δ (mm³) | (%) |
| Macrogol 15 hydroxystearate (Solutol®) | 118 ± 11 | 714 ± 71 | 596 ± 62 | 100 |
| Taxol i.v. | 112 ± 12 | 483 ± 63 | 371 ± 58 | 62 |
| TxlAn-2 (3:1) i.v. | 112 ± 18 | 236 ± 32 | 124 ± 14 | 21 |
| TxlAn-2 (3:1) i.p. | 105 ± 14 | 221 ± 50 | 116 ± 37 | 19 |
| TxlAn-2 (2:1) i.p. | 111 ± 18 | 215 ± 70 | 104 ± 53 | 17 |

These results indicate that the TxlAn conjugates are more potent than Taxol at inhibiting tumor growth in an in vivo setting. In addition, similar results where obtained whether the conjugate was administered i.v. or i.p. Finally, similar results where also obtained TxlAn conjugates comprising 2 or 3 Taxol molecules.

Figure 23A:
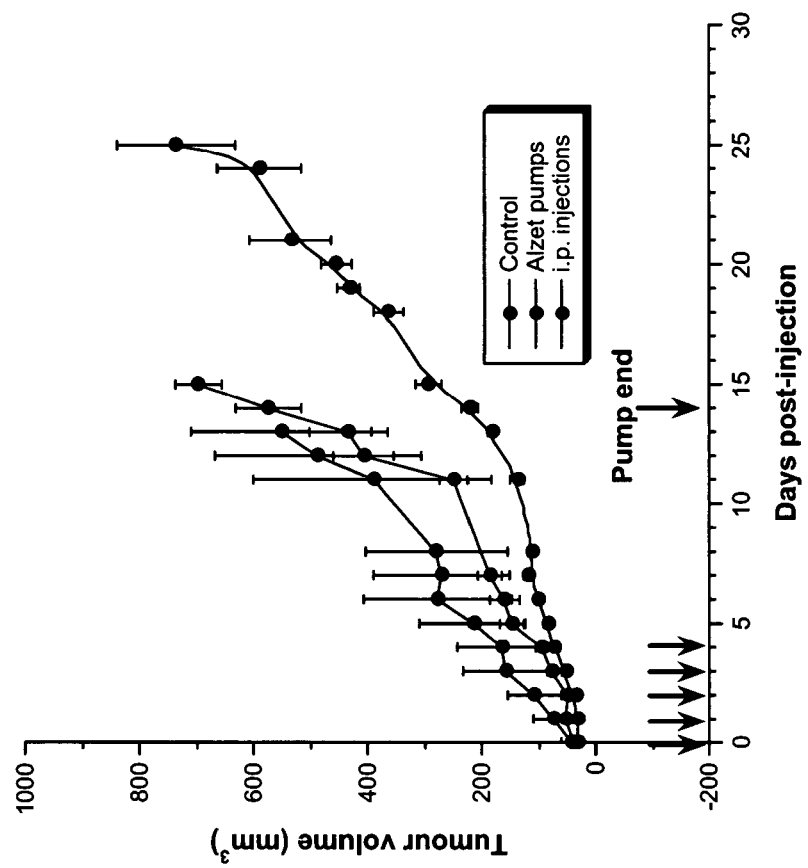
FIG. 23A is a graph illustrating tumor volume following administration of either the vehicle (control), Taxol (10 mg/kg) or TxlAn2 (3:1) formulation (20 mg/kg) by i.p. injections or infusion with Alzet pumps (30 mg/kg/14 days) in mice with NCI-H460 cells implanted in their right flank; Treatments are indicated by arrows.
Figure 23B:
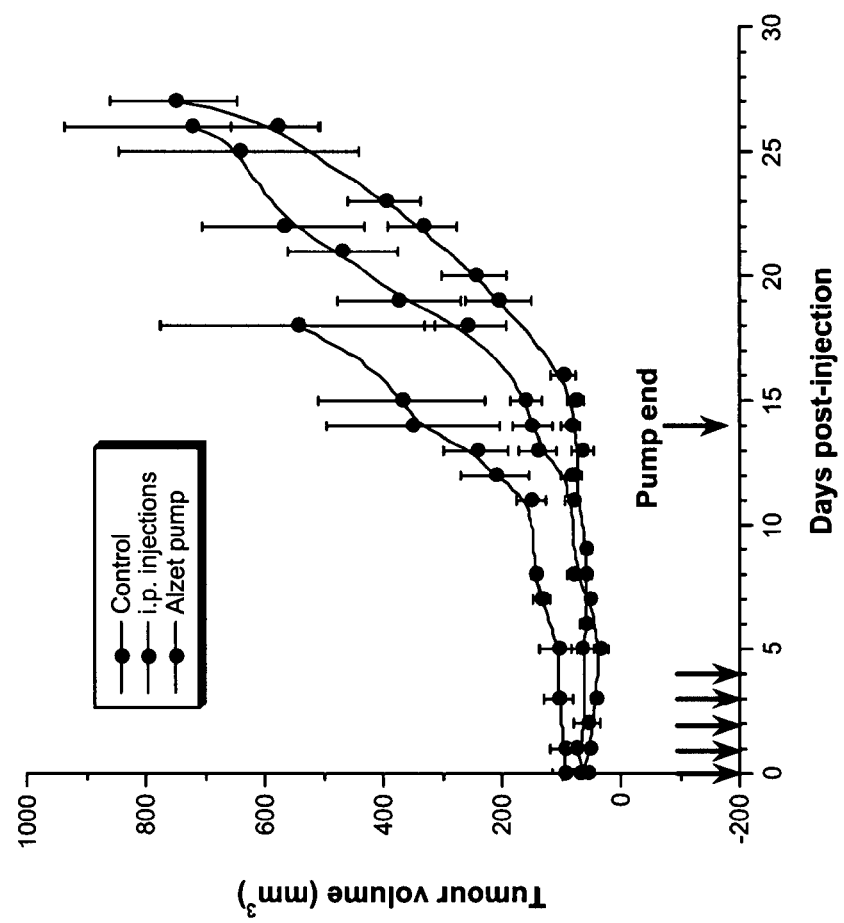
FIG. 23B is a graph illustrating tumor volume following administration of either the vehicle (control), Taxol (10 mg/kg) or TxlAn2 (3:1) formulation (20 mg/kg) by i.p. injections or infusion with Alzet pumps in mice with U87 cells implanted in their right flank; Treatments are indicated by arrows.

Example 17—Effect of Taxol-Angiopep Conjugates Improved Formulation on s.c. Tumor Growth In a further study, the effect of TxlAn2 (3:1) conjugate formulations on s.c. NCI-H460 or U87 growth was evaluated. Mice were treated by i.p. injections with the improved formulation at 20 mg/kg/day for five consecutive days or by infusion with the implantation of Alzet mini-osmotic pump at a dose of 2 mg/kg/day for 14 days. As shown in FIG. 23A and FIG. 23B, the response of mice to TxlAn2 (3:1) conjugate formulation was higher when mice received the improved formulation by infusion.

These in vivo experiments clearly show the efficacy of the improved formulation against tumor growth of glioblastoma or lung cancer cells. Similar experiments also indicate the efficacy of these improved formulations in prolonging survival of animals (data not shown).

The content of each publication, patent and patent application mentioned in the present application is incorporated herein by reference.

Although the present invention has been described in details herein and illustrated in the accompanying drawings, it is to be understood that the invention is not limited to the embodiments described herein and that various changes and modifications may be effected without departing from the scope or spirit of the present invention.

The invention claimed is:

1. A method for the inhibition of cancer cell growth, said method comprising administering to a patient having cancer a pharmaceutical composition comprising:
    (a) a conjugate comprising:
        (i) a polypeptide comprising the amino acid sequence of Angiopep-2; and
        (ii) an anticancer agent conjugated to said polypeptide; and
    (b) a pharmaceutically acceptable carrier;
    in an amount sufficient to inhibit cancer cell growth.

2. The method of claim 1, wherein said cancer is a brain cancer.

3. The method of claim 2, wherein said brain cancer is a brain metastasis, a glioblastoma, or a glioma.

4. The method of claim 1, wherein said cancer is outside the brain.

5. The method of claim 4, wherein said cancer is a lung tumor, a breast tumor, a kidney tumor, an eye tumor, a liver tumor, a colorectal tumor, a tumor of an urinary organ, or a metastatic cancer from a breast tumor, a lung tumor, a melanoma, or a brain tumor.

6. The method of claim 1, wherein said cancer includes a cell expressing P-glycoprotein.

7. The method of claim 1, wherein said cancer is multiple drug resistant.

8. The method of claim 1, wherein said pharmaceutical composition further comprises:
    (c) a solubilizer.

9. The method of claim 8, wherein said solubilizer is a poly-oxyethylene ester of a fatty acid.

10. The method of claim 9, wherein said poly-oxyethylene ester of a fatty acid is macrogol 15 hydroxystearate.

11. The method of claim 1, wherein said polypeptide is about 19 amino acids to about 50 amino acids in length.

12. The method of claim 1, wherein said polypeptide consists of the amino acid sequence of Angiopep-2.

13. The method of claim 1, wherein one to three anticancer agents are conjugated to said polypeptide.

14. The method of claim 1, wherein said anticancer agent is conjugated to said polypeptide as shown below:

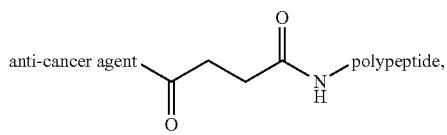

wherein the NH group is either the amino terminal amine or an amino group on a lysine at position 10 or position 15 of the Angiopep-2 sequence.

15. The method of claim 1, wherein said anticancer agent is paclitaxel, vinblastine, vincristine, etoposide, doxorubicin, cyclophosphamide, doclitaxel, melphalan, or chlorambucil.

16. The method of claim 15, wherein said anticancer agent is paclitaxel.

17. The method of claim 16, wherein said conjugate comprises three molecules of paclitaxel.

18. The method of claim 17, wherein said conjugate has the structure:
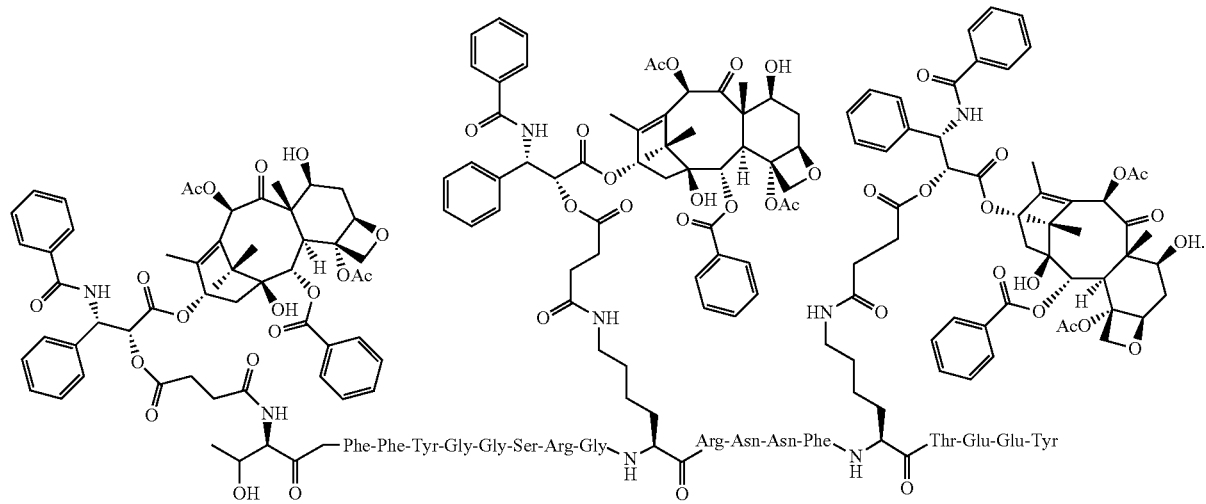
19. The method of claim 1, wherein said pharmaceutical composition further comprises (d) mannitol or (e) a buffer.
* * * * *